(12) United States Patent
Pichichero et al.

(10) Patent No.: US 9,944,680 B2
(45) Date of Patent: Apr. 17, 2018

(54) **COMPOSITION FOR IMMUNIZATION AGAINST *STREPTOCOCCUS PNEUMONIAE***

(75) Inventors: Michael Pichichero, Toronto (CA); Martina Ochs-Onolemhemhen, Toronto (CA)

(73) Assignee: SANDFI PASTEUR LIMITED, Toronto, Ontario (CA)

( * ) Notice: Subject to any disclaimer, the term of this patent is extended or adjusted under 35 U.S.C. 154(b) by 780 days.

(21) Appl. No.: 13/990,853

(22) PCT Filed: Dec. 2, 2011

(86) PCT No.: PCT/US2011/063132
§ 371 (c)(1),
(2), (4) Date: Jun. 25, 2014

(87) PCT Pub. No.: WO2012/075428
PCT Pub. Date: Jun. 7, 2012

(65) Prior Publication Data
US 2015/0017209 A1    Jan. 15, 2015

Related U.S. Application Data

(60) Provisional application No. 61/510,620, filed on Jul. 22, 2011, provisional application No. 61/419,635, filed on Dec. 3, 2010.

(51) Int. Cl.
*A61K 39/09* (2006.01)
*C07K 14/315* (2006.01)
*A61K 39/00* (2006.01)

(52) U.S. Cl.
CPC ........ *C07K 14/3156* (2013.01); *A61K 39/092* (2013.01); *A61K 2039/55* (2013.01)

(58) Field of Classification Search
None
See application file for complete search history.

(56) References Cited

U.S. PATENT DOCUMENTS

| | | |
|---|---|---|
| 5,837,541 A | 11/1998 | Raff |
| 6,582,706 B1 | 6/2003 | Johnson et al. |
| 6,716,432 B1 | 4/2004 | Paton et al. |
| 6,764,686 B2 | 7/2004 | Minetti et al. |
| 7,074,415 B2 | 7/2006 | Hamel et al. |
| 7,078,042 B2 | 7/2006 | Briles et al. |
| 7,122,194 B2 | 10/2006 | Johnson et al. |
| 7,128,918 B1 | 10/2006 | Hamel et al. |
| 7,262,024 B2 | 8/2007 | Hamel et al. |
| 7,635,482 B2 | 12/2009 | Hamel et al. |
| 7,635,487 B2 | 12/2009 | Meinke et al. |
| 8,128,939 B2 | 3/2012 | Tweten |
| 8,404,457 B2 | 3/2013 | Ochs-Onolemhemhen et al. |
| 2003/0021795 A1 | 1/2003 | Houston et al. |
| 2003/0059438 A1 | 3/2003 | Briles et al. |
| 2003/0077293 A1 | 4/2003 | Hamel et al. |
| 2003/0232976 A1 | 4/2003 | Hamel et al. |
| 2004/0081662 A1 | 4/2004 | Hermand et al. |
| 2005/0048590 A1 | 3/2005 | Masure et al. |
| 2005/0214329 A1 | 9/2005 | Laferriere et al. |
| 2006/0051361 A1 | 3/2006 | Laferriere et al. |
| 2006/0177465 A1 | 8/2006 | Hamel et al. |
| 2006/0263846 A1 | 11/2006 | Meinke et al. |
| 2007/0082875 A1 | 4/2007 | Fang et al. |
| 2009/0110699 A1 | 4/2009 | Cigarini et al. |
| 2009/0214537 A1 | 8/2009 | Soriani et al. |
| 2010/0227341 A1 | 9/2010 | Briles et al. |
| 2010/0297133 A1 | 11/2010 | Ochs et al. |
| 2011/0287046 A1 | 11/2011 | Oloo et al. |
| 2013/0034579 A1 | 2/2013 | Harper et al. |
| 2013/0183350 A1 | 7/2013 | Harper et al. |

FOREIGN PATENT DOCUMENTS

| | | |
|---|---|---|
| WO | 93/09811 A1 | 5/1993 |
| WO | 00/39299 A2 | 7/2000 |
| WO | 2004/020609 A2 | 3/2004 |

OTHER PUBLICATIONS

Bowie et al. (Science, 1990, 247:1306-1310).*
Greenspan et al. (Nature Biotechnology 7: 936-937, 1999).*
Adamou, et al. Identification and characterization of a novel family of pneumococcal proteins that are protective against sepsis. Infect Immun. 2001; 69:949-58.
Adkins, et al. The generation of Th memory in neonates versus adults: prolonged primary Th2 effector function and impaired development of Th1 memory effector function in murine neonates. J. Immunol 2001;166(2):918-25.
Adkins, et al. Neonatal adaptive immunity comes of age. Nat.Rev. Immunol. 2004;4(7):553-64.
Barnett, et al. Immune response to pneumococcal conjugate and polysaccharide vaccines in otitis-prone and otitis-free children. Clin.Infect Dis 1999; 29:191-2.
Bentdal, et al. Int. J. Ped. Otorhinolaryngol. 2007; 71:1251-1259.
Berkley, et al. Bacteremia among children admitted to a rural hospital in Kenya. N.Engl.J Med. 2005; 352:39-47.
Berman, et al. Immunoglobulin G, total and subclass, in children with or without recurrent otitis media. J Pediatr 1992; 121:249-51.
Bernasconi, et al. Maintenance of serological memory by polyclonal activation of human memory B cells. Science 2002;298(5601):2199-202.
Bernstein, et al. Immunoglobulin G subclass response to major outer membrane proteins of nontypable Haemophilus influenzae in children with acute otitis media. Otolaryngol.Head Neck Surg. 1997; 116;363-71.
Bluestone, C. Ten-year review of otitis media pathogens. Pediatr Infect Dis J 1992; 11:S7-11.
Bogaert, et al., Lancet Infect. Dis. 4:144-154 (2004).
Breukels, et al. Pneumococcal conjugate vaccine primes for polysaccharide-inducible IgG2 antibody response in children with recurrent otitis media acuta. J Infect Dis 1999; 179:1152-6.

(Continued)

Primary Examiner — Brian Gangle
(74) Attorney, Agent, or Firm — Patrick J. Halloran

(57) ABSTRACT

This disclosure relates to a method of preventing or treating a recurrence of acute otitis media in a subject at risk comprising administering a therapeutically effective amount of a composition, at least once to the subject. The composition administered comprises at least one immunogenic polypeptide selected from the group consisting of *Streptococcus pneumoniae* PhtD, PhtE, PcpA, LytB and detoxified pneumolysin.

11 Claims, 5 Drawing Sheets

(56) References Cited

OTHER PUBLICATIONS

Casey, et al. New patterns in the otopathogens causing acute otitis media six to eight years after introduction of pneumococcal conjugate vaccine. Pediatr.Infect.Dis.J. 2010;29(4):304-9.
Casselbrant, et al JAMA 1999; 282:2125-2130.
Chen, et al. Kinetic Th1/Th2 responses of transgenic mice with bacterial meningitis induced by Haemophilus influenzae. Clin.Sci. (Lond) 2006;111(4):253-63.
Combadiere, et al. Keeping the memory of influenza viruses. Pathol. Biol. (Paris) 2010;58(2):e79-e86.
De Bree, et al. Characterization of CD4+ memory T cell responses directed against common respiratory pathogens in peripheral blood and lung. J.Infect.Dis. 2007;195(11):1718-25.
Del Beccaro, et al. Bacteriology of acute otitis media: a new perspective. J.Pediatr. 1992;120(1):81-4.
Denny, et al.. Acute respiratory infections are the leading cause of death in children in developing countries. Am.J Trop.Med.Hyg. 1986; 35:1-2.
Dhooge, et al. Deficient IgA and IgG2 anti-pneumococcal antibody levels and response to vaccination in otitis prone children. Int. J. Ped. Otor. 64(2): 133-1441 (2002).
Di Fabio et al., Pediatr. Infect. Dis. J. 20:959-967 (2001).
Eskola et al., N. Engl. J. Med. 344-403-409 (2001).
Faden, H. The microbiologic and immunologic basis for recurrent otitis media in children. Eur.J.Pediatr. 2001;160(7):407-13.
Fietta, et al. The effector T helper cell triade. Rev.Biol. 2009;102(1):61-74.
Fleischer, B. Superantigens. APMIS 1994;102(1):3-12.
Forseni, et al. Infiltration of immunocompetent cells in the middle ear during acute otitis media: a temporal study. Am. J. Otol. 1999;20(2):152-7.
Freijd, et al. A prospective study demonstrating an association between plasma IgG2 concentrations and susceptibility to otitis media in children. Scand.J Infect Dis 1985; 17:115-20.
Garcia, et al. LytB, a novel pneumococcal murein hydrolase essential for cell separation. Mol.Microbiol. 1999; 31:1275-81.
Glover, et al. *Streptococcus pneumoniae* surface protein PcpA elicits protection against lung infection and fatal sepsis. Infect Immun. 2008; 76:2767-76.
Hirst et al. Clinical and Experimental Immunology (2004).
Holmlund, et al. Serum antibodies to the pneumococcal surface proteins PhtB and PhtE in Finnish infants and adults. Pediatr Infect Dis J 2007; 26:447-9.
Holmlund, et al. Antibodies to pneumococcal proteins PhtD, CbpA, and LytC in Filipino pregnant women and their infants in relation to pneumcoccal carriage. Clin. Vaccine Immunol. 2009; 16:916-23.
Holt, P. Functionally mature virus-specific CD8(+) T memory cells in congenitally infected newborns: proof of principle for neonatal vaccination? J.Clin.Invest 2003;111(11):1645-7.
Hotomi, et al. Antibody responses to the outer membrane protein P6 of non-typeable Haemophilus influenzae and pneumococcal capsular polysaccharides in otitis-prone children. Acta Otolaryngol. 1999; 119:703-7.
Huang, et al. Post-PCV7 changes in colonizing pneumococcal serotypes in 16 Massachusetts communities, 2001 and 2004. Pediatrics 2005; 116:e408-e413.
Kadioglu, et al. The role of *Streptococcus pneumoniae* virulence factors in host respiratory colonization and disease. Nat.Rev. Microbiol. 2008; 6:288-301.
Kaur, et al. Serum Antibody Response to Three Non-typeable Haemophilus influenzae Outer Membrane Proteins During Acute Otitis Media and Nasopharyngeal Colonization in Otitis Prone and Non-Otitis Prone Children. Vaccine 2011;29(5):1023-8.
Kelley, et al. Immunological memory: the role of B cells in long-term protection against invasive bacterial pathogens. JAMA 2005;294(23):3019-23.
Kirkham, et al. Identification of invasive serotype 1 pneumococcal isolates that express nonhemolytic pneumolysin. J.Clin.Microbiol. 2006;44(1):151-9.

Kirkham, et al. Construction and immunological characterization of a novel nontoxic protective pneumolysin mutant for use in future pneumococcal vaccines. Infect.Immun. 2006;74(1):586-93.
Klein, et al. Preterm infants' T cell responses to inactivated poliovirus vaccine. J. Infect. Dis. 2010;201(2):214-22.
Kodama, et al. Cellular immune response of adenoidal and tonsillar lymphocytes to the P6 outer membrane protein of non-typeable Haemophilus influenzae and its relation to otitis media. Acta Otolaryngol. 1999;119(3):377-83.
Kodama, et al. Induction of specific immunoglobulin A and Th2 immune responses to P6 outer membrane protein of nontypeable Haemophilus influenzae in middle ear mucosa by intranasal immunization. Infect.Immun.2000;68(4):2294-300.
Korn, et al. IL-17 and Th17 Cells. Annu.Rev.Immunol. 2009;27:485-517.
Lanzavecchia, et al. Human B cell memory. Curr.Opin.Immunol. 2009;21(3):298-304.
Luotonen, et al. The bacteriology of acute otitis media in children with special reference to *Streptococcus pneumoniae* as studied by bacteriological and antigen detection methods. Scand.J Infect Dis 1981; 13:177-83.
Malley, et al. Antibody-independent, interleukin-17A-mediated, cross-serotype immunity to pneumococci in mice immunized intranasally with the cell wall polysaccharide. Infect.Immun 2006;74(4):2187-95.
Manz, et al. Maintenance of serum antibody levels. Annu.Rev. Immunol. 2005;23:367-86
Matilla, et al. Adenoids provide a microenvironment CD4(+), CD45RO(+), L-selectin(−), CXCR4(+), CCR5(+) T lymphocytes, a lymphocyte phenotype found in the middle ear effusion. Int.Immunol. 2000;12(9):1235-43.
Mbelle et al., J. Infect. Dis. 180:1171-1176 (1999).
McKinstry, et al. The potential of CD4 T-cell memory Immunology 2010;130(1):1-9.
Mosmann, et al. Diversity of cytokine synthesis and function of mouse CD4+ T cells. Immunol.Rev. 1991;123:209-29.
Mosmann, et al. The expanding universe of T-cell subsets: Th1, Th2 and more. Immunol.Today 1996; 17(3):138-46.
Mulholland, et al. Editorial: The Gambian pneumococcal vaccine trail-implications for control of childhood pneumonia. Trop. Med. Int. Health 10:497-500 (2005).
Mureithi, et al. T cell memory response to pneumococcal protein antigens in an area of high pneumococcal carriage and disease. J.Infect.Dis. 2009;200(5):783-93.
Murphy, et al. Mechanisms of recurrent otitis media: importance of the immune response to bacterial surface antigens. Ann.N.Y.Acad. Sci. 1997;830:353-60.
Musher, et al. Protection against bacteremic pneumococcal infection by antibody to pneumolysin. J Infect Dis 2001; 183:827-30.
Obaro, et al. Pneumococcal surface adhesin A antibody concentration in serum and nasopharyngeal carriage of *Streptococcus pneumoniae* in young African infants. Vaccine 2000; 19:411-2.
Ogunniyi, et al. Pneumococcal histidine triad proteins are regulated by the Zn2+-dependent repressor AdcR and inhibit complement deposition through the recruitment of complement factor H. FASEB J 2009; 23:731-8.
Pelton, et al. Recent advances in otitis media. Pediatr Infect Dis J 2009; 28:S133-S137.
Perfetto, et al. Amine reactive dyes: an effective tool to discriminate live and dead cells in polychromatic flow cytometry. J.Immunol. Methods 2006;313(1-2):199-208.
Pichichero, et al. A safety and immunogenicity comparison of 12 acellular pertussis vaccines and one whole-cell pertussis vaccine given as a fourth dose in 15-to 20-month-old children. Pediatrics 1997;100(5):772-88.
Pichichero, et al. Recurrent and persistent otitis media. Pediatr. Infect.Dis.J. 2000;19(9):911-6.
Pichichero, et al. Otitis media. Expert.Opin.Pharmacother. 2002;3(8):1073-90.
Pichichero, et al. Pathogens causing recurrent and difficult-to-treat acute otitis media, 2003-2006. Clin.Pediatr (Phila) 2008; 47:901-6.

(56) References Cited

OTHER PUBLICATIONS

Pichichero, et al. Antibody Response to Haemophilus influenzae Outer Membrane Protein D, P6, and OMP26 After Nasopharyngeal Colonization and Acute Otitis Media in Children. Vaccine 2010; 28:7184-92.

Pichichero, et al. Antibody Response to *Streptococcus pneumoniae* Vaccine Targets PhtD, LytB, PcpA, PhtE and PlyD1 After Nasopharyngeal Colonization and Acute Otitis Media in Children. 10th International Symposium on Recent Advances in Otitis Media. New Orleans LA, USA, Abstract J03, p. 105, Jun. 5-9, 2011.

Picker, et al. Direct demonstration of cytokine synthesis heterogeneity among human memory/effector T cells by flow cytometry. Blood 1995;86(4):1408-19.

Pitcher, et al. HIV-1-specific CD4+ T cells are detectable in most individuals with active HIV-1 infection, but decline with prolonged viral suppression. Nat.Med. 1999;5(5):518-25.

Poehling, et al. Reduction of frequent otitis media and pressure-equalizing tube insertions in children after introduction of pneumococcal conjugate vaccine. Pediatrics 2007;119(4):707-15.

Prellner, et al. Pneumococcal antibodies and complement during and after periods of recurrent otitis. Int.J Pediatr Otorhinolaryngol. 1984; 7:39-49.

Prellner, et al. Responses to rubella, tetanus, and diphtheria vaccines in otitis-prone and non-otitis-prone children. Ann.Otol.Rhinol. Laryngol. 1990; 99:628-32.

Rajewsky, K. Clonal selection and learning in the antibody system. Nature 1996;381(6585):751-8.

Rapola, et al. Antibody response to the pneumococcal proteins pneumococcal surface adhesin A and pneumolysin in children with acute otitis media. Pediatr Infect Dis J 2001; 20:482-7.

Rosenow, et al. Contribution of novel choline-binding proteins to adherence, colonization and immunogenicity of *Streptococcus pneumoniae*. Mol.Microbiol. 1997; 25:819-29.

Shapiro et. al. N. Engl. J. Med. 325:1453-1460 (1991).

Sharma, et al. Reduced memory CD4+ T-cell generation in the circulation of young children may contribute to the otitis-prone condition. J. Inf. Dis. 204: 645-653 (2011).

Siegrist, C. Neonatal and early life vaccinology. Vaccine 2001;19(25-26):3331-46.

Skotnicka, et al. Lymphocyte subpopulations in middle ear effusions: flow cytometry analysis. Otol. Neurotol. 2005;26(4):567-71.

Slifka, et al. Humoral immunity due to long-lived plasma cells. Immunity. 1998;8(3):363-72.

Soininen, et al. Natural development of antibodies to pneumococcal capsular polysaccharides depends on the serotype: association with pneumococcal carriage and acute otitis media in young children. J Infect Dis 2001; 184:569-76.

Soininen, et al. Antibody response to pneumococcal capsular polysaccharides in children with acute otitis media. Pediatr Infect Dis J 2002; 21:186-92.

Teele, et al. Epidemiology of otitis media during the first seven years of life in children in greater Boston: a prospective, cohort study. J.Infect.Dis. 1989;160(1):83-94.

Tu, et al. Persistent and selective deficiency of CD4+ T cell immunity to cytomegalovirus in immunocompetent young children. J. Immunol. 2004;172(5):3260-7.

Upham, et al. Dendritic cell immaturity during infancy restricts the capacity to express vaccine-specific T-cell memory. Infect.Immun. 2006;74(2):1106-12.

Van Den Biggelaar, et al. Neonatal pneumococcal conjugate vaccine immunization primes T cells for preferential Th2 cytokine expression: a randomized controlled trial in Papua New Guinea. Vaccine 2009;27(9):1340-7.

Van Leeuwen, et al. Generation and maintenance of memory CD4(+) T Cells. Curr.Opin.Immunol 2009;21(2):167-72.

Vergison, et al. Otitis media and its consequences: beyond the earache. Lancet Infect.Dis. 2010;10(3):195-203.

Waldrop, et al. Determination of antigen-specific memory/effector CD4+ T cell frequencies by flow cytometry: evidence for a novel, anitgen-specific homeostatic mechanism in HIV-associated immunodeficiency. J.Clin.Invest 1997;99(7):1739-50.

Waldrop, et al. Normal human CD4+ memory T cells display broad heterogeneity in their activation threshold for cytokine synthesis. J.Immunol. 1998;161(10):5284-95.

Walker, et al. Molecular cloning, characterization, and complete nucleotide sequence of the gene for pneumolysin, the sulfhydryl-activated toxin of *Streptococcus pneumoniae*. Infect Immun. 1987; 55:1184-9.

Wiertsema, et al. Antibody levels after regular childhood vaccinations in the immunological screening of children with recurrent otitis media. J Clin.Immunol. 2004; 24:354-60.

Yamanaka, et al. Antibody response to outer membrane protein of nontypeable Haemophilus influenzae in otitis-prone children. J Pediatr 1993; 122:212-8.

Yamanaka, et al. Local antibody response to P6 of nontypable Haemophilus influenzae in otitis-prone and normal children. Acta Otolaryngol. 1993; 113:524-9.

Zaghouani, et al. Neonatal immunity: faulty T-helpers and the shortcomings of dendritic cells. Trends Immunol. 2009;30(12):585-91.

Zhang, et al. Serum and mucosal antibody responses to pneumococcal protein antigens in children: relationships with carriage status. Eur.J Immunol. 2006; 36:46-57.

Zhang, et al. Low CD4 T cell immunity to pneumolysin is associated with nasopharyngeal carriage of pneumococci in children. J.Infect.Dis. 2007;195(8):1194-202.

GenBank Accession No. AAK06760. Pneumococcal histidine triad protein D precursor, partial (*Streptococcus pneumoniae*); Feb. 11, 2001.

GenBank Accession No. AAK06761. Pneumococcal histidine triad protein E precursor, partial (*Streptococcus pneumoniae*); Feb. 11, 2001.

GenBank Accession No. AAK19156. Endo-beta-N-acetylglucosaminidase (*Streptococcus pneumoniae*); Mar. 15, 2001.

GenBank Accession No. AAK75086. Endo-beta-N-acetylglucosaminidase (*Streptococcus pneumoniae* TIGR 4); Jan. 31, 2014.

GenBank Accession No. AAK76194. Choline binding protein PcpA (*Streptococcus pneumoniae* TIGR 4); Jan. 31, 2014.

GenBank Accession No. ABJ55408. Endo-beta-N-acetylglucosaminidase precursor, putative (*Streptococcus pneumoniae* D39); Jan. 31, 2014.

GenBank Accession No. ABO21381. Pneumolysin (*Streptococcus pneumoniae* D39); Jan. 11, 2010.

GenBank Accession No. CAA09078. Endo-beta-N-acetylglucosaminidase (*Streptococcus pneumoniae*); Nov. 14, 2006.

GenBank Accession No. CAB04758. PCPA (*Streptococcus pneumoniae*); Nov. 14, 2006.

GenBank Accession No. NP358461. Endo-beta-N-acetylglucosaminidase (*Streptococcus pneumoniae* R6); Jun. 26, 2014.

GenBank Accession No. NP358501. Pneumococcal histidine triad protein D (*Streptococcus pneumoniae* R6); Jun. 26, 2014.

GenBank Accession No. NP358502. Pneumococcal histidine triad protein E (*Streptococcus pneumoniae* R6); Jun. 26, 2014.

GenBank Accession No. NP359536. Choline binding protein PcpA (*Streptococcus pneumoniae* R6); Jun. 26, 2014.

GenBank Accession No. P0C2J9. RecName: Full=Pneumolysin; AltName: Full=Thiol-activated cytolysin (*Streptococcus pneumoniae* TIGR4); May 14, 2014.

GenBank Accession No. Q04IN8. RecName: Full=Pneumolysin; AltName: Full=Thiol-activated cytolysin (*Streptococcus pneumoniae* D39); May 14, 2014.

GenBank Accession No. Q7ZAK5. RecName: Full=Pneumolysin; AltName: Full=Thiol-activated cytolysin (*Streptococcus pneumoniae* R6); May 14, 2014.

GenBank Accession No. YP816335. Endo-beta-N-acetylglucosaminidase (*Streptococcus pneumoniae* D39); Jun. 10, 2013.

GenBank Accession No. YP816370. Histidine triad protein D (*Streptococcus pneumoniae* D39); Jun. 10, 2013.

(56) References Cited

OTHER PUBLICATIONS

GenBank Accession No. YP816371. Histidine triad protein E (*Streptococcus pneumoniae* D39); Jun. 10, 2013.
GenBank Accession No. YP817353. Choline binding protein PcpA (*Streptococcus pneumoniae* D39); Jun. 10, 2013.
GenBank Accession No. ZP01833419. Choline binding protein PcpA (*Streptococcus pneumoniae* SP19-B575); Nov. 9, 2010.
GenBank Accession No. ZP01835022. Choline binding protein PcpA (*Streptococcus pneumoniae* SP23-BS72); Nov. 9, 2010.
Garcia-Suarez, et al. Protection Against Pneumococcal Pneumonie in Mice by Monoclonal Antibodies to Pneumolysin. Inf. Imm. 72(8): 4534-4540 (2004).
Holmlund, et al. Development of Natural Antibodies to Pneumococcal Surface Protein A, Pneumococcal Surface Adhesin A and Pneumolysin in Filipino Pregnant Women and Their Infants in Relation to Pneumococcal Carriage. Vaccine 24: 57-65 (2006).
Lynch, et al. *Streptococcus pneumoniae*: Epidemiology and Risk Factors, Evolution of Antimicrobial Resistance, and Impact of Vaccines. Curr. Op. Pulm. Med. 16: 217-225 (2010).
Pavia, et al. Efficacy of Pneumococcal Vaccination in Children Younger Than 24 Months: A Meta-Analysis. Pediatrics, 123(6): e1103-e1110 (2009).
Simell, et al. Pneumococcal Carnage and Acute Otitis Media Induce Serum Antibodies to Pneumococcal Surface Proteins CbpA and PhtD in Children. Vaccine, 27: 4615-4621 (2009).
Verkaik, et al. Induction of Antibodies by *Staphylococcus aureus* Nasal Colonization in Young Children. Clin. Microbiol. Infect. 16: 1312-1317 (2010).
Vila-Corcoles, et al. Effectivess of the 23-Valent Polysaccharide Pneumococcal Vaccine Against Invasive Pneumococcal Disease in People 60 Years or Older. BMC Infectious Diseases, 10: 73 (2010).
Barocchi et al., "Vaccines in the era of genomics: the pneumococcal challenge". Vaccine, vol. 25, No. 16, pp. 2963-2973, Apr. 20, 2007.
Gulimi et al., "New approaches towards the identification antibiotic and vaccine targets in *Streptococcus pneumoniae*". EMBO reports vol. 3, No. 8, pp. 728-734, Aug. 15, 2002.
Hamel et al., "Prevention of Pneumococcal Disease in Mice Immunized with Conserved Surface-Accessible Proteins". Infection and Immunity, vol. 72, No. 5, pp. 2659-2670, May 2004.
Hirst et al., "The role of pneumolysin in pneumococcal pneumonia and meningitis". Clin. Exp. Immunol., vol. 138, No. 2, pp. 195-201, 2004.
Ogunniyi et al., "Development of a vaccine against invasive pneumococcal disease based on combinations of virulence proteins of *Streptococcus pneumoniae*", Infection and Immunity, vol. 75, No. 1, pp. 350-357, Jan. 2007.
Sanchez-Beato et al., "Molecular Characterization of PcpA: a novel choline-binding protein of *Streptococcus pneumoniae*". FEMS Microbiology Letters, vol. 164, No. 1, pp. 207-214, Jul. 1, 1998.
Tai, Stanley S., "*Streptococcus pneumoniae* Protein Vaccine Candidates: Properties, Activities and Animal Studies" Critical Reviews in Microbiology, vol. 32, No. 3, pp. 139-153, Apr. 11, 2006.
Zhang et al., "Recombinant PhpA protein, a unique histidine motif-containing protein from *Streptococcus pneumoniae*, protects mice against intranasal pneumococcal challenge". Infection and Immunity, vol. 69, No. 6, pp. 3827-3836, Jun. 2001.
Alexander, et al. Immunization of mice with pneumolysin toxoid confers a significant degree of protection against at least nine serotypes of *Streptococcus pneumoniae*. Infect. Immun. 62(12):5683-8 (1994).
Benton, et al. A pneumolysin-negative mutant of *Streptococcus pneumoniae* causes chronic bacteremia rather than acute sepsis in mice. Infect. Immun. 63(2):448-55 (1995).
Bergeron, et al. Cytokine kinetics and other host factors in response to pneumococcal pulmonary infection in mice. Infect. Immun. 66(3):912-22 (1998).
Berry, et al. Effect of defined point mutations in the pneumolysin gene on the virulence of *Streptococcus pneumoniae*. Infect. Immun. 63(5):1969-74 (1995).

Berry, et al. Comparative virulence of *Streptococcus pneumoniae* strains with insertion-duplication, point, and deletion mutations in the pneumolysin gene. Infect. Immun. 67(2):981-5 (1999).
Black, et al. In Plotkin, S. et al. eds. Vaccines, 5th Ed., WB Saunders, Chapter 23 (2008).
Bologa, et al. Safety and immunogenicity of the pneumococcal protein vaccine candidates: monovalent choline-binding protein A (PcpA) vaccine and bivalent PcpA-pneumococcal histidine triad protein D vaccine. Vaccine, 30: 7461-68 (2012).
Briles, et al. Immunizations with pneumococcal surface protein A and pneumolysin are protective against pneumonia in a murine model of pulmonary infection with *Streptococcus pneumoniae*. J. Infect. Dis. 188(3):339-48 (2003).
Butler, et al. Serotype Distribution of *Streptococcus pneumoniae* Infections among Preschool Children in the United States, 1978-1994: Implications for Development of a Conjugate Vaccine. J. Infect. Dis. 171(4): 855-889 (1995).
Cockeran, et al. The role of pneumolysin in the pathogenesis of *Streptococcus pneumoniae* infection. Curr. Opin. Infect. Dis. 15(3):235-9 (2002).
De Los Toyos, et al. Functional analysis of pneumolysin by use of monoclonal antibodies. Infect. Immun. 64 (2):480-4 (1996).
De Las, et al. Purification and polar localization of pneumococcal LytB, a putative endo-beta-N-acetylglucosaminidase: the chain-dispersing murein hydrolase. J. Bacterial. 184(18):4988-5000 (2002).
Edwards, et al. Combination vaccines consisting of acellular pertussis vaccines. Pediatr. Infect. Dis. J. 16(4 Suppl.):S97-S102 (1997).
Fedson, et al. The burden of pneumococcal disease among adults in developed and developing countries: what is known and what is not known. Vaccine 17, S11-S18 (1999).
Fedson, et al. "Pneumococcal Polysaccharide Vaccine", pp. 529-588; In Vaccines. S.A. Plotikin and W.A. Orenstein (eds.), W.B. Saunders and Co., Philadelphia, PA (2004).
Feldman, et al. Pneumolysin induces the salient histologic features of pneumococcal infection in the rat lung in vivo. Am. J. Respir. Cell. Mol. Biol. 5(5):416-23 (1991).
Garcia, et al. Pneumococcal disease and vaccination in the Americas: an agenda for accelerated vaccine introduction. Rev. Panam. Salud. Publica. 19(5): 340-8 (2006).
Garcia-Suarez, et al. The role of pneumolysin in mediating lung damage in a lethal pneumococcal pneumonia murine model. Respir. Res. 8:3 (2007).
Giebink, et al. Polymorphonuclear leukocyte dysfunction in children with recurrent otitis media. J. Pediatr. 94:13-8 (1979).
Hanage, et al. Invasiveness of Serotypes and Clones of *Streptococcus pneumoniae* among Children in Finland. Infect. Immun. 73(1): 431-5 (2005).
Henrichsen, et al. Six newly recognized types of *Streptococcus pneumoniae*. J. Clin. Microbiol. 33(10): 2759-2762 (1995).
Huo, et al. Antibody response to pneumolysin and to pneumococcal capsular polysaccharide in healthy individuals and *Streptococcus pneumoniae* infected patients. Vaccine, 22(9-10)1157-61 (2004).
Jeffries, et al. Presence of Nonhemolytic Pneumolysin in Serotypes of *Streptococcus pneumoniae* Associated with Disease Outbreaks. J. Infect. Dis. 196(6): 936-44 (2007).
Kerr, et al. Role of inflammatory mediators in resistance and susceptibility to pneumococcal infection. Infect. Immun. 70(3):1547-57 (2002).
Klein, D.L. Pneumococcal disease and the role of conjugate vaccines. Microb. Drug Resist. 5, 147-157 (1999).
Lagos, R. Population-based surveillance for hospitalized and ambulatory pediatric invasive pneumococcal disease in Santiago, Chile. Ped. Infect. Dis. J. 21(12): 1115-23 (2002).
Lock, et al. Comparative efficacy of pneumococcal neuraminidase and pneumolysin as immunogens protective against *Streptococcus pneumoniae*. Microb. Pathog. 5(6):461-7 (1998).
Lu, et al. Protection against Pneumococcal colonization and fatal pneumonia by a trivalent conjugate of a fusion protein with the cell wall polysaccharide. Infect. Immun. 77(5):2076-83 (2009).

(56) References Cited

OTHER PUBLICATIONS

Malley, et al. Recognition of pneumolysin by Toll-like receptor 4 confers resistance to pneumococcal infection. PNAS USA, 100(4): 1966-71 (2003).
Mendez, et al. Potentiation of the immune response to non-adsorbed antigens by aluminum containing adjuvants. Vaccine, 25(5):825-33 (2007).
Michelow, et al. Epidemiology and clinical characteristics of community-acquired pneumonia in hospitalized children. Pediatrics, 113(4):701-7 (2004).
Michon, et al. Multivalent pneumococcal capsular polysaccharide conjugate vaccines employing genetically detoxified pneumolysin as a carrier protein. Vaccine, 16(18):1732-41 (1998).
Mosmann, et al. TH1 and TH2 cells: different patterns of lymphokine secretion lead to different functional properties. Annu. Rev. Immunol. 7:145-73 (1989).
Obaro, S. Prospects for pneumococcal vaccination in African children. Acta Trop. 75(2):141-53 (2000).
Ogunniyi, et al. Immunization of mice with combinations of pneumococcal virulence proteins elicits enhanced protection against challenge with *Streptococcus pneumoniae*. Infect. Immun. 68(5):3028-33 (2000).
Ogunniyi, et al. Protection against *Streptococcus pneumoniae* elicited by immunization with pneumolysin and CbpA. Infect. Immun. 69(10):5997-6003 (2001).
Oloo, et al. Structure-guided antigen engineering yields pneumolysin mutants suitable for vaccination against pneumococcal disease. J. Biol. Chem. 286(14): 12133-12140 (2011).
Paton, et al. Effect of immunization with pneumolysin on survival time of mice challenged with *Streptococcus pneumoniae*. Infect. Immun. 40(2):548-52 (1983).
Paton, et al. Purification and immunogenicity of genetically obtained pneumolysin toxoids and their conjugation to *Streptococcus pneumoniae* type 19F polysaccharide. Infect. Immun. 59(7):2297-304 (1991).
Paton, et al. Molecular analysis of the pathogenicity of *Streptococcus pneumoniae*: the role of pneumococcal proteins. Annu. Rev. Microbiol. 47:89-115 (1993).
Rahav, et al. Invasive pneumococcal infection: A comparison between adults and children. Medicine 76, 295:303 (1997).
Rubins, et al. Pneumolysin in pneumococcal adherence and colonization. Microb. Pathog. 25(6):337-42 (1998).
Rudan, et al. Global estimate of the incidence of clinical pneumonia among children under five years of age. Bulletin of World Health Organization, 82(12): 895-903 (2004).
Siber, et al. Pneumococcal Vaccines: The Impact of Conjugate Vaccine. JAMA, 301(6): 673-4 (2008).
Snapper, et al. Distinct types of T-cell help for the induction of a humoral immune response to *Streptococcus pneumoniae*. Trends Immunol. 22(6):308-11 (2001).
Veenhoven, et al. Immunoglobulins in otitis-prone children. Pediatr. Res. 55:159-62 (2004).
World Health Organization, Guidelines on nonclinical evaluations vaccines. Technical report series No. 927 (2005).
World Health Organization, Pneumococcal conjugate vaccine for childhood immunization—WHO position paper. Wkly Epidemio. Rec. 82, 93-104 (2007).
Chang, et al. Recent Research on *Streptococcus pneumoniae* in the Pathogenesis, the Prevention and the Treatment of Otitis Media. Otolaryngology Foreign Med. Sci. 18(8): 162 (1994).
Cripps, et al, Bacterial otitis media: a vaccine preventable disease? Vaccine, 23: 2304-2310 (2005).
Kalm, et al. Antibody Activity in Children with and without Otitis Media Tendency before and after Inoculation of *Streptococcus pneumoniae* Vaccine. Acta Otolaryngol. 101(5-6): 467-474 (1986).
Kaur, et al. Serum antibody response to five *Streptococcus pneumoniae* proteins during acute otitis media in otitis-prone and non-otitis-prone children. Pedatr. Infect. Dis, J. 30: 645-650 (2011).
Sharma, et al. Reduced Memory CD4_T-Cell Generation in the Circulation of Young Children May Contribute to the Otitis-Prone Condition. J. Infect. Dis. 204: 645-53 (2011).
Xu, et al. Otitis-prone Children Have Immunologic Deficiencies in Naturally Acquired Nasopharyngeal Mucosal Antibody Response after *Streptococcus pneumoniae* Colonization. Pediatr. Infec. Dis. J. 35: 54-60 (2016).

\* cited by examiner

Figure 6
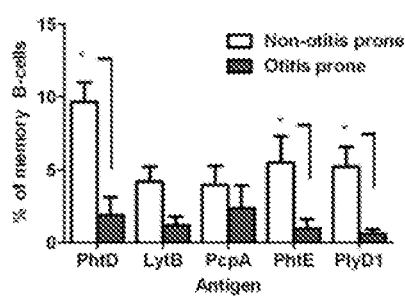
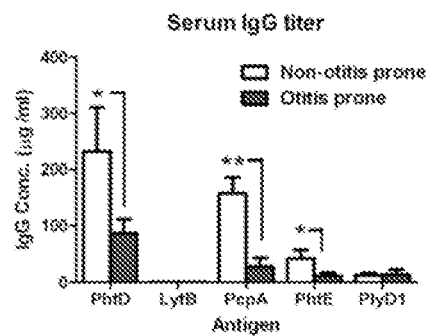
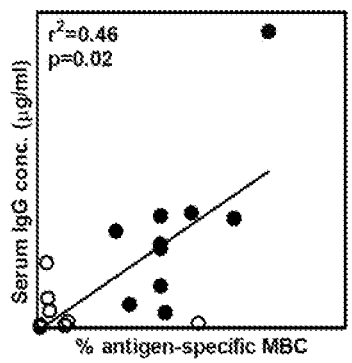

COMPOSITION FOR IMMUNIZATION AGAINST *STREPTOCOCCUS PNEUMONIAE*

RELATED APPLICATIONS

This application was filed under 35 U.S.C. § 371, and claims priority to International Application No. PCT/US2011/063132, filed Dec. 2, 2011, which claims priority to U.S. Ser. No. 61/510,620 filed Jul.22, 2011 and U.S. Ser. No. 61/419,635 filed Dec. 3, 2010, each of which are incorporated herein by reference in their entirety.

FIELD OF THE DISCLOSURE

This disclosure relates to the field of immunology and in particular, to methods of immunization against *Streptococcus pneumoniae*.

BACKGROUND

Otitis media is a common disease in children. The term "otitis media" encompasses a number of clinical disorders including myringitis, otitis media with effusion (OME), chronic suppurative otitis media and acute otitis media (AOM) (24). Acute otitis media (AOM) is a symptomatic illness associated with upper respiratory symptoms, pain, fever and otorrhea. It is the most common infectious disease worldwide, leading to excessive antibiotic consumption in children in most countries and to a substantial burden of deafness and other complications in the developing countries (1-3).

AOM is fairly common and about 60-70% of children experience at least one episode of AOM during the first 3 years of their life (4,5). A subpopulation of children experience recurrent otitis media. Those who experience 3 or more episodes of AOM within 6 months or 4 infections within a year are considered otitis-prone, and represent 10-30% of the total population of children (4;5).

Nasopharyngeal (NP) colonization with one or more otopathogens is a necessary precedent to the development of AOM. *Streptococcus pneumoniae* (Spn), non-typeable *Haemophilia influenzae* (NTHi) and *Moraxella Catarrhalis* are the most common otopathogens causing AOM, and of these three, Spn predominates (6). A direct relationship between frequency of colonization with NTHi and the frequency of AOM has been noted (J. Infect Dis 170:862-866).

Recurrent AOM is currently treated with different antibiotics of escalating strength on the presumption that the recurrent infections are caused by increasingly antibiotic-resistant bacteria. When recurrences occur at a frequency of 3 in 6 months or 4 in 12 months, then tymnpanostomy tube surgery is often performed, with or without concurrent adenoidectomy and/or tonsillectomy.

In regards to prophylactic measures, at present, there are two available types of pneumococcal vaccines. The first includes capsular polysaccharides from 23 types of *S. pneumoniae*, which together represent the capsular types of about 90% of strains causing pneumococcal infection. This vaccine, however, is not very immunogenic in young children (Fedson, and Musher 2004, "Pneumococcal Polysaccharide Vaccine", pp. 529-588; In Vaccines. S. A. Plotikin and W. A. Orenstein (eds.), W.B. Saunders and Co., Philadelphia, Pa.; Shapiro et. al., N. Engl. J. Med. 325:1453-1460 (1991)) as they do not generate a good immune response to polysaccharide antigens prior to 2 years of age. This vaccine is not recommended for the prevention of otitis media.

Conjugate vaccines represent the second available type of pneumococcal vaccine. These vaccines which include serotype specific capsular polysaccharide antigens conjugated to a protein carrier, elicit serotype-specific protection. Currently available are 7-valent and 13-valent conjugate vaccines: the 7-valent includes 7 polysaccharide antigens (derived from the capsules of serotypes 4, 6B, 9V, 14, 18C, 19F and 23F) and the 13-valent conjugate includes 13 polysaccharide antigens (derived from the capsules of serotypes 1, 3, 5, 6A, 7F, and 19A, plus those covered by the 7-valent). 9-valent and 11-valent conjugate vaccines have also been developed and each includes serotype-specific polysaccharides in addition to those in the 7-valent serotypes 1 and 5 in the 9-valent and types 3 and 7F in the 11-valent).

There are however limitations to conjugate vaccines. For example, as such vaccines elicit serotype-specific protection, to protect against additional serotypes of *Streptococcus pneumoniae* including those that dominate in the developing world, additional serotype-specific polysaccharides must be included which increases the difficulty of manufacture (Di Fabio et al., Pediatr. Infect. Dis. J. 20:959-967 (2001); Mulholland, Trop. Med. Int. Health 10:497-500 (2005)). The use of the 7-valent conjugate vaccine has also led to an increase in colonization and disease with strains of capsule types not covered by the polysaccharides included in the vaccine (Bogaert et al., Lancet Infect. Dis. 4:144-154 (2004); Eskola et al., N. Engl. J. Med. 344-403-409 (2001); Mbelle et al., J. Infect. Dis. 180:1171-1176 (1999)). As for pneumococcal otitis media, the available conjugate vaccines do not work as well in protecting against the disease as they do to against invasive disease. In addition, AOM recurrences are still possible following vaccination; for example, the subpopulation of children who are particularly prone to recurrent episodes of AOM, experience a number of recurrences and go on to become otitis prone, despite conjugate immunization.

Therefore, there is still a need for compositions for use in, and methods of, preventing or treating recurring pneumococcal AOM.

SUMMARY OF THE DISCLOSURE

Methods for preventing or treating a recurrence of AOM resulting from an *S. pneumoniae* infection in a subject at risk are described. A subject at risk includes for example, infants and children who have recurrent episodes of AOM (e.g., otitis prone) and those who have had AOM treatment failure. For example, methods of preventing or treating a recurrence of acute otitis media resulting from a *Streptococcus pneumoniae* infection in a subject at risk of developing a pneumococcal AOM reoccurrence, the method comprising administering at least once to said subject, a therapeutically effective amount of a composition comprising at least one isolated and purified immunogenic polypeptide selected from the group consisting of *Streptococcus pneumoniae* PhtD, PhtE, PcpA, LytB and detoxified pneumolysin, or an immunogenic fragment thereof, are provided. In certain embodiments, the subject may have previously experienced at least one episode of acute otitis media. In some embodiments, the subject may have experienced 3 or more episodes of acute otitis media within a period of six months or has experienced 4 or more episodes of acute otitis media within a period of 12 months. In some embodiments, the subject may have acute otitis media.

Compositions for use in these methods, in preventing or treating a recurrence of AOM are also described. The compositions comprise at least one immunogenic polypeptide of *S. pneumoniae* selected from the group consisting of PhtD, PhtE, PcpA, LytB, and detoxified pneumolysin, or immunogenic fragments thereof.

The subject matter disclosed herein provides several advantages. For example, the methods described herein can be used to elicit or enhance the production of antigen specific CD4+ T-cells.

Other features and advantages will be apparent from the following Detailed Description, the Drawings and the Claims.

BRIEF DESCRIPTION OF THE DRAWINGS

The disclosure may be further understood from the following description with reference to the drawings.

FIG. 6. Are graphical representations consisting of panels A, B and C: FIG. 6A shows percent frequencies of antigen-specific memory B cells; FIG. 6B shows a comparison of IgG responses to five pneumococcal antigens in the serum samples of non-otitis-prone and otitis-prone children (Y-axis represents Geometric mean titers and error bars are upper 95% confidence intervals); FIG. 6C shows the correlation between the percentage of circulating PhtD-specific memory B-cells (x-axis) with serum PhtD-specific IgG concentration (y-axis).

DETAILED DESCRIPTION

Figure 1:
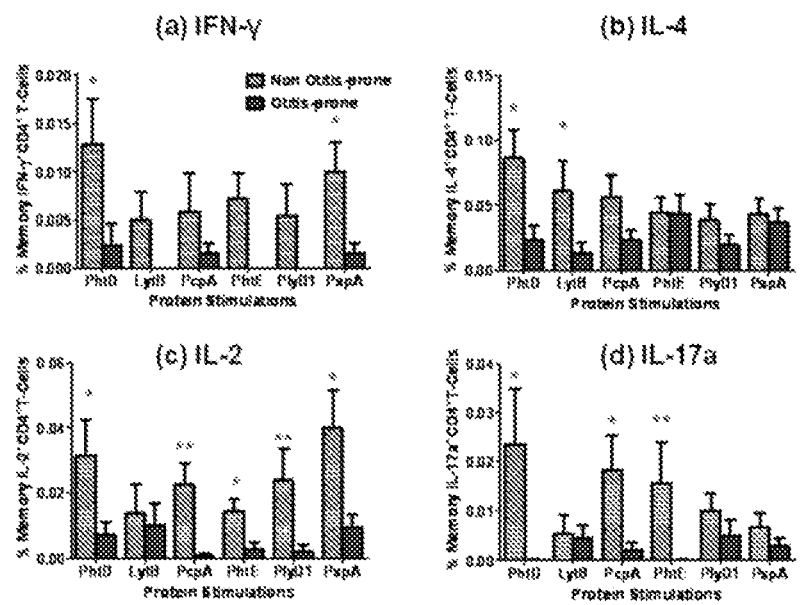
FIG. 1. Is a graphical representation showing percent frequencies of CD45RALow memory CD4+ T-cell subsets producing various cytokines against six pneumococcal antigens (a) IFN-γ, (b) IL-4, (c) IL-2 & (d) IL-17a, in the circulation of non otitis-prone and otitis-prone children against various pneumococcal antigens. Bar graphs represent mean percentage values of CD69+ CD4+ T-cells, following antigen stimulations. Error bars represent. SEM, P values were calculated using Mann Whitney test. *$P<0.05$; **$P<0.005$.

Methods for preventing and/or treating a recurrence of acute otitis media resulting from an *S. pneumoniae* infection in a subject at risk (e.g., a child) are described. Compositions for use in these methods, in preventing and/or treating a recurrence of acute otitis media are also described. The compositions comprise at least one immunogenic polypeptide of *S. pneumoniae* selected from the group consisting of PhtD, PhtE, PcpA, LytB, and detoxified pneumolysin, or immunogenic fragments thereof. These methods and compositions are described further, below.

The prophylactic and therapeutic methods provided comprise the administration of a therapeutically effective amount of a composition (e.g., a pharmaceutical composition), at least once, comprising at least one isolated and purified immunogenic polypeptide of *S. pneumoniae* selected from the group consisting of PhtD, PhtE, PcpA, LytB, and detoxified pneumolysin, or an immunogenic fragment thereof, to subjects at risk of developing a pneumococcal AOM recurrence (i.e., a symptomatic *S. pneumoniae* infection resulting in an AOM recurrence).

The population of subjects at risk include, for example, infants and children that have had at least one, two, three, four or more AOM episodes in their lifetime; infants and children who are otitis prone (i.e., who have had 3 or more episodes of AOM within 6 months or 4 or more episodes of AOM within a year); and infants and children that have or who have had AOM treatment failure (i.e., those with AOM that have failed to achieve bacterial eradication and/or resolution of symptoms after at least 48 hours of appropriate antibiotic therapy; or infants and children whose signs and symptoms of AOM returned within 14 days of completing an antibiotic treatment course). The population of subjects at risk also includes for example, infants and children: with a genetic propensity for recurrent AOM (Casselbrant M L et al JAMA 1999; 282:2125-2130); attending day care outside the home; attending family day care; with one or more parents/caregivers who smoke; using a pacifier; formula rather than breast fed; and who have experienced an AOM infection in the first 6 months of life (Bentdal et al Int. J. Ped. Otorhinolaryngol. 2007; 71:1251-1259). As children age, they become less prone to AOM because of anatomical changes in the eustachion tube. Usually, the otitis prone child "outgrows" their propensity around age 3 to 5 years (40;48-51). En certain embodiments, the subject has, or is at risk of developing, pneumococcal AOM.

As discussed in the Examples herein, otitis prone children (i.e., a population of subjects at risk) as compared to non-otitis prone children display immunological hyporesponsiveness against Spn antigens (e.g., PhtD, PhtE, PcpA, LytB, Ply). For example, as compared to non-otitis prone children, otitis prone children have a lack or reduction of pneumococcal antigen specific functional memory CD4+ T-cells (c.a., functional memory CD4+ T-cells specific for PhtD, PhtE, PcpA, LytB, or Ply) and reduced scrum IgG levels to pneumococcal antigens (e.g., to PhtD, PhtE, PcpA, LytB, Ply). These children are not however deficient in total functional memory T-cells or in eliciting B cell mediated antibody responses against vaccinated antigens. Children with AOM treatment failure (AOMTF) behave immunologically similar to otitis prone children. Subjects at risk are those who display such immunological hyporesponsiveness against Spn antigens such as for example, PhtD, PhtE, PcpA, LytB and/or Ply.

As used herein, preventing a recurrence of AOM in a subject is intended to mean administration of a therapeutically effective amount of a composition described herein to a subject in order to protect the subject from the development of a recurrence of pneumococcal acute otitis media.

As used herein, treating a recurrence of AOM (or an otitis prone subject or a subject with recurring AOM) is intended to mean administration of a therapeutically effective amount of a composition described herein to a subject that is afflicted with AOM caused by *S. pneumoniae* or that has been exposed to *S. pneumoniae*, and was previously afflicted with AOM, where the purpose is to cure, heal, alleviate, relieve, alter, remedy, ameliorate, improve, or affect the condition (e.g., AOM) or the symptoms of the disease (i.e., AOM).

A therapeutically effective amount refers to an amount that provides a therapeutic effect for a given condition and administration regimen. A therapeutically effective amount can be determined by the ordinary skilled medical worker based on patient characteristics (age, weight, gender, condition, complications other diseases etc.). The therapeutically effective amount will be further influenced by the route of administration of the composition.

In certain examples, the administration of the composition elicits or enhances the production of antigen specific CD4+ T-cells. The antigen specific CD4+ T-cells whose production is elicited or enhanced may be those that produce the cytokines IFN-γ, IL-4, IL-2 and/or IL-17a, for example. For example, in one embodiment, administration of the composition elicits or enhances the production of antigen specific CD4+ T-cells that produce IFN-γ. As used herein, "elicits or enhances the production of antigen specific CD4+ T-cells" is intended to mean that the quantity or percentage (%) of the antigen specific CD4+ T-cells is increased. The quantity of cells may increase by, for example, 25%, 30%, 35%, 45%, 50%, 55%, 60%, 65%, 70%, 75%, 80%, 85%, 90%, 95%, 100%, 150%, 200%, 300%, 400% or more over the quantity of cells existing immediately before the administration of the composition.

In one embodiment, the administration of the composition elicits or enhances antigen specific antibody (e.g., IgG) production. By eliciting or enhancing antibody production, the total concentration (titer) of antigen specific total IgG is increased relative to the concentration (titer) existing immediately before administration. The end point dilution titer may increase by, for example, 25%, 30%, 35%, 40%, 45%, 50%, 55%, 60%, 65%, 70%, 75%, 80%, 85%, 90%, 95%, 100%, 150%, 200% or more over the titer existing immediately before the administration of the composition. In one embodiment, the antigen specific IgG titer is increased, for example, 2, 3, or 4 fold relative to the titer existing immediately before the administration of the composition.

Also disclosed, is a method of reducing the risk of an acute otitis media recurrence in a subject at risk (e.g., a child) comprising administering to the subject a composition comprising one or more of the disclosed immunogenic polypeptides. The risk of such a recurrence may be reduced by the methods described herein.

In particular embodiments, a method of preventing or treating the otitis prone condition in a subject at risk (i.e., a subject who has had at least one or more recurring episodes of AOM) is provided.

The present disclosure also provides methods of eliciting an immune response in a subject at risk by administering the compositions described herein. This may be achieved by the administration of a pharmaceutically acceptable formulation of the composition to the subject to effect exposure of the at least one immunogenic polypeptide to the immune system of the subject.

This disclosure also provides for the use of one or more immunogenic *S. pneumoniae* polypeptides in compositions such as, for example, vaccine compositions. Such a composition upon administration to a subject (e.g., a mammal), induces or enhances an immune response directed against the immunogenic polypeptide (i.e., antigen) included in the composition. This response may include the generation of antibodies (e.g, through the stimulation of B cells) or a T cell-based response (e.g., a cytolytic response). These responses may or may not be protective or neutralizing. A protective or neutralizing immune response is one that is detrimental to the infectious organism corresponding to the antigen (e.g., from which the antigen was derived) and beneficial to the subject (e.g., by reducing or preventing infection). As used herein, protective or neutralizing antibodies may be reactive to the corresponding wild-type *S. pneumoniae* polypeptide and may reduce or inhibit the lethality of the corresponding *S. pneumoniae* organism or of the corresponding wild-type *S. pneumoniae* polypeptide when tested in subjects (e.g., mammals). An immunological composition that, upon administration to a subject, results in a protective or neutralizing immune response may be considered a vaccine. The compositions described herein find use in methods of preventing or treating an AOM recurrence in a subject at risk, whom as defined above is at risk of being infected with *S. pneumoniae* and developing an AOM recurrence. The composition also finds use in methods of preventing or treating recurring AOM.

The compositions described herein can be administered by an appropriate route such as for example, percutaneous (e.g., intramuscular, intravenous, intraperitoneal or subcutaneous), transdermal, mucosal (e.g., intranasal) or topical, in amounts and in regimes determined to be appropriate by one skilled in the art. For example, 100 ng-500 μg, 1-240 μg, 10-100 μg, 5-50 μg, or 10-25 μg of the immunogenic polypeptide can be administered per dose. For the purposes of prophylaxis or therapy, the vaccine can be administered once or multiple times. For example, the vaccine can be administered 1, 2, 3, or 4 times, for example. In one example, the one or more administrations may occur as part of a so-called "prime-boost" protocol. When multiple doses are administered, the doses can be separated from one another by, for example, one week, one month or several months.

The immunogenic polypeptides described herein have immunogenic activity. The term "immunogenic activity" refers to the ability of a polypeptide to elicit an immunological response in a subject (e.g., a mammal). An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells and/or cytotoxic T cells, directed to an epitope or epitopes of the polypeptide. The term "epitope" refers to the site on an antigen to which specific B cells and/or T cells respond so that antibody is produced. The immunogenic activity may be protective. The term "protective immunogenic activity" refers to the ability of a polypeptide to elicit an immunological response in a subject that prevents or inhibits infection by *S. pneumoniae* (e.g., inhibits an infection by *S. pneumoniae* resulting in a recurrence of AOM).

In certain embodiments, a multi-component composition comprising two, three, four or more immunogenic polypeptides may be formulated to protect against a recurrence of AOM resulting from an *S. pneumoniae* infection. A preferred embodiment of such a composition comprises immunogenic polypeptides of PhtD and PcpA. A further preferred composition comprises immunogenic polypeptides of PhtD, PcpA and detoxified pneumolysin. Certain preferred multi-component compositions for use as described herein are described in WO2011/075823 (filed on 20 Dec. 2010 and entitled, Immunogenic Compositions).

The components of a multi-component composition preferably are compatible and are combined in appropriate ratios to avoid antigenic interference and to optimize any possible synergies. For example the amounts of each component can be in the range of about 5 µg to about 500 µg per dose, 5 µg to about 10 µg per dose, 25 µg to about 50 µg per dose or 50 µg to about 100 µg per dose. Most preferably, the range can be about 10 µg to 50 µg per antigenic component per dose.

Immunogenic Polypeptides

The nucleic acids encoding the immunogenic polypeptides may be isolated for example, but without limitation from wild type or mutant *S. pneumoniae* cells or alternatively, may be obtained directly from the DNA of an *S. pneumoniae* strain carrying the applicable DNA gene sequence (e.g., pcpA or phtD), by using the polymerase chain reaction (PCR) or by using alternative standard techniques that are recognized by one skilled in the art. Possible strains of use include for example *S. pneumoniae* strains TIGR4 and 14453. In preferred embodiments the polypeptides are recombinantly derived from *S. pneumoniae* strain 14453.

The polypeptides described herein can be produced using standard molecular biology techniques and expression systems (see for example, *Molecular Cloning: A Laboratory Manual*, Third Edition by Sambrook et. al., Cold Spring Harbor Press, 2001). For example, a fragment of a gene that encodes an immunogenic polypeptide may be isolated and the polynucleotide encoding the immunogenic polypeptide may be cloned into any commercially available expression vector (such as, e.g., pBR322, and pUC vectors (New England Biolabs, Inc., Ipswich, Mass.)) or expression/purification vectors (such as e.g., GST fusion vectors (Pfizer, Inc., Piscataway, N.J.)) and then expressed in a suitable prokaryotic, viral or eukaryotic host. Purification may then be achieved by conventional means, or in the case of a commercial expression/purification system, in accordance with manufacturer's instructions.

Alternatively, the immunogenic polypeptides described herein, including variants, may be obtained through chemical synthesis using commercially automated procedures, such as for example, exclusive solid phase synthesis, partial solid phase methods, fragment condensation or solution synthesis.

Immunogenic PcpA polypeptides comprise the full-length PcpA amino acid sequence (in the presence or absence of the signal sequence), fragments thereof, and variants thereof. PcpA polypeptides suitable for use in the compositions described herein include, for example, those of GenBank Accession Nos. CAB04758, YP817353, AAK76194, NP359536, ZP01835022, and ZP01833419, and those described herein and in the Examples below, among others. In one embodiment, PcpA has the amino acid sequence shown in SEQ ID NOs: 1 or 2.

The amino acid sequence of full length PcpA in the *S. pneumoniae* 14453 genome is SEQ ID NO. 1. Preferred PcpA polypeptides may comprise an amino acid sequence having 50% or more identity (e.g, 60, 65, 70, 75, 80, 85, 85, 90, 91, 92, 93, 94, 95, 96, 97, 98, 99, 99.5% or more) to SEQ ID NOs: 1, 2 or 3. Preferred polypeptides may comprise a fragment of at least 8, 9, 10, 12, 14, 16, 18, 20, 25, 30, 35, 40, 50, 60, 70, 80, 90, 100, 150, 200, 250 or more, for example, consecutive amino acids of SEQ ID NOs:1, 2 or 3. Preferred fragments comprise an epitope from SEQ ID NOs.1, 2 or 3. Other preferred fragments lack one or more amino acids from the N-terminus of SEQ ID NOs: 1 or 2 (e.g., 1, 2, 3, 4, 5, 6, 7, 8, 9, 10, 15, 20, 25 or more) and/or one or more amino acids from the C-terminus of SEQ ID NOs:1 or 2 while retaining at least one epitope of SEQ ID NOs:1 or 2. Further preferred fragments lack the signal sequence from the N-terminus of SEQ ID NOs: 1 or 2. A preferred PcpA polypeptide is SEQ ID NO: 3.

(PcpA, Spn strain 14453)

SEQ ID NO: 1

MKKTTILSLTTAAVILAAYVPNEPILADTPSSEVIKETKVGSIIQQNNIK
YKVLTVEGNIRTVQVGNGVTPVEFEAGQDGKPFTIPTKITVGDKVFTVTE
VASQAFSYYPDETGRIVVYPSSITIPSSIKKIQKKGFHGSKAKTIIFDKG
SQLEKIEDRAFDFSELEEIELPASLEYIGTSAFSFSQKLKKLTFSSSSKL
ELISHEAFANLSNLEKLTLPKSVKTLGSNLFRLTTSLKHVDVEEGNESFA
SVDGVLFSKDKTQLIYYPSQKNDESYKTPKETKELASYSFNKNSYLKKLE
LNEGLEKIGTFAFADAIKLEEISLPNSLETIERLAFYGNLELKELILPDN
VKNFGKHVMNGLPKLKSLTIGNNINSLPSFFLSGVLDSLKEIHIKNKSTE
FSVKKDTFAIPETVKFYVTSEHIKDVLKSNLSTSNDIIVEKVDNIKQETD
VAKPKKNSNQGVVGWVKDKGLWYYLNESGSMATGWVKDKGLWYYLNESGS
MATGWVKDKGLWYYLNESGSMATGWVKDKGLWYYLNESGSMATGWVKDKG
LWYYLNESGSMATGWVKDKGLWYYLNESGSMATGWVKDKGLWYYLNESGS
MATGWFTVSGKWYYTYNSGDLLVNTTTPDGYRVNANGEWVG (PcpA)

SEQ ID NO: 2

MKKTTILSLTTAAVILAAYVPNEPILAAYVPNEPILADTPSSEVIKETKV
GSIIQQNNIKYKVLTVEGNIGTVQVGNGVTPVEFEAGQDGKPFTIPTKIT
VGDKVFTVTEVASQAFSYYPDETGRIVVYPSSITIPSSIKKIQKKGFHGS
KAKTIIFDKGSQLEKIEDRAFDFSELEEIELPASLEYIGTSAFSFSQKLK
KLTFSSSSKLELISHEAFANLSNLEKLTLPKSVKTLGSNLFRLTTSLNML
MLRGMIVASVDGVSFQSKTQLIYYPSQKNDESYKTPKETKELASYSFNKN
SYLKKLELNEGLQKIGTFAFADATKLEEISLPNSLETIERLAFYGNLELK
ELILPDNVKNFGKHVMNGLPKFLTLSGNNINSLPSFFLSGVLDSLKEIHI
KNKSTEFSVKKDTFAIPETVKFYVTSEHIKDVLKSNLSTSNDIIVEKVDN
IKQETDVAKPKKNSNQGVVGWVKDKGLWYYLNESGSMATGWVKDKGLWYY
LNESGSMATGWVKDKGLWYYLNESGSMATGWVKDKGLWYYLNESGSMATG
WVKDKGLWYYLNESGSMATGWVKDKGLWYYLNESGSMATGWVKDKGLWYY
LNESGSMATGWVKDKGLWYYLNESGSMATGWVKDKGLWYYLNESGSMATG
WVKDKGLWYYLNESGSMATGWVKDKGLWYYLNESGSMATGWFKVSGKWYY
TYNSGDFI (PcpA construct)

SEQ ID NO: 3

MADTPSSEVIKETKVGSIIQQNNIKYKVLTVEGNIGTVQVGNGVTPVEFE
AGQDGKPFTIPTKITVGDKVFTVTEVASQAFSYYPDETGRIVVYPSSITI
PSSIKKIQKKGFHGSKAKTIIFDKGSQLEKIEDRAFDFSELEEIELPASL
EYIGTSAFSFSQKLKKLTFSSSSKLELISHEAFANLSNLEKLTLPKSVKT
LGSNLFRLTTSLKHVDVEEGNESFASVDGVLFSKDKTQLIYYPSQKNDES
YKTPKETKELASYSFNKNSYLKKLELNEGLEKIGTFAFADAIKLEEISLP
NSLETIERLAFYGNLELKELILPDNVKNFGKHVMNGLPKLKSLTIGNNIN
SLPSFFLSGVLDSLKEIHIKNKSTEFSVKKDTFAIPETVKFYVTSEHIKD
VLKSNLSTSNDIIVEKVDNIKQETDVAKPKKNSNQGVVGWVKDKG

An immunogenic polypeptide of PcpA optionally lacks the choline binding domain anchor sequence typically present in the naturally occurring mature PcpA protein. The naturally occurring sequence of the choline binding anchor of the mature PcpA protein is disclosed in WO 2008/022302 as SEQ ID NO:52. More particularly, an immunogenic polypeptide comprises an N-terminal region of naturally occurring PcpA with one or more amino acid substitutions and about 60 to about 99% sequence identity or any identity in between, e.g. 80, 85, 90 and 95% identity, to the naturally occurring PcpA. The N-terminal region may comprise the amino acid sequence of SEQ ID NOs: 1 or 2 (or SEQ ID NOs: 1, 2, 3, 4, 41 or 45 of WO2008/022302), in the presence or absence of one or more conservative amino acid substitutions and in the presence or absence of the signal sequence. The N-terminal region may comprise an amino acid sequence having about 60 to about 99% sequence identity (or any identity in between 80 to 99% identity) to SEQ ID NOs: 1, 2 or 3 (set out in the Sequence Listing herein) or SEQ ID NOs:1, 2, 3, 4, or 41 of WO2008/022302.

Immunogenic fragments of SEQ ID NOs: 1, 2 or 3 may comprise, for example, 5, 10, 20, 30, 40, 50, 60, 70, 80, 90, 100, 110, 120, 130, 140, 150, 160, 170, 180, 190 and 191 amino acid residues of SEQ ID NOs: 1, 2 or 3 or any number of amino acid residues between 5 and 191. Examples of immunogenic fragments of PcpA are disclosed in WO 2008/022302.

Variants of the immunogenic polypeptides described herein may comprise one or more conservative amino acid substitutions. Variants of the immunogenic PcpA polypeptides include amino acid sequence having about 50 to about 99% sequence identity (or any identity in between 50 and 99% identity) to SEQ ID NOs: 1, 2 or 3 or any fragment thereof. Variants are selected for their immunogenic capacity using methods well known in the art.

Immunogenic PhtX polypeptides suitable for the compositions described herein include for example, the full-length PhtD or PhtE amino acid sequence (in the presence or absence of the signal sequence), immunogenic fragments thereof, variants thereof and fusion proteins thereof. PhtD polypeptides suitable for use in the compositions described herein include, for example, those of GenBank Accession Nos. AAK06760, YP816370 and NP35851, among others. The amino acid sequence of full length PhtD in the *S. pneumoniae* 14453 genome is SEQ ID NO: 4 and that from the TIGR4 strain is SEQ ID NO: 5. A preferred polypeptide of PhtD (derived from the *S. pneumoniae* 14453 genome) is SEQ ID NO: 6. PhtE polypeptides suitable for use in the composition described herein include, for example, those of GenBank Accession Nos. AAK06761, YP816371 and NP358502, among others. The amino acid sequence of full length PhtE in the *S. pneumoniae* 14453 genome is SEQ ID NO: 7. A preferred polypeptide of PhtE (derived from the *S. pneumoniae* 14453 genome) is SEQ ID NO: 8.

(PhtD Spn strain 14453)
SEQ ID NO: 4
```
MKINKKYLAGSVAVLALSVCSYELGRHQAGQVKKESNRVSYIDGDQAGQK
AENLTPDEVSKREGINAEQIVIKITDQGYVTSHGDHYHYYNGKVPYDAII
SEELLMKDPNYQLKDSDIVNEIKGGYVIKVDGKYYVYLKDAAHADNIRTK
EEIKRQKQEHSHNHNSRADNAVAAARAQGRYTTDDGYIFNASDIIEDTGD
AYIVPHGDHYHYIPKNELSASELAAAEAYWNGKQGSRPSSSSSYNANPVQ
PRLSENHNLTVTPTYHQNQGENISSLLRELYAKPLSERHVESDGLIFDPA
QITSRTARGVAVPHGNYHFIPYEQMSELEKRIARIIPLRYRSNHWVPDS
RPEQPSPQSTPEPSPSLQPAPNPQPAPSNPIDEKLVKEAVRKVGDGYVFE
ENGVSRYIPAKDLSAETAAGIDSKLAKQESLSHKLGAKKTDLPSSDREFY
NKAYDLLARIHQDLLDNKGRQVDFEVLDNLLERLKDVSSDKVKLVDDILA
FLAPIRHPERLGKPNAQITYTDDEIQVAKLAGKYTTEDGYIFDPRDITSD
EGDAYVTPHMTHSHWIKKDSLSEAERAAAQAYAKEKGLTPPSTDHQDSGN
TEAKGAEAIYNRVKAAKKVPLDRMPYNLQYTVEVKNGSLIIPHYDHYHNI
KFEWFDEGLYEAPKGYSLEDLLATVKYYVEHPNERPHSDNGFGNASDHVR
KNKADQDSKPDEDKEHDEVSEPTHPESDEKENHAGLNPSADNLYKPSTDT
EETEEEAEDTTDEAEIPQVENSVINAKIADAEALLEKVTDPSIRQNAMET
LTGLKSSLLLGTKDNNTISAEVDSLLALLKESQPAPIQ
```

(PhtD Spn strain TIGR4)
SEQ ID NO: 5
```
MKINKKYLAGSVAVLALSVCSYELGRHQAGQVKKESNRVSYIDGDQAGQK
AENLTPDEVSKREGINAEQIVIKITDQGYVTSHGDHYHYYNGKVPYDAII
SEELLMKDPNYQLKDSDIVNEIKGGYVIKVDGKYYVYLKDAAHADNIRTK
EEIKRQKQEHSHNHGGGSNDQAVVAARAQGRYTTDDGYIFNASDIIEDTG
DAYIVPHGDHYHYIPKNELSASELAAAEAYWNGKQGSRPSSSSSYNANPA
QPRLSENHNLTVTPTYHQNQGENISSLLRELYAKPLSERHVESDGLIFDP
```
-continued
```
AQITSRTARGVAVPHGNHYHFIPYEQMSELEKRIARIIPLRYRSNHWVPD
SRPEQPSPQSTPEPSPSPQPAPNPQPAPSNPIDEKLVKEAVRKVGDGYVF
EENGVSRYIPAKDLSAETAAGIDSKLAKQESLSHKLGAKKTDLPSSDREF
YNKAYDLLARIHQDLLDNKGRQVDFEALDNLLERLKDVPSDKVKLVDDIL
AFLAPIRHPERLGKPNAQITYTDDEIQVAKLAGKYTTEDGYIFDPRDITS
DEGDAYVTPHMTHSHWIKKDSLSEAERAAAQAYAKEKGLTPPSTDHgDSG
NTEAKGAEAIYNRVKAAKKVPLDRMPYNLQYTVEVKNGSLIIPHYDHYHN
IKFEWFDEGLYEAPKGYTLEDLLATVKYYVEHPNERPHSDNGFGNASDHV
RKNKVDQDSKPDEDKEHDEVSEPTHPESDEKENHAGLNPSADNLYKPSTD
TEETEEEAEDTTDEAEIPQVENSVINAKIADAEALLEKVTDPSIRQNAME
TLTGLKSSLLLGTKDNNTISAEVDSLLALLKESQPAPIQ
```

(PhtD construct derived from Spn strain 14453)
SEQ ID NO: 6
```
MGSYELGRHQAGQVKKESNRVSYIDGDQAGQKAENLTPDEVSKREGINAE
QIVIKITDQGYVTSHGDHYHYYNGKVPYDAIISEELLMKDPNYQLKDSDI
VNEIKGGYVIKVDGKYYVYLKDAAHADNIRTKEEIKRQKQEHSHNHNSRA
DNAVAAARAQGRYTTDDGYIFNASDIIEDTGDAYIVPHGDHYHYIPKNEL
SASELAAAEAYWNGKQGSRPSSSSSYNANPVQPRLSENHNLTVTPTYHQN
QGENISSLLRELYAKPLSERHVESDGLIFDPAQITSRTARGVAVPHGNHY
HFIPYEQMSELEKRIARIIPLRYRSNHWVPDSRPEQPSPQSTPEPSPSLQ
PAPNPQPAPSNPIDEKLVKEAVRKVGDGYVFEENGVSRYIPAKDLSAETA
AGIDSKLAKQESLSHKLGAKKTDLPSSDREFYNKAYDLLARIHQDLLDNK
GRQVDFEVLDNLLERLKDVSSDKVKLVDDILAFLAPIRHPERLGKPNAQI
TYTDDEIQVAKLAGKYTTEDGYIFDPRDITSDEGDAYVTPHMTHSHWIKK
DSLSEAERAAAQAYAKEKGLTPPSTDHQDSGNTEAKGAEAIYNRVKAAKK
VPLDRMPYNLQYTVEVKNGSLIIPHYDHYHNIKFEWFDEGLYEAPKGYSL
EDLLATVKYYVEHPNERPHSDNGFGNASDHVRKNKADQDSKPDEDKEHDE
VSEPTHPESDEKENHAGLNPSADNLYKPSTDTEETEEEAEDTTDEAEIPQ
VENSVINAKIADAEALLEKVTDPSIRQNAMETLTGLKSSLLLGTKDNNTI
SAEVDSLLALLKESQPAPIQ
```

(PhtE)
SEQ ID NO: 7
```
MKFSKKYIAAGSAVIVSLSLCAYALNQHRSQENKDNNRVSYVDGSQSSQK
SENLTPDQVSQKEGIQAEQIVIKITDQGYVTSHGDHYHYYNGKVPYDALF
SEELLMKDPNYQLKDADIVNEVKGGYIIKVDGKYYVYLKDAAHADNVRTK
DEINRQKQEHVKDNEKVNSNVAVARSQGRYTTNDGYVFNPADIIEDTGNA
YIVPHGGHYHYIPKSDLSASELAAAKAHLAGKNMQPSQLSYSSTASDNNT
QSVAKGSTSKPANKSENLQSLLKELYDSPSAQRYSESDGLVFDPAKIISR
TPNGVAIPHGDHYHFIPYSKLSALEEKIARMVPISGTGSTVSTNAKPNEV
VSSLGSLSSNPSSLTTSKELSSASDGYIFNPKDIVEETATAYIVRHGDHF
HYIPKSNQIGQPTLPNNSLATPSPSLPINPGTSHEKHEEDGYGFDANRII
AEDESGFVMSHGDHNHYFFKKDLTEEQIKAAQKHLEEVKTSHNGLDSLSS
HEQDYPSNAKEMKDLDKKIEEKIAGIMKQYGVKRESIVVNKEKNAIIYPH
GDHHHADPIDEHKPVGIGHSHSNYELFKPEEGVAKKEGNKVYTGEELTNV
VNLLKNSTFNNQNFTLANGQKRVSFSFPPELEKKLGINMLVKLITPDGKV
LEKVSGKVFGEGVGNIANFELDQPYLPGQTFKYTIASKDYPEVSYDGTFT
VPTSLAYKMASQTIFYPFHAGDTYLRVNPQFAVPKGTDALVRVFDEFHGN
AYLENNYKVGEIKLPIPKLNQGTTRTAGNKIPVTFMANAYLDNQSTYIVE
VPILEKENQTDKPSILPQFKRNKAQENLKLDEKVEEPKTSEKVEKEKLSE
TGNSTSNSTLEEVPTVDPVQEKVAKFAESYGMKLENVLFNMDGTIELYLP
SGEVIKKNMADFTGEAPQGNGENKPSENGKVSTGTVENQPTENKPADSLP
EAPNEKPVKPENSTDNGMLNPEGNVGSDPMLDPALEEAPAVDPVQEKLEK
FTASYGLGLDSVIFNMDGTIELRLPSGEVIKKNLSDLIA
```

(PhtE construct derived from Spn strain 14453)
SEQ ID NO: 8
```
MGKNMQPSQLSYSSTASDNNTQSVAKGSTSKPANKSENLQSLLKELYDSP
SAQRYSESDGLVFDPAKIISRTPNGVAIPHGDHYHFIPYSKLSALEEKIA
RMVPISGTGSTVSTNAKPNEVVSSLGSLSSNPSSLTTSKELSSASDGYIF
NPKDIVEETATAYIVRHGDHFHYIPKSNQIGQPTLPNNSLATPSPSLPIN
PGTSHEKHEEDGYGFDANRIIAEDESGFVMSHGDHNHYFFKKDLTEEQIK
AAQKHLEEVKTSHNGLDSLSSHEQDYPGNAKEMKDLDKKIEEKIAGIMKQ
YGVKRESIVVNKEKNAIIYPHGDHHHADPIDEHKPVGIGHSHSNYELFKP
EEGVAKKEGNKVYTGEELTNVVNLLKNSTFNNQNFTLANGQKRVSFSFPP
ELEKKLGINMLVKLITPDGKVLEKVSGKVFGEGVGNIANFELDyPYLPGQ
TFKYTIASKDYPEVSYDGTFTVPTSLAYKMASQTIFYPFHAGDTYLRVNP
QFAVPKGTDALVRVFDEFHGNAYLENNYKVGEIKLPIPKLNQGTTRTAGN
KIPVTFMANAYLDNQSTYIVEVPILEKENQTDKPSILPQFKRNKAQENSK
LDEKVEEPKTSEKVEKEKLSETGNSTSNSTLEEVPTVDPVQEKVAKFAES
YGMKLENVLFNMDGTIELYLPSGEVIKKNMADFTGEAPQGNGENKPSENG
KVSTGTVENQPTENKPADSLPEAPNEKPVKPENSTDNGMLNPEGNVGSDP
MLDPALEEAPAVDPVQEKLEKFTASYGLGL
```

Immunogenic PhtX (e.g., PhtD or PhtE) polypeptides may include the full length protein with the signal sequence attached, the mature full length protein with the signal peptide (e.g., about 20 amino acids at N-terminus) removed, variants of PhtX (naturally occurring or otherwise, e.g., synthetically derived) and immunogenic fragments of PhtX (e.g., fragments comprising at least 15 or 20 contiguous amino acids present in the naturally occurring mature PhtX protein). The immunogenic fragments and variants of PhtX polypeptides are capable of eliciting an immune response specific for the corresponding full length mature amino acid sequence. Examples of immunogenic fragments of PhtD are disclosed in PCT publication WO2009/012588.

Preferred PhtD polypeptides for use may comprise an amino acid sequence having 50% or more identity (e.g., 60, 65, 70, 75, 80, 85, 85, 90, 91, 92, 93, 94, 95, 96, 97, 98, 99, 99.5% or more) to SEQ ID NO:4, 5 or 6. Preferred polypeptides for use may comprise a fragment of at least 8, 9, 10, 12, 14, 16, 18, 20, 25, 30, 35, 40, 50, 60, 70, 80, 90, 100, 150, 200, 250 or more consecutive amino acids of SEQ ID NO:4, 5 or 6. Preferred fragments comprise an epitope from SEQ ID NO: 4, 5 or 6. Other preferred fragments lack one or more amino acids from the N-terminus of SEQ ID NO: 4, 5 or 6 (e.g., 1, 2, 3, 4, 5, 6, 7, 8, 9, 10, 15, 20, 25 or more) and/or one or amino acids from the C-terminus of SEQ ID NO: 4, 5 or 6 while retaining at least one epitope of SEQ ID NO: 4, 5 or 6. Further preferred fragments lack the signal sequence from the N-terminus of SEQ ID NO: 4 or 5. A preferred PhtD polypeptide is SEQ ID NO: 6.

Preferred PhtE polypeptides for use may comprise an amino acid sequence having 50% or more identity (e.g., 60, 65, 70, 75, 80, 85, 85, 90, 91, 92, 93, 94, 95, 96, 97, 98, 99, 99.5% or more) to SEQ ID NO:7 or to SEQ ID NO:8. Preferred polypeptides for use may comprise a fragment of at least 8, 9, 10, 12, 14, 16, 18, 20, 25, 30, 35, 40, 50, 60, 70, 80, 90, 100, 150, 200, 250 or more consecutive amino acids of SEQ ID NO: 7 or 8. Preferred fragments comprise an epitope from SEQ ID NO.7 or to SEQ ID NO: 8. Other preferred fragments lack one or more amino acids from the N-terminus of SEQ ID NO. 7 or 8 (e.g., 1, 2, 3, 4, 5, 6, 7, 8, 9, 10, 15, 20, 25 or more) and/or one or amino acids from the C-terminus of SEQ ID NO:7 or 8 while retaining at least one epitope of SEQ ID NO:7 or 8. Further preferred fragments lack the signal sequence from the N-terminus of SEQ ID NO:7. A preferred PhtE polypeptide is SEQ ID NO:8.

Immunogenic LytB polypeptides include the full length protein with the signal sequence attached, the mature full length protein with the signal peptide removed, variants of LytB (naturally occurring or otherwise, e.g., synthetically derived) and immunogenic fragments of LytB (e.g, fragments comprising at least 15 or 20 contiguous amino acids present in the naturally occurring mature LytB protein). Immunogenic variants and fragments of the immunogenic LytB polypeptides described herein may be capable of eliciting an immune response specific for the corresponding full length mature amino acid sequence. LytB polypeptides suitable for use in the compositions described herein include, for example, those of GenBank Accession Nos. CAA09078, YP816335, ABJ55408, AAK19156, NP358461, and AAK75086, among others.

Preferred LytB polypeptides for use may comprise an amino acid sequence having 50% or more identity (e.g., 60, 65, 70, 75, 80, 85, 85, 90, 91, 92, 93, 94, 95, 96, 97, 98, 99, 99.5% or more) to SEQ ID NO:9, 10 or 11. Preferred polypeptides for use may comprise a fragment of at least, for example, 8, 9, 10, 12, 14, 16, 18, 20, 25, 30, 35, 40, 50, 60, 70, 80, 90, 100, 150, 200, 250 or more consecutive amino acids of SEQ ID NO:9, 10 or 11. Preferred fragments comprise an epitope from SEQ ID NO: 9, 10 or 11. Other preferred fragments lack one or more amino acids from the N-terminus of SEQ ID NO: 9, 10 or 11 (e.g., 1, 2, 3, 4, 5, 6, 7, 8, 9, 10, 15, 20, 25 or more) and/or one or amino acids from the C-terminus of SEQ ID NO:9 or 10 while retaining at least one epitope of SEQ ID NO:9 or 10. Further preferred fragments lack the signal sequence from the N-terminus of SEQ ID NO:10. A preferred LytB polypeptide is SEQ ID NO:11.

(LytB)
SEQ ID NO: 9
```
MKKVRFIFLALLFFLASPEGAMASDGTWQGKQYLKEDGSQAANEWVFDTH
YQSWFYIKADANYAENEWLKQGDDYFYLKSGGYMAKSEWVEDKGAFYYLD
QDGKMKRNAWVGTSYVGATGAKVIEDWVYDSQYDAWFYIKADGQHAEKEW
LQIKGKDYYFKSGGYLLTSQWINQAYVNASGAKVQQGWLFDKQYQSWFYI
KENGNYADKEWIFENGHYYYLKSGGYMAANEWIWDKESWFYLKFDGKIAE
KEWVYDSHSQAWYYFKSGGYMAANEWIWDKESWFYLKFDGKMAEKEWVYD
SHSQAWYYFKSGGYMTANEWIWDKESWFYLKSDGKIAEKEWVYDSHSQAW
YYFKSGGYMTANEWIWDKESWFYLKSDGKMAEKEWVYDSHSQAWYYFKSG
GYMAKNETVDGYQLGSDGKWLGGKATNKNAAYYQVVPVTANVYDSDGEKL
SYISQGSVVWLDKDRKSDDKRLAITISGLSGYMKTEDLQALDASKDFIPY
YESDGHRFYHYVAQNASIPVASHLSDMEVGKKYYSADGLHFDGFKLENPF
LFKDLTEATNYSAEELDKVFSLLNINNSLLENKGATFKEAEEHYHINALY
LLAHSALESNWGRSKIAKDKNNFFGITAYDTTPYLSAKTFDDVDKGILGA
TKWIKENYIDRGRTFLGNKASGMNVEYASDPYWGEKIASVMMKINEKLGG
KD
```

(LytB)
SEQ ID NO: 10
```
MNLGEFWYNKINKNRGRRLMKKVRFIFLALLFFLASPEGAMASDGTWQGK
QYLKEDGSQAANEWVFDTHYQSWFYIKADANYAENEWLKQGDDYFYLKSG
GYMAKSEWVEDKGAFYYLDQDGKMKRNAWVGTSYVGATGAKVIEDWVYDS
QYDAWFYIKADGQHAEKEWLQIKGKDYYFKSGGYLLTSQWINQAYVNASG
AKVQQGWLFDKQYQSWFYIKENGNYADKEWIFENGHYYYLKSGGYMAANE
WIWDKESWFYLKFDGKMAEKEWVYDSHSQAWYYFKSGGYMTANEWIWDKE
SWFYLKSDGKIAEKEWVYDSHSQAWYYFKSGGYMTANEWIWDKESWFYLK
SDGKIAEKEWVYDSHSQAWYYFKSGGYMAKNETVDGYQLGSDGKWLGGKT
TNENAAYYQVVPVTANVYDSDGEKLSYISQGSVVWLDKDRKSDDKRLAIT
ISGLSGYMKTEDLQALDASKDFIPYYESDGHRFYHYVAQNASIPVASHLS
DMEVGKKYYSADGLHFDGFKLENPFLFKDLTEATNYSAEELDKVFSLLNI
NNSLLENKGATFKEAEEHYHINALYLLAHSALESNWGRSKIAKDKNNFFG
ITAYDTTPYLSAKTFDDVDKGILGATKWIKENYIDRGRTFLGNKASGMNV
EYASDPYWGEKIASVMMKINEKLGGKD
```

(LytB construct derived from Spn strain 14453; lacking the signal sequence and choline binding regions; vector derived sequence is underlined)
SEQ ID NO: 11
```
MGKATNENAAYYQVVPVTANVYDSDGEKLSYISQGSVVWLDKDRKSDDKR
LAITISGLSGYMKTEDLQALDASKDFIPYYESDGHRFYHYVAQNASIPVA
SHLSDMAVGKKYYSADGLHFDGFKLENPFLFKDLTEATNYSAEELDKVFS
LLNINNSLLENKGATFKEAEEHYHINALYLLAHSALESNWGRSKIAKDKN
NFFGITAYDTTPYLSAKTFDDVDKGILGATKWIKENYIDRGRTFLGNKAS
GMNVEYASDPYWGEKIASVMMKINEKLGGKD
```

Pneumolysin (Ply) is a cytolytic-activating toxin implicated in multiple steps of pneumococcal pathogenesis, including the inhibition of ciliary beating and the disruption of tight junctions between epithelial cells (Hirst et al. Clinical and Experimental Immunology (2004)). Several pneumolysins are known and (following detoxification) would be suitable for use in the compositions described herein including, for example GenBank Accession Nos. Q04IN8, P0C2J9, Q7ZAK5, and ABO21381, among others. In one embodiment, Ply has the amino acid sequence shown in SEQ ID NO.12.

Immunogenic pneumolysin polypeptides may include the full length protein with the signal sequence attached, the mature full length protein with the signal peptide removed, variants of pneumolysin (naturally occurring or otherwise, e.g., synthetically derived) and immunogenic fragments of pneumolysin (e.g, fragments comprising at least 15 or 20 contiguous amino acids present in the naturally occurring mature pneumolysin protein). Immunogenic variants and fragments of the immunogenic pneumolysin polypeptides may be capable of eliciting an immune response specific for the corresponding full length mature amino acid sequence. The immunogenic pneumolysin polypeptides are typically detoxified; that is, they lack or have reduced toxicity as compared to the mature wild-type pneumolysin protein produced and released by *S. pneumoniae*. The immunogenic pneumolysin polypeptides may be detoxified for example, chemically (e.g., using formaldehyde treatment) or genetically (e.g., recombinantly produced in a mutated form). Preferred examples of the immunogenic detoxified pneumolysin are disclosed in PCT Publication No. WO 2010/071986. In one embodiment, immunogenic detoxified pneumolysin has the amino acid sequence shown in SEQ ID NO: 13.

Preferred pneumoysin polypeptides may comprise an amino acid sequence having 50% or more identity (e.g., 60, 65, 70, 75, 80, 85, 85, 90, 91, 92, 93, 94, 95, 96, 97, 98, 99, 99.5% or more) to SEQ ID NO:12 or to SEQ ID NO:13. Preferred polypeptides may comprise a fragment of at least 8, 9, 10, 12, 14, 16, 18, 20, 25, 30, 35, 40, 50, 60, 70, 80, 90, 100, 150, 200, 250 or more consecutive amino acids of SEQ ID NO:12 or 13. Preferred fragments may comprise an epitope from SEQ ID NO:12 or to SEQ ID NO:13. Other preferred fragments lack one or more amino acids from the N-terminus of SEQ ID NO. 12 or 13 (e.g., 1, 2, 3, 4, 5, 6, 7, 8, 9, 10, 15, 20, 25 or more) and/or one or amino acids from the C-terminus of SEQ ID NO:12 or 13 while retaining at least one epitope of SEQ ID NO:12 or 13. Further preferred fragments lack the signal sequence from the N-terminus of SEQ ID NO:12. A preferred immunogenic and detoxified pneumolysin polypeptide is SEQ ID NO:13.

```
(PLY)
                                         SEQ ID NO: 12
MANKAVNDFILAMNYDKKKLLTHQGESIENRFIKEGNQLPDEFVVIERKK
RSLSTNTSDISVTATNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILGGDPSSGA
RVVTGKVDMVEDLIQEGSRFTADHPGLPISYTTSFLRDNVVATFQNSTDY
VETKVTAYRNGDLLLDHSGAYVAQYYITWDELSYDHQGKEVLTPKAWDRN
GQDLTAHFTTSIPLKGNVRNLSVKIRECTGLAWEWWRTVYEKTDLPLVRK
RTISIWGTTLYPQVEDKVEND (PlyD1 construct derived from Spn strain 14453)
                                         SEQ ID NO: 13
MANKAVNDFILAMNYDKKKLLTHQGESIENRFIKEGNQLPDEFVVIERKK
RSLSTNTSDISVTACNDSRLYPGALLVVDETLLENNPTLLAVDRAPMTYS
IDLPGLASSDSFLQVEDPSNSSVRGAVNDLLAKWHQDYGQVNNVPARMQY
EKITAHSMEQLKVKFGSDFEKTGNSLDIDFNSVHSGEKQIQIVNFKQIYY
TVSVDAVKNPGDVFQDTVTVEDLKQRGISAERPLVYISSVAYGRQVYLKL
ETTSKSDEVEAAFEALIKGVKVAPQTEWKQILDNTEVKAVILCGDPSSGA
RVVTGKVDMVEDLIQEGSRFTADHPGLPISYTTSFLRDNVVATFQNSTDY
VETKVTAYRNGDLLLDHSGAYVAQYYITWDELSYDHQGKEVLTPKAWDRN
GQDLTAHFTTSIPLKGNVRNLSVKIREATGLAWEWWRTVYEKTDLPLVRK
RTISIWGTTLYPQVEDKVEND
```

Variants of the immunogenic polypeptides described herein are selected for their immunogenic capacity using methods well known in the art. Such variants may comprise amino acid modifications. For example, amino acid sequence modifications include substitutional, insertional or deletional changes. Substitutions, deletions, insertions or any combination thereof may be combined in a single variant so long as the variant is an immunogenic polypeptide. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in a recombinant cell culture. Techniques for making substitution mutations at predetermined sites in DNA having a known sequence are well known and include, but are not limited to, M13 primer mutagenesis and PCR mutagenesis. Amino acid substitutions are typically of single residues but can occur at a number of different locations at once. Substitutional variants are those in which at least one residue has been removed and a different residue inserted in its place. Such substitutions generally are made in accordance with the following Table and are referred to as conservative substitutions. Others are well known to those of skill in the art.

As used herein, the amino acid substitution may be conservative or non-conservative. Conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in the Table 1 below.

TABLE 1

| Original Residues | Exemplary Conservative Substitutions | Preferred Conservative Substitution |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptides and/or fragments provided herein using well-known techniques.

Analogs can differ from naturally occurring *S. pneumoniae* polypeptides in amino acid sequence and/or by virtue of non-sequence modifications. Non-sequence modifications include changes in acetylation, methylation, phosphorylation, carboxylation, or glycosylation. A "modification" of a polypeptide may include polypeptides (or analogs thereof, such as, e.g. fragments thereof) that are chemically or enzymatically derived at one or more constituent amino acid. Such modifications can include, for example, side chain modifications, backbone modifications, and N- and C-terminal modifications such as, for example, acetylation, hydroxylation, methylation, amidation, and the attachment of carbohydrate or lipid moieties, cofactors, and the like, and combinations thereof. Modified polypeptides described herein may retain the biological activity of the unmodified polypeptides or may exhibit a reduced or increased biological activity.

Structural similarity of two polypeptides can be determined by aligning the residues of the two polypeptides (for example, a candidate polypeptide and the polypeptide of, for example, SEQ ID NO: 2) to optimize the number of identical amino acids along the length of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide. A candidate polypeptide can be isolated, for example, from a microbe, or can be produced using a recombinant techniques, or chemically or enzymatically synthesized.

A pair-wise comparison analysis of amino acids sequences can be carried out using a global algorithm, for example, Needleman-Wunsch. Alternatively, polypeptides may be compared using a local alignment algorithm such as the Blastp program of the BLAST 2 search algorithm, as described by Tatiana et al., (FEMS Microbiol. Lett, 174 247-250 (1999), and available on the National Centre for Biotechnology Information (NCBI) website. The default values for all BLAST 2 search parameters may be used, including matrix=BLOSUM62; open gap penalty=11, extension gap penalty=1, gap×dropoff=50, expect 10, word-size=3, and filter on. The Smith and Waterman algorithm is another local alignment tool that can be used (1988).

In the comparison of two amino acid sequences, structural similarly may be referred to by percent "identity" or may be referred to by percent "similarity." "Identity" refers to the presence of identical amino acids. "Similarity" refers to the presences of not only identical amino acid but also the presence of conservative substitutions. A conservative substitution for an amino acid in a polypeptide described herein may be selected from other members of the class to which the amino acid belongs, shown on Table 1.

Compositions

Compositions (e.g., vaccine compositions) may be administered in the presence or absence of an adjuvant. Adjuvants generally are substances that can enhance the immunogenicity of antigens. Adjuvants may play a role in both acquired and innate immunity (e.g., toll-like receptors) and may function in a variety of ways, not all of which are understood.

Many substances, both natural and synthetic, have been shown to function as adjuvants. For example, adjuvants may include, but are not limited to, mineral salts, squalene mixtures, muramyl peptide, saponin derivatives, *mycobacterium* cell wall preparations, certain emulsions, monophosphoryl lipid A, mycolic acid derivatives, nonionic block copolymer surfactants, Quil A, cholera toxin B subunit, polyphosphazene and derivatives, immunostimulating complexes (ISCOMs), cytokine adjuvants, MF59 adjuvant, lipid adjuvants, mucosal adjuvants, certain bacterial exotoxins and other components, certain oligonucleotides, PLG, and others. These adjuvants may be used in the compositions and methods described herein.

In certain embodiments, the composition is administered in the presence of an adjuvant that comprises an oil-in-water emulsion comprising at least squalene, an aqueous solvent, a polyoxyethylene alkyl ether hydrophilic nonionic surfactant, a hydrophobic nonionic surfactant, wherein said oil-in-water emulsion is obtainable by a phase inversion temperature process and wherein 90% of the population by volume of the oil drops has a size less than 200 nm, and optionally less than 150 nm. Such an adjuvant is described in WO2007006939 (Vaccine Composition Comprising a Thermoinversable Emulsion) which is incorporate herein in its entirety. The composition may also include the product E6020 (having CAS Number 287180-63-6), in addition to, or instead of the described squalene oil-in-water emulsion. Product E6020 is described in US2007/0082875 (which is incorporated herein by reference in its entirety).

In certain embodiments, the composition includes a TLR agonist (e.g., TLR4 agonist) alone or together in combination with an adjuvant. For example, the adjuvant may comprise a TLR4 agonist (e.g., TLA4), squalene, an aqueous solvent, a nonionic hydrophilic surfactant belonging to the polyoxyethylene alkyl ether chemical group, a nonionic hydrophobic surfactant and which is thermoreversible. Examples of such adjuvants are described in WO2007080308 (Thermoreversible Oil-in-Water Emulsion) which is incorporated herein in its entirety. In one embodiment, the composition is adjuvanted with a combination of CpG and an aluminum salt adjuvant (e.g., Alum).

Aluminum salt adjuvants (or compounds) are among the adjuvants of use in the practice of the invention. Examples of aluminum salt adjuvants of use include aluminum hydroxide (e.g., crystalline aluminum oxyhydroxide AlO (OH), and aluminum hydroxide $Al(OH)_3$. Aluminum hydroxide is an aluminum compound comprising $Al^3$ ions and hydroxyl groups (—OH). Mixtures of aluminum hydroxide with other aluminum compounds (e.g., hydroxyphosphate or hydroxysulfate) may also be of use where the resulting mixture is an aluminum compound comprising hydroxyl groups. In particular embodiments, the aluminum adjuvant is aluminum oxyhydroxide (e.g., ALHYDROGEL ®). It is well known in the art that compositions with aluminum salt adjuvants should not be exposed to extreme temperatures, i.e. below freezing (0° C.) or extreme heat (e.g., ≥70 ° C.) as such exposure may adversely affect the stability and the immunogenicity of both the adsorbed antigen and adjuvant.

In a particular embodiment, the aluminum compound (e.g., aluminum hydroxide adjuvant) is treated with phosphate In a preferred embodiment, phosphate is added to aluminum hydroxide adjuvant in the form of a salt. Preferably, the phosphate ions are provided by a buffer solution comprising disodium monosodium phosphate.

In a preferred practice, as exemplified herein, the aluminum compound (e.g., aluminum oxyhydroxide) is treated with phosphate (for example, by a process as described in WO2011/075822 (filed on 20 Dec. 2010 and entitled, Immunogenic Compositions and Related Methods). In this process, an aqueous suspension of aluminum oxyhydroxide (approximately 20 mg/mL) is mixed with a phosphate buffer solution (e.g., approximately 400 mol/L). The preferable final phosphate concentration is from about 2 mM to 20 mM. The mixture is then diluted with a buffer (e.g., Tris-HCl, Tris-HCl with saline, HEPES) to prepare a suspension of aluminum oxyhydroxide and phosphate (PO4). Preferably the buffer is 10 mM Tris-HCl and 150 mM NaCl at a pH of about 7.4. The suspension is then mixed for approximately 24 hr at room temperature. Preferably the concentration of elemental aluminum in the final suspension is within a range from about 0.28 mg/mL to 1.68 mg/mL. More preferably, the concentration of elemental aluminum is about 0.56 mg/mL.

The immunogenic polypeptides (e.g., PcpA, PhtD), individually or in combination may then be adsorbed to the treated aluminum hydroxide.

The compositions may preferably be in liquid form, but they may be lyophilized (as per standard methods) or foam dried (as described in WO2009012601, Antigen-Adjuvant Compositions and Methods). A composition according to one embodiment is in a liquid form. An immunization dose may be formulated in a volume of between 0.5 and 1.0 ml. Liquid formulations may be in any form suitable for administration including for example, a solution, or suspension. Thus, the compositions can include a liquid medium (e.g., saline or water), which may be buffered.

The pH of the formulation (and composition) may preferably be between about 6.4 and about 8.4. More preferably, the pH is about 7.4. An exemplary pH range of the compositions is 5-10, e.g., 5-9, 5-8, 5.5-9, 6-7.5, or 6.5-7. The pH may be maintained by the use of a buffer.

The pharmaceutical formulations of the immunogenic compositions of the present invention may also optionally include one or more excipients (e.g., diluents, thickeners, buffers, preservatives, surface active agents, adjuvants, detergents and/or immunostimulants) which are well known in the art. Suitable excipients will be compatible with the antigen and with the aluminum adjuvant as is known in the art. Examples of diluents include binder, disintegrants, or dispersants such as starch, cellulose derivatives, phenol, polyethylene glycol, propylene glycol or glycerin. Pharmaceutical formulations may also include one or more active ingredients such as antimicrobial agents, anti-inflammatory agents and anesthetics. Examples of detergents include a TWEEN® (polysorbate) such as TWEEN® 80. Suitable excipients for inclusion in the composition of the invention are known in the art.

In one embodiment of adjuvanted immunization, for example, immunogenic polypeptides and/or fragments thereof may be covalently coupled to bacterial polysaccharides to form polysaccharide conjugates. Such conjugates may be useful as immunogens for eliciting a T cell dependent immunogenic response directed against the bacterial polysaccharide conjugated to the polypeptides and/or fragments thereof.

Immunogenic compositions may be presented in a kit form comprising the immunogenic composition and an adjuvant or a reconstitution solution comprising one or more pharmaceutically acceptable diluents to facilitate reconstitution of the composition for administration to a mammal using conventional or other devices. Such a kit would optionally include the device for administration of the liquid form of the composition (e.g. hypodermic syringe, microneedle array) and/or instructions for use.

EXAMPLES

The above disclosure generally describes certain embodiments of this subject matter. A more complete understanding can be obtained by reference to the following specific Examples. These Examples are described solely for purposes of illustration and are not intended to limit the scope of this disclosure. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used, but not explicitly described in this disclosure and these Examples, are amply reported in the scientific literatures and are well within the ability of those skilled in the art.

Immune Responses

CD4+ T-cells are considered of prime importance against extracellular pathogens such as for example, *S. pneumonaie*. Upon stimulation with antigen loaded antigen-presenting cells (APCs) in context to MHC class 11 molecules, naïve CD4+ T-cells may differentiate into functionally different T-helper (Th)-subsets. The commitment to different Th-subsets depends on a complex interaction with APCs in a permissive milieu, including antigenic type and load, co-stimulatory molecules and cytokine signaling (7-9). For example, Th1 cells, characterized by interleukin (IL)-2, interferon-gamma (IFN-γ) and tumor necrosis factor-beta (TNF-β), production are of primary importance to eradicate intracellular pathogens. Th2-cells, essential in eliminating extracellular pathogens, express IL-4, IL-5, IL-6, IL-10, IL-13, and IL-25. Recently discovered Th17 cells secrete IL-17, IL-21, and IL-22 (10).

Memory T-cell responses are either generated during the effector response (linear model or asymmetric division) or are the remnant of a large cache of effector clonotypes that contracts and persists after pathogen clearance (11). Immunological memory, with its rapid recall responses and high cytokine production represents a highly effective mechanism to ensure quick protection against prevalent infection, and serves as a primary defense against pathogen re-encounter at portal entry points such as the respiratory mucosa (12;13). Robust memory T- and B-cell responses are generated during both onset of a natural infection as well as upon vaccination, with memory lymphocytes populating lymphoid and non-lymphoid sites (14-16). Once generated, memory T-cells can be detected in the blood circulation over a period of time (15;17;18). Current concepts of generating immunity against Spn have evolved from studies in mice defining a major role for CD4+ Th (helper)-memory subsets (Th-1, Th-2 & Th-17) (19-21). In animal models CD4+ T-cell immunity plays a significant role in protection against otopathogens and can also impart antibody independent immunity (20;22;23). However, there is no data to support a protective role of T-helper memory subsets among humans experiencing AOM.

The central role of antigen specific CD4+ T-cells in the adaptive immune response is to provide help for B-cells in the production of antibodies on the one hand and as their own effectors of immune function on the other (7;9;23;27). Furthermore, in the constant cytokine milieu provided by Th-cells and in response to antigenic stimulation, specific B-cells undergo clonal expansion, class switch and somatic hyper mutation leading to the selection of antibodies with higher affinity (28;29). The expanded B-cells differentiate into plasma cells that secret antibodies at high rate and persist in niches like bone marrow while some differentiate into memory B-cells (29;30). The memory B-cells can rapidly respond to antigenic re-stimulation and may contribute to maintain the plasma cell pool and therefore serum antibody levels for prolonged periods of time with the constant help from CD4+ T-cells (31).

Example 1

To evaluate the otitis-prone condition in children, using pneumococcal protein antigens, Spn specific functional memory CD4+ Th-cell subsets in the peripheral blood of a cohort of non otitis-prone and otitis-prone children were enumerated. The B-cell IgG responses were also measured to the same antigens in the serum of the children of these cohorts.

Subjects were participants from a 5-year prospective longitudinal AOM study funded by the US NIH (26). Children having three episodes of AOM within 6 months or 4 episodes within one year were considered as otitis-prone while others who had fewer episodes were placed into the non otitis-prone group. Enrolled children were from a middle class, suburban socio-demographic population in Rochester N.Y. Healthy children at age of 6 months without prior AOM were enrolled and had scrum, nasopharyngeal (NP) and oropharyngeal (OP) cultures obtained seven times, at the age 6, 9, 12, 15, 18, 24 and 30 months and both the cohorts had children of varying age under 2 yr. Middle ear fluid was obtained by tympanocentesis during AOM episodes. Evaluation of NP/OP colonization with *Streptococcus pneumoniae* and *Haemophilus influenzae*) was routinely obtained by microbiological tests of the cultured NP and OP surface and middle car fluids. PBMCs from the collected blood were isolated and frozen in the liquid nitrogen until used. Samples used in this study were taken at the time of their AOM visits from otitis-prone children, and during colonization or AOM visits from non otitis-prone group. Children had been immunized against *S. pneumoniae* according to applicable schedule with age appropriate doses of available conjugate vaccine.

Antigens

Pneumococcal protein antigens used were PhtD (SEQ ID NO:6), PhtE (SEQ ID NO:8), LytB (SEQ ID NO:11), PcpA (SEQ ID NO:3), and PlyD1 (SEQ ID NO:13), a detoxified derivative of pneumolysin. As a control, PspA was also used. Each of the proteins were cloned from a *S. pneumoniae* serotype 6B strain and recombinantly expressed in *E. coli* as soluble proteins and then purified with combinations of ion exchange chromatography. The proteins each had ≥90% purity after purification as assayed by SDS-PAGE and RP-HPLC.

An optimal dosage for stimulation was determined by absence of detectable cell toxicity, by the use of tryptan blue staining and/or flow cytometry analysis after propidium iodide staining (data not shown).

T-Cell Stimulation

PBMCs from otitis prone and non-otitis prone children who were NP colonized or AOM-infected with Spn were stimulated with the six pneumococcal antigens whereas children who were NP colonized or AOM-infected with NTHi were stimulated with the three NTHi antigens. Prior to stimulation, frozen PBMCs were quickly thawed in a 37° C. water bath followed by slowly adding complete culture medium (RPMI 1640 supplemented with 10% of FBS, 2 mM L-glutamine, 0.1 mM sodium pyruvate, nonessential amino acids, 100 U/mL penicillin, 100 µg/mL streptomycin). Cells were then washed and rested overnight in complete culture media in 24-well plates. PBMCs were stimulated usine a standardized protocol adapted from previous reports (35;36). Briefly, cells were counted and placed in a 96-well flat bottom culture plate and were stimulated with either 1 µg/ml of various protein antigens or with 1ng/ml of Staphylococcal enterotoxin B (SEB). To the cell culture 1 µg/ml concentrations of anti-CD28 and anti-CD49d antibodies (clones L293 and L25 respectively; BD Biosciences) were added to provide co-stimulation and enhance the detection of antigen specific responses. Anti-CD28 and CD49d antibodies have been widely used for co-stimulation without affecting background levels (18;37). Cells were then incubated for 2 h at 37° C. in the presence of 5% CO2 for antigen processing. After 2 hours, golgi transport inhibitors (BD Biosciences) were added to preserve cytokines intracellularly and incubation was then continued for an additional 4 hours.

Cytokine Profiling

A multi-parameter flow cytometry approach was used to detect specific CD4+T-cell responses to the Spn proteins in the circulation after AOM or NP colonization in study cohorts. An intracellular cytokine staining assay (ICCS) was used to evaluate antigen specific CD4+T-cell subsets (Th-1, Th-2 and Th-17). After stimulation, cells were transferred to 96-well V-bottom plates and washed once with FACS buffer (PBS with 5% FBS) and stained with the antibodies to various cell surface markers. Antibodies used were anti-CD4APC ALEXA FLUOR® 750 (clone RPA T4, eBiosciences), PE TEXAS RED® anti- CD45RA (clone MEM56, Invitrogen), anti-CCR7PerCP/Cy5.5 conjugate (clone TG8/CCR7, Biolegend). Cells were then permeabilized with fixation and permeabilization solution (BD Biosciences) for 20-minutes and washed three times with 1x permeabilization buffer (BD Biosciences). A cocktail of various cytokine specific antibodies was used to stain intracellularly captured cytokines as a result of stimulation. Antibodies used were PE-Cy7 conjugated anti-IFN-γ(clone B27, BD biosciences), Pacific blue conjugated anti IL17A (clone BL168, Biolegend), ALEXA FLUOR® 700anti IL-2 (clone MQ1-17H12, Biolegend), PE conjugated anti IL-4(clone 8D4-8, BD Biosciences), AF 488 conjugated TNF-α, anti-CD3QDOT® 605 (clone UCHT1, Invitrogen) and PE-Cy5 anti-CD69 (clone FN50, BD biosciences). After intracellular staining, cells were further washed 3-times with 1x permeabilization buffer and one final wash with FACS buffer before resuspending them into the FACS tubes. A custom made BD LSR II flow cytometer equipped for the detection of 12fluorescent parameters was used to collect 2-5 ×105 events for each sample and data was analyzed using FLOW JO (Tree Star) software. To exclude cell debris and clumps, cells were first gated based on their for ard- and side-scatter properties followed by sequential gating on CD4+ T-cells followed by CD45RALow and then to CD69+ cytokine positive cells. Alternatively, cells were also gated on TNF-α Vs other cytokines for confirmation. Low frequency responders were confirmed by excessive back gating. As previously reported, to aid in the detection of antigen specific cells anti-CD28/CD49d antibodies in conjunction with multi-parameter staining was used to help avoid irrelevant background (37). The whole assay was standardized and compared to multiplex bead array (CBA, BD Biosciences) for the detection of cytokine profile.

Humoral Responses

For measuring IgG antibody levels in the samples, ELISA was performed as described earlier (26;38). Briefly, 96-well plates (Nunc-Immulon) were coated with 0.25 µg/ml of individual antigens (100 µl/well) in coating buffer (bicarbonate, (pH 9.4) and incubated overnight at 4° C. After washing the plates were blocked with 3% skimmed milk at 37° C. for 1 hr (200 µl per well). After five washes, 100 µl of serum at a starting dilution of 1:100 (in PBS-3% skim milk) was added to the wells and diluted serially 2 fold. The mixture was incubated at room temperature for 1 hr followed by the addition of affinity purified goat anti-human IgG antibody conjugated to horseradish-peroxidase (Bethyl Laboratories, Inc, Montgomery, Tex.) as a secondary antibody. The reaction products were developed with TMB Microwell Peroxidase Substrate System (KPL, Gaithersburg, Md.), stopped by the addition of 1.0 molar phosphoric acid and read by an automated ELISA reader using a 450-nm filter. To provide quantitative results on antibody concentrations, the level of the specific antibody present in the unknown sample was determined by comparison with an internal reference serum (pool of human serum with high antigen specific antibody levels). The levels of IgG in the reference serum were quantitatively measured by using a human IgG ELISA quantitation kit (Bethyl laboratories). A Four-parameter logistic-log function was used to form the reference and sample curves. This ELISA was fully validated according to ICH Guidance.

All data was statistically analyzed using Graph Pad Prism software. Two tailed P values for the data were calculated using Mann Whitney Test.

Results

Children in the otitis prone group were of a similar age as the non-otitis prone children. The distribution in gender, day care attendance, passive cigarette smoke exposure in the household, number of siblings under 8 years of age and breast fed were similar in the two study groups.

The circulating frequencies of various Spn antigen specific memory Th-cell subsets were compared between non otitis-prone and otitis-prone children by stimulating their PBMCs with specific antigens. For that, the percentages of CD45RALow memory CD4+ T-cells producing IFN-γ, IL-4, IL-2 or IL-17 were calculated by gating on recently activated CD69+ T-cells. Antigen specific responses were normalized with the control PBMCs left unstimulated or stimulated with a non specific antigen (Keyhole limpet hemocyanin).

FIG. 1, which sets out a summary of the results, demonstrates detectable frequencies of the various subsets of CD45RALow memory CD4+ T-cells to all the Spn antigens used for stimulation in non otitis prone children (n=15) following AOM (n=6) or NP colonization (n=9) with Spn. In sharp contrast, otitis-prone children (n=13) had a marked deficiency of circulating Spn specific memory CD4+ T-cells after AOM (n=10) and NP colonization (n=3). In particular, there was a complete lack of memory CD4+ T-cells producing IFN-γ against LytB, PhtE and Ply whereas significantly lower levels of IFN-γ were produced in response to PhtD, PcpA and PspA ($P<0.02$) (FIG. 1a). A significant decrease in IL-4 producing memory CD4+ T-cells was observed against PhtD and LytB ($P<0.02$) in the otitis-prone children (FIG. 1b). IL-2 responses to PhtD ($P<0.05$), PcpA ($P<0.005$), PhtE ($P<0.05$). Ply ($P<0.005$) and PspA (0.02) were significantly lower in otitis-prone children (FIG. 1c) and a significant reduction in IL-17a producing cells were found in otitis-prone children in response to PhtD, PcpA and PhtE ($P<0.05$) (FIG. 1d).

Figure 2:
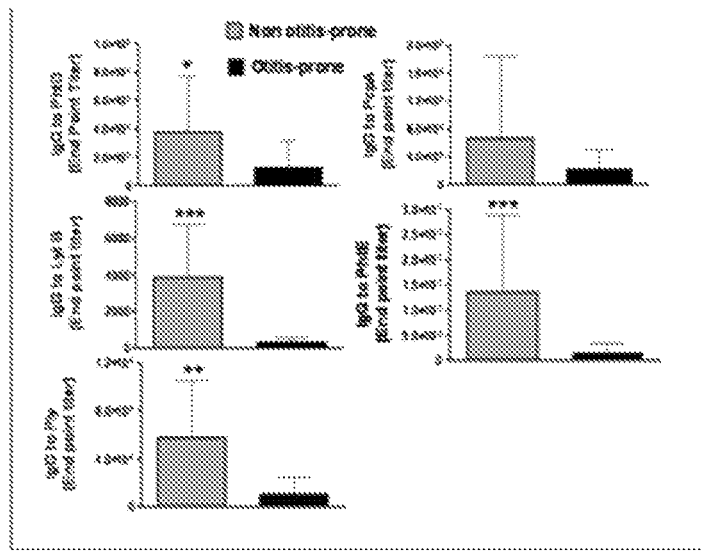
FIG. 2. Is a graphical representation showing the comparison of IgG responses to five pneumococcal protein antigens (PhtD, LytB, PcpA, PhtE and Ply) in the serum samples of two cohorts of non-otitis-prone and otitis-prone children. *$P<0.05$; $P<0.005$; *$P<0.0005$. Y-axis represents Geometric mean titers and error bars are upper 95% confidence intervals.
Figure 3:
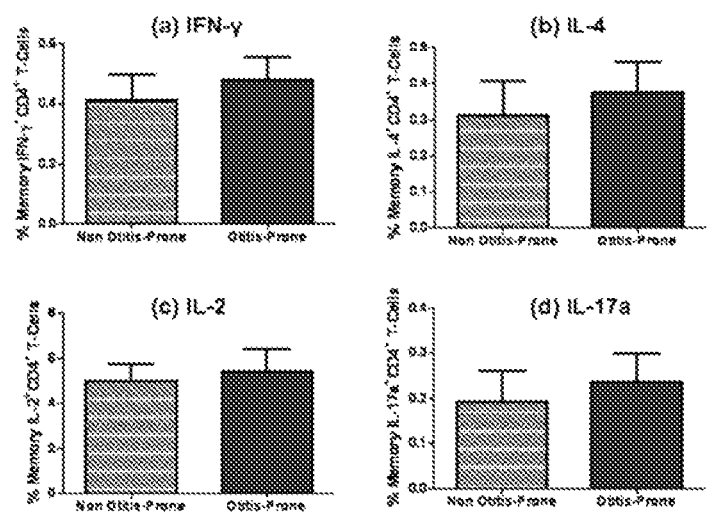
FIG. 3. Is a graphical representation showing CD4+ T-cell response to SEB. PBMC samples from non-otitis-prone and otitis-prone children were stimulated with SEB and cytokine production was observed in CD45RALow CD4+ T-cell population.

As the absence of antigen specific memory Th-cells may result in impaired antigen specific B-cell responses (9), the antigen specific IgG titers in the non otitis-prone and otitis-prone children were assessed. Serum IgG levels against the pneumococcal antigens in the respective groups are shown in FIG. 2. As expected, with the increased memory T-cell frequencies, IgG titers to PhtD, LytB, PhtE, Ply were significantly higher in the non otitis-prone group compared to otitis-prone group ($P<0.05$; 0.0005; 0.0005; 0.005 respectively) (FIG. 2). There was an increase in the IgG titer to PcpA antigen as well but the difference was not significant (FIG. 3).

Since, the immune system in young children is not fully mature in the context of T- and B-cell responses (39;40), B cell and T cell mediated responses were tested to assess whether the whether the impaired memory 1-cell responses among otitis-prone children were due to intrinsic T- or B-cell defects. PBMC were stimulated with SEB, an antigen that stimulates a T-cell response independent of APC involvement (41). FIG. 3 shows the percentage of memory CD4+ T-cells producing IFN-γ, IL-4, IL-2 or IL-17a is the same for otitis prone and non otitis prone children. Given that all the children had received a DTaP vaccine, IgG titers against the vaccine antigens diphtheria, tetanus and pertussis were determined to assess whether the otitis prone child has a generalized immune deficiency. No significant differences were found in IgG antibody concentrations to diptheria toxoid, tetanus toxoid, pertussis toxin, filamentous hemagglutinin or pertactin between the groups (data not shown).

In sum, these data show that Spn otitis-prone children have a lack or reduction of pneumococcal antigen specific functional memory CD4+ T-cells as compared to non-otitis prone children. This effect was associated with reduced IgG responses to the studied antigens. As shown by the data, otitis-prone children fail to generate antigen specific CD45RALow functional Th-memory responses to Spn and elicit reduced antibody responses to Spn protein antigens. These children are not however deficient in total functional memory T-cells or in eliciting B cell mediated antibody responses (e.g., IgG) against vaccinated antigens.

In spite of the fact that CD4+ Th cells assist in fighting infections caused by Spn and NTHi, there has not been any previous report demonstrating a direct role of specific CD4+ Th-cells associated with Spn or NTHi-mediated AOM in children. Clearly, poor generation of CD4+ T-cell memory in children would lead to subsequent diminished B-cell mediated antibody responses. The lack of immunologic memory thus could result in repeated susceptibility to recurrent ear infections. Here, for the first time we demonstrate that otitis-prone children have an absence/reduction in otopathogen (e.g., *S. pneumoniae*) specific memory among Th-cells in the blood circulation following AOM and/or NP colonization. In contrast, non otitis-prone children generate memory antigen specific CD4+ T-cells after AOM and/or NP colonization with otopathogens.

It appears that the otitis prone child does develop a short-lived B cell response since some antibodies are detectable among these children after AOM and NP colonization with *S. pneumoniae*. However, in the absence of T cell memory, after the antibody level wanes the child quickly becomes susceptible to additional AOM infections. Thus, the fundamental immunologic deficit appears to be in the generation of T cell memory among otitis prone children. Since otitis-prone children responded similarly to an antigen that does not require APC processing (SEB) and similarly to a parenteral injection of antigen in the form of a DTaP vaccine, it may be that the problem among otitis prone children lays even further upstream immunologically in the actual processing and presentation of Spn and NTHi antigens by APCs present in the nasal mucosa.

Previous work has demonstrated the role of Spn and NTHi antigens in CD4+ T-cell proliferative responses (for 5-7 days) among children and adults (42;43). A prior study evaluated CD4+T-cell proliferation from cells collected from the adenoids and tonsils of otitis-prone children and found no proliferation in response to NTHi protein P6 (44). Studies of this nature evaluate antigen specific T-cell proliferation but fail to inform about occurrence of antigen specific memory CD4+T-cells.

While CD4+Th-2 cells promote most of the antibody responses that help in the elimination of bacterial pathogens from the host, recent studies in mouse models have shown antibody independent immunity to Spn NP colonization mediated by IL-17a producing CD4+ T-cells (Th-17 cells) (20). Here for the first time, in humans, increased frequencies were detected of Spn-specific IL-17a producing memory Th-cells in the circulation of non otitis-prone children, as compared to otitis-prone children. Thus, Spn-specific IL-17a producing memory Th-cells may protect against the otitis-prone condition.

The cellular phenotyping at the site of infection during AOM (middle ear mucosa and middle ear fluid) suggests a large migration of CD45ROHigh/CD45RALow memory CD4+ T-cells with loss of homing receptors L-selectin (45). Other studies reveal accumulation of mainly memory CD4+ T-cells in the middle ear fluid during AOM (45-47). Local secondary lymphoid organs such as adenoids are the primary sites for T-cell priming during upper respiratory tract infections such as bacterial colonization. Once, an antigen loaded APC migrates to local lymphoid organs (adenoids), the differentiation of lymphocytes (c.f. CD4+ T-cells) takes place. After entering the blood circulation the CD4+ T-cells eventually migrate to the middle ear mucosa (in the case of AOM) and/or the upper respiratory tract (during NP colonization).

Without being bound by theory, delayed immunologic maturation likely is responsible for the lack of functional T-cells among otitis-prone children (48). As children age, they become less prone to AOM because of anatomical changes in the custachion tube but also with age maturation of the immune system occurs. A robust T-cell memory response typically develops around age 3 to 5 years (40;48-51), and usually the otitis prone child "outgrows" their propensity during this age time frame.

In humans, memory CD4+ T-cells may play a key role in the fight against AOM. Therefore, Spn specific CD4+ T-cell memory, if generated, would be useful in the prevention of recurrent AOM incidences.

Example 2

In this study, the development of serum IgG antibodies to PhtD, PhtE, LytB, PepA and Ply among three groups of 6 to 36 month old children with AOM were compared: 1) an otitis prone group that included children who had three or more episodes of AOM in six months or four or more episodes in a 12 month period; 2) an AOM treatment failure (AOMTF) group that included children who failed to achieve bacterial eradication and/or resolution of symptoms after at least 48 hours of appropriate antibiotic therapy (70;71) and children whose signs and symptoms of AOM returned within 14 days of completing an antibiotic treatment course; and, 3) a non-otitis prone group that included children who had only one or two episodes of AOM.

The samples collected and analyzed were obtained during the prospective study referenced in Example 1. Healthy children without prior AOM were enrolled at age 6 months and followed prospectively until 30 months of age. Scrum, NP and oropharyngeal (OP) cultures were obtained seven times during the study period at age 6, 9, 12, 15, 18, 24, and 30 months. However, samples for the 30 month time point were excluded from this analysis as too few subjects had reached the 30 month visit. During the study period whenever a child experienced an AOM, serum, NP and OP cultures were obtained along with middle ear fluid (MEF) by tympanocentesis. Convalescent samples were collected three weeks later. The majority of these children developed no AOMs (about 70%) and were included in group 3 (non-otitis prone children). Some children went on to meet the definitions of otitis-prone (about 5%) and were included in group 1 or had AOMTF (about 5%) and were included as group 2 for analysis. To increase the size of the otitis prone and AOMTF cohorts, additional children were enrolled whenever they met those definitions within the age time span of 6 to 36 months old At the time of an AOM event, serum, NP, OP and MEF samples were collected acutely; and convalescent samples 3 weeks later.

To assure the diagnosis of AOM, children were examined by validated otoscopist pediatricians using the American Academy of Pediatrics AOM diagnostic guidelines. A tympanocentesis was performed to confirm the presence of an otopathogen in MEF. MEF, NP, and OP samples were inoculated into trypticase soy broth, trypticase soy agar with 5% sheep blood plates, and chocolate agar plates. Bacteria were isolated according to the CLSI standard culture procedures.

ELISA assay: The S. pneumoniae proteins PhtD, LytB, PcpA, PhtE and PlyD1 used in Example 1 were also used in this study. Protein specific antibody titers were determined by ELISA using purified recombinant proteins. 96-well Nunc-Immulon 4 plates were coated with 0.5 µg/ml of individual proteins (100 µl/well) in bicarbonate coating buffer (pH 9.4) and incubated overnight at 4° C. After washing the plates were blocked with 3% skim milk at 37° C. for 1 hr (200 µl per well). After five washes, 100 µl of serum at a starting dilution of 1:100 (in PBS-3% skim milk) was added to the wells and diluted serially 2 fold. The mixture was incubated at room temperature for 1 hr followed by the addition of affinity purified goat anti-human IgG antibody conjugated to horseradish-peroxidase (Bethyl Laboratories, Inc, Montgomery, Tex.) as a secondary antibody. The reaction products were developed with TMB Microwell Peroxidase Substrate System (KPL, Gaithersburg, Md.), stopped by the addition of 1.0 molar phosphoric acid and The plates were analyzed at 450 nm on a Spectra max plate reader (Molecular Devices, Sunnyvale, Calif.) using the Softmax endpoint dilution protocol.

Statistical analysis was performed on GraphPad Prism 5. Unpaired t test was used to compare the difference among three groups for the IgG antibody analysis. Paired t test was applied to compare acute vs. convalescence serum samples. One way ANOVA was used to evaluate the antibody rise over time. P values of <0.05 were considered significant.

Figure 4:
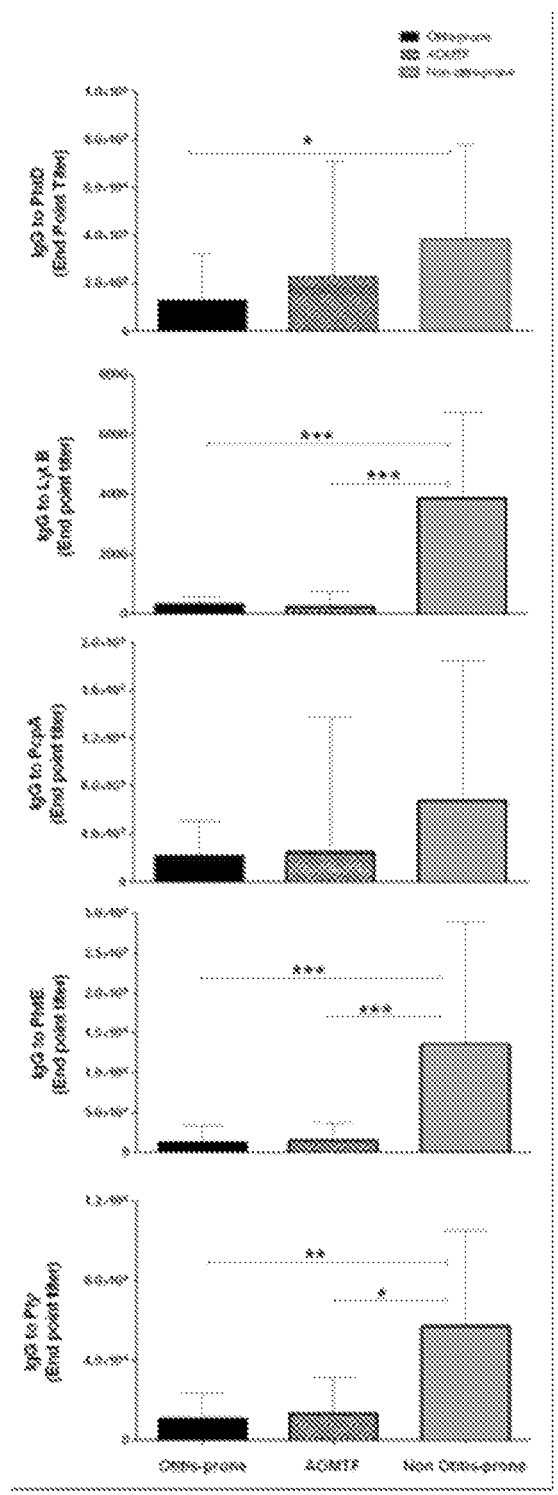
FIG. 4. Is a graphical representation showing the comparison of IgG antibody in the scrum samples of children at their acute visit of AOM in 35 otitis prone, 25 AOMTF and 34 non-otitis prone children. Note: All the antibody concentrations against five proteins are in end point titers. Lines are shown to indicate significant difference observed between the two groups. * means p value <0.0001,  means p value <0.001, and * means p value <0.05.

Specific IgG Antibody Titers Against PhtD, LytB, PcpA, PhtE and Ply in Three Groups of Children at the Time of an AOM IgG antibody titers against PhtD, LytB, PcpA, PhtE and Ply proteins of Spn were measured at the time of an acute AOM in 35 otitis prone children, 25 children with AOMTF and 34 children with their first or second AOM as a non-otitis prone group (FIG. 4).

The IgG titers against protein PhtD in the otitis prone children were significantly lower compared to non-otitis-prone children (p<0.05). The IgG antibody levels to PhtD in AOMTF children were also lower compared to non otitis-prone children but the difference did not achieve significance. The IgG titers to LytB in the otitis prone children and AOMTF children were significantly lower compared to non-otitis prone children (p<0.001 for both comparisons). The GMTs of IgG against protein PcpA in the otitis prone and AOMTF children were almost 3 times lower compared to non-otitis prone children but the difference was not statistically significant among 3 groups of children due to wide variation in levels of antibody. The IgG titers to protein PhtE in the otitis-prone children and AOMTF children were significantly lower compared to non-otitis prone children (p<0.001). The IgG titers to protein PlyD1 were significantly lower in the otitis prone children (p=0.006) and AOMTF children (p=0.02) compared to non-otitis prone children.

Acute and Convalescent AOM Antibody Levels Against PhtD, LytB, PcpA, PhtE and Ply of *S. pneumoniae* in Three Groups of Children.

Twenty two otitis prone, 13 AOMTF and 20 non-otitis prone children had paired serum samples obtained at their acute (at the time of AOM) and convalescent stage (3 weeks later). In all three groups of children, IgG antibody levels to 4 of the 5 proteins in the acute vs. convalescence stage showed no significant rise in antibody (the exception was PhtE protein in AOMTF children where a significant difference was found, p=0.04) (Table 1). However wide individual variation of the antibody levels in acute and convalescent stage sera were notable, with some children in all 3 groups showing two fold rises in antibody to one or more antigens (Table 2).

Antibody Level in Non-otitis Prone and Otitis-prone Children with Age

Figure 5:
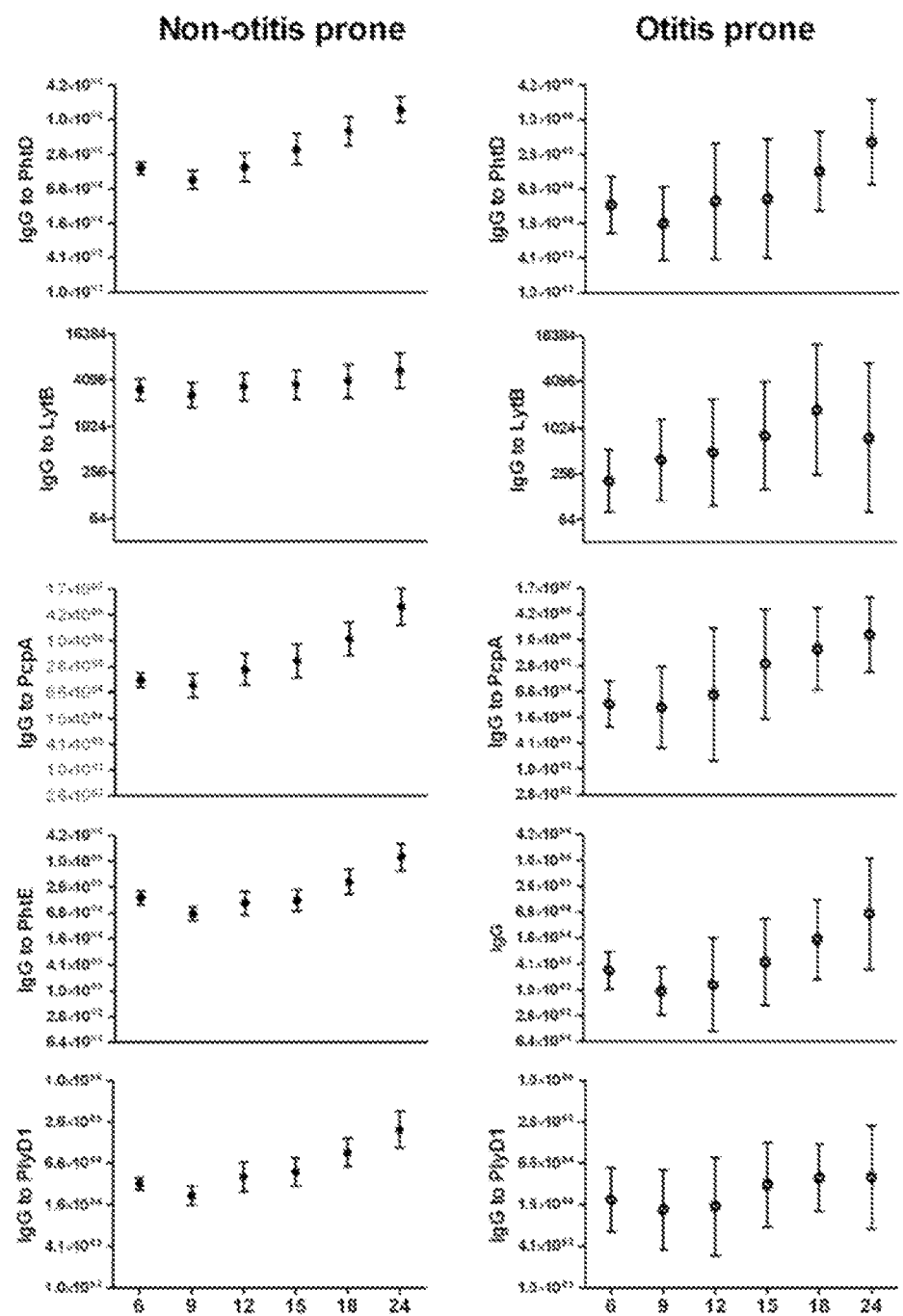
FIG. 5. Is a graphical representation showing the comparison of IgG antibody level with age (6-24 months) against five proteins of *S. pneumoniae* in non-otitis prone and otitis prone children. The numbers of sera included at 6, 9, 12, 15, 18 and 24 months time points were 107, 88, 65, 61, 55, and 44 respectively for the non-otitis prone children 10, 10, 9, 10, 10 and 4 respectively for the otitis prone children. Significant difference for all the five proteins except LytB (p<0.07), comparing relative rise in IgG scrum antibody over time was found in non-otitis prone children while the difference was not significant in otitis prone children (p=0.40 for protein PhtD, p=0.39 for LytB, p=0.11 for PcpA, p=0.09 for PhtE and p=0.42 for Ply).

FIG. 5 shows the IgG antibody levels against PhtD, LytB, PcpA, PhtE and Ply at the time of routine non-AOM visits in prospectively followed non-otitis prone and otitis prone children at 6-24 months of age. The data shown are from 150 non-otitis prone children and 10 otitis-prone children. In the non-otitis prone children, the IgG antibody levels rose significantly (p <0.001) over time for all the proteins except LytB (p=0.075). In comparison, the otitis prone children did not mount significant changes in IgG antibody level over time for any of the five proteins (p=0.40 for protein PhtD, p=0.39 for LytB, p=0.11 for PcpA, p=0.09 for PhtE and p=0.42 for Ply).

These data show that otitis prone children and children with AOMTF have significantly lower antibody levels to Spn proteins at the onset of AOM compared to non-otitis prone children, suggesting that prior exposures to Spn did not elicit or elicited a less robust adaptive immune response as reflected in serum antibody levels. This finding suggests that immunologically, otitis prone and AOMTF children are similar but their responses are different as compared to non-otitis prone children. Also, the amount of serum antibody to the 5 Spn antigens studied increased significantly more slowly in otitis prone children than in non-otitis prone children. Slower acquisition of antibody following natural exposure by NP colonization among otitis prone children is consistent with the observation of an impaired immune response among otitis prone children following otopathogen exposure. These data also shows that otitis prone children and children with AOMTF do not differ from non-otitis prone children in their serum antibody response to AOM. It appears that AOM is not an immunizing event for the majority of children in any of the three groupings, at least in the age range up to 3 years old (as were studied here).

The antigen specific immune responses observed against Spn confirm and extend the observations of others for otitis prone children, contradict some earlier reports and provide much new data. Freijd et al (72) described serum anti-Spn polysaccharide antibody to serotypes 3, 6A and 23 in 15 otitis prone children at 30 months of age compared to age matched control children and adults. They found significantly lower antibody to serotypes 6A and 23 among otitis prone children. Prellner et al (73) measured serum anti-Spn polysaccharide antibody to serotypes 6A, 19 and 23 in 15 otitis prone children and found that 60% of the children had no detectable antibody. Even at 6 years of age the levels of antibody to the 6A polysaccharide in otitis prone children were lower than non-otitis prone children. Hotomi et al (74) evaluated 36 otitis prone (mean age 18 months old) and 20 non otitis prone children for serum antibody responses to NTHi OMP P6 and Spn polysaccharide (using the 23 valent Spn vaccine as antigen). 55% of the otitis prone children had lower antibody responses to P6 and 48% had lower responses to Spn polysaccharide. Yamanaka and Faden in their 1993 studies (75;76) and Bernstein et al (77) found similar diminished serum and/or mucosal antibody levels to another otopathogen, NTHi, in otitis prone children. To our knowledge this is the first report of serum antibody responses to Spn proteins in otitis prone and in AOMTF children.

These observations regarding anti-PhtD, LytB, PcpA, PhtE and Ply antibody responses in otitis prone children associated with AOM supports the generally held explanation for the otitis prone state: These children have a specific immunologic deficiency in antibody response to Spn and other otopathogens when the exposure occurs via the natural NP route.

As noted in Example 1, otitis prone children have a deficiency in functional T helper cells and T memory cell in response to Spn and NTHi antigens (unpublished results) (82). The antibody responses in these children to parenteral vaccination with diphtheria, tetanus and pertussis were not reduced and these findings are consistent with the observations of Prellner et al (83) and Wiertsma et al (84) who also found that otitis prone children mount normal serum antibody responses to vaccination to measles and other pediatric vaccines. Therefore, the immune dysfunction in otitis prone children occurs with natural exposure to otopathogens and not with parenteral vaccination. Adequate immune responses to Spn conjugate vaccines observed to occur in otitis prone children support this conclusion. (85;86)

Comparing acute and convalescent antibody levels to the studied Spn proteins, the overall GMTs did not show a significant rise in otitis prone, AOMTF or non-otitis prone children. This is largely due to large variation in individual child immune responses. Indeed, some children did show higher convalescent titers while others showed lower titers and some remained the same. Most likely these results are due to differences in the length of NP carriage of Spn before AOM infection ensued. Those with longer carriage may achieve a peak in antibody response before the onset of AOM and they may show steady or falling antibody levels in acute to convalescent sera. Other children may have a brief time of NP carriage before the onset of AOM and they show rising acute to convalescent antibody levels. These results indicate that the different antigens elicit different antibody response profiles, possibly reflecting their different antigenicity in young children when the protein is presented to the child host in a natural way by asymptomatic colonization or AOM infection. Similar observations were made when antibody responses to NTHi proteins were evaluated and other groups have also observed this variability in acute to convalescent antibody levels surrounding an AOM event (87-89) Soininen et al studied the natural development of antibodies to Spn polysaccharide types 1, 6B, 11A, 14, 19F and 23F associated with NP colonization and AOM in a cohort of 329 children followed during their first 2 years of life. (90) Antibodies increased modestly but significantly over time; serotypes 11A and 14 were more immunogenic at a younger age. They found that antibody levels were equal after NP colonization or AOM. However in a later study involving the same children Soininen et al described the findings as indicating that antibody rises >2 fold were relatively infrequent following AOM with variation attributable to age of the child and the serotype of Spn. (89)

In a corresponding study, the gradual acquisition over time of antibody to the same five Spn proteins studied here as well as to three NTHi proteins (Protein D, P6 and OMP26) in healthy children was noted. (69;87) In this study, otitis prone children failed to demonstrate or had a significantly slower age related rise in antibody to all five Spn proteins.

In conclusion, these results provide further information on the immunological response of otitis prone children. Immunological hyporesponsiveness in otitis prone children against Spn antigens was observed. Children with AOMTF were also shown to behave immunologically similar to otitis prone children. The administration of a vaccine composition comprising at least one or more of PhtD, PhtE, PcpA, LytB and detoxified pneumolysin (e.g., PlyD1) by the parenteral route (optionally, with an adjuvant) may be used to mitigate the immunological hyporesponsiveness noted following natural exposure to S. pneumoniae.

Example 3

The circulating frequencies of Spn antigen-specific memory B-cells in sera samples obtained from a number of the otitis-prone and non-otitis prone children from the study referenced in Example 1 were assessed and compared. From the total study population of about 387 children, 22 children were studied here: 10 otitis-prone children were identified for study here (based on the availability of sufficient PBMC samples); and 12 non-otitis prone children, with 1 or 2 AOMs and of a similar age to the otitis-prone children were randomly selected to serve as controls. Clinical characteristics of the children are set out in Table 3.

Antigen-specific (PhtD, PhtE, LytB, PcpA, Ply) and total IgG secreting cells were quantified by an (in-house standardized) ELISPOT assay in which memory B-cells were stimulated in vitro to differentiate into antibody-secreting cells (ASC). Briefly, one million thawed PBMC were placed in each well of a 24-well plate containing 1 ml of complete media alone or complete media containing 1 µg/ml of pokeweed mitogen. Cells were kept at 37° C. for 3-days for differentiation, washed with complete media, counted and distributed onto overnight antigen-coated (10 µg/ml) 96-well ELISPOT plates (Millipore). Plasma cell differentiation was optimized with the help of flow cytometric evaluation of the differentiated cells (data not shown). For the detection of total IgG-secreting cells, wells were precoated with monoclonal anti-human IgG (MT91/145; Mabtech) at 10 µg/ml in PBS. As a negative control wells were left untreated or coated with same amount of bovine serum albumin (BSA). Plates were blocked with 10% FBS in RPMI 1640 for 30 min at 37° C. Stimulated PBMC were counted and $5 \times 10^5$ cells were resuspended in 200 µl of fresh complete RPMI media before distributing them onto control and antigen-coated wells. Plates were then incubated at 37° C. in a 5% $CO_2$ incubator overnight and then washed with PBS at least 5-times. Next, 100 µl of 1 µg/ml biotinylated anti-human IgG antibodies (MT78/145; Mabtech) were added to the wells and incubated for an hour. After washing streptavidin-alkaline phosphatase conjugate (1:1000) was added to the wells and incubated for an hour at 37° C. Plates were then washed 5-times with PBS before developing it with substrate (BCIP/NBT; Mabtech). Because of the low frequencies of antigen-specific ASCs, developed spots were manually counted with the help of dissection microscope. Antigen-specific data was expressed as a percentage of antigen-specific memory B-cells and was calculated per million of PBMC as follows: % Ag-specific MBC=(No. antigen-specific spots/No. of total Ig spots)×100.

Antigen-specific IgG titers in the serum of these two groups of children were measured by ELISA performed substantially similar to that described in Example 1, albeit plates were coated with 0.5 µg/ml of antigen and affinity purified goat anti-human IgG, IgM or IgA antibody conjugated to horseradish-peroxidase (Bethyl Laboratories, Inc., Montgomery, Tex.) were used as secondary antibodies.

All data was statistically analyzed using Graph Pad Prism software. Two tailed F values for the data were calculated using Mann Whitney Test.

A summary of the results are set out in FIG. 6 (A, B, C). Percentages of memory B-cells specific to the 5 Spn antigens (PhtD, PhtE, LytB, PcpA, Ply) present in samples from the otitis prone children and non-otitis prone children are shown in FIG. 6A. In sharp contrast to the non-otitis prone group, otitis prone children had a marked reduction of circulating Spn specific memory B-cells after an AOM or NP colonization (FIG. 6A). In particular, significantly lower percentages of memory B-cells producing antigen-specific IgG were observed against antigens PhtD, PhtE and PlyD1 (P<0.02). Otitis prone children also showed an overall lower percentage of memory B-cells specific to LytB, although the difference was not statistically significant (p=0.1). No statistically significant difference was found in the percentage of PcpA-specific memory B-cell in the samples from the otitis prone and the non-otitis prone groups (FIG. 6A). Similarly, the total number of IgG-secreting cells present in the two groups did not differ (data not shown). Serum IgG levels to Spn antigens in the respective groups are shown in FIG. 6B. As compared to the sera from the children in the otitis prone group, IgG titers to PhtD, PcpA and PhtE were significantly higher in the sera from the children in non-otitis group (P<0.05). Ply levels were lower and did not differ in a statistically significant manner between the groups (FIG. 6B). LytB antibody titers were the lowest among all antigens tested in both of the cohorts (FIG. 6B).

In this study, a reduced percentage of memory B-cells circulating in the blood of otitis prone children following AOM and/or NP colonization was noted (FIG. 6A). After encounter of antigen with naive B-cells, antigen-specific memory B-cells and antibody secreting cells are generated in the secondary lymphoid structures that transit through the blood to bone marrow, spleen, or target tissues such as respiratory tract (16). Since serum antibody levels are maintained by memory B-cells (31), by analyzing the percentages of generated antigen-specific memory B-cells, a more precise immunological explanation for lower antibody levels in otitis prone children provided. To confirm the association of lower frequencies of memory B-cells with serum antibody levels, Spn specific antibody titers were measured and found to be significantly lower in otitis prone children (FIG. 6B), similar to the results obtained in the study set out in Example 1 using sera samples from a different cohort of non-otitis prone children (n=15) and otitis-prone children (n=13) following AOM or NP colonization. Overall, the trend of higher Spn antigen specific titer results noted here in non-otitis prone children is consistent with that seen in the cohort evaluated in Example 1, though the exact results in terms of statistically significant differences between groups for antigen specific responses are different in some cases. For example, the small group of children evaluated here did not show any differences in Ply-specific antibody titers. While antibody responses and B-cell generation to a particular protein antigen following bacterial colonization and/or AOM may vary among individual children, a lesser degree of variation is expected with vaccination.

As shown in Example 1, otitis prone children have suboptimal pneumococcal antigen-specific memory CD4+ responses (96). Findings from this study confirm those from the earlier Examples (i.e., that otitis prone children may develop some antibody responses) since antibodies and memory B-cells were detectable among these children after AOM and NP colonization with otopathogens (FIG. 6A-B). However, in the absence of antigen-specific memory B-cell generation and/or memory CD4+ T-cell generation, the antibody levels wane and otitis prone children are unable to maintain adequate serum antibody levels and become susceptible to repeat AOM infections.

Pneumococcal polysaccharide-conjugate vaccination is helpful in boosting protective levels of anti-polysaccharide antibodies (86); however, serotype variation limits the protective efficacy of strain specific anti-polysaccharide antibodies (95). Moreover, despite the fact that otitis prone children can induce serotype specific antibodies to conjugate vaccines, repeated infections are common among this vulnerable group (86), indicating that serotype-neutralizing immunity is brief and incomplete.

Interestingly, the percentage of circulating PhtD specific memory B-cells correlated with serum PhtD levels (FIG. 6C). A difference in the percentages of antigen-specific B-cells and serum antibodies levels to PcpA and PlyD1 was observed (FIG. 6A-B).

In conclusion, in respect of the antigens evaluated here, otitis-prone children have a significantly lower memory B-cell generation that can differentiate into antibody secreting cells. The clinical relevance of the finding is clear. Antigen specific memory B-cells act as reservoirs for scrum antibody maintenance that upon antigen re-encounter can proliferate into ASCs leading to an increase in the serum antibody levels. We found that otitis prone children do not lack total IgG-secreting cells. Furthermore our flow cytometry results showed that in response to polyclonal stimulation, otitis prone children do not have mechanistic dysfunction in the transformation of memory B-cells (CD19+IgD−) to antibody secreting plasma-cells (CD27+CD38+CD138+) (data not shown).

These data show that Spn antigen-specific responses are seen in both non-otitis prone and otitis-prone children following AOM or NP colonization. Although diminished responses are seen in otitis-prone children, responses are nonetheless seen in these children following a natural infection or colonization supporting the administration of a vaccine composition comprising at least one or more of PhtD, PhtE, PcpA, LytB and detoxified pneumolysin (e.g., PlyD1) as described earlier (e.g., Example 2) to mitigate the immunological hyporesponsiveness noted following natural exposure to *S. pneumoniae*.

While example methods, proteins, compositions and other features have been described, it is not the intention of the applicants to restrict or in any way limit the scope of this invention, disclosure or application. Modifications, alterations and variations will be readily apparent to those of skill in the art. Therefore, this disclosure is not limited to the specific details, the representative apparatus and examples shown and described herein. A sequence listing has been filed herewith and is considered part of this disclosure.

The contents of all references cited above are incorporated herein by reference. Use of singular forms herein, such as "a" and "the", does not exclude indication of the corresponding plural form, unless the context indicates to the contrary. Thus, for example, if a claim indicates that use of "a" X or Y, it can also be interpreted as covering use of more than one X or Y unless otherwise indicated. To the extent that the term (or) is used in the description or claims (e.g., A or B) it is intended to mean "A or B or both". In circumstances where the intention is to indicate "only A or B but not both" then the term "only A or B but not both" will be employed. Thus, the term "or" herein is used in the inclusive and not the exclusive sense.

Other embodiments are within the following claims.

TABLE 2*

| Proteins | Group (#) of children | Acute IgG titers (95% Upper & lower confidence interval) | Convalescence | >2 fold increase in antibody at convalescence stage % of children |
|---|---|---|---|---|
| PhtD | Otitis-prone | $1.8 \times 10^5$ | $1.4 \times 10^5$ | 24% |
|  |  | $(4.1 \times 10^4\text{-}7.92 \times 10^5)$ | $(3.9 \times 10^4\text{-}5.1 \times 10^5)$ |  |
|  | AOMTF | $7.9 \times 10^5$ | $8.2 \times 10^5$ | 15% |
|  |  | $(6.3 \times 10^4\text{-}1.0 \times 10^7)$ | $(7.7 \times 10^4\text{-}8.7 \times 10^6)$ |  |
|  | Non otitis-prone | $3.9 \times 10^5$ | $6.1 \times 10^5$ | 35% |
|  |  | $(1.2 \times 10^5\text{-}1.3 \times 10^6)$ | $(1.8 \times 10^5\text{-}2.0 \times 10^6)$ |  |
| LytB | Otitis-prone | $^a$327 | $^a$275 | 20% |
|  |  | (157-682) | (115-658) |  |
|  | AOMTF | $^b$260 | $^b$803 | 33% |
|  |  | (30-2275) | (137-4686) |  |
|  | Non otitis-prone | $^{a,b}$4487 | $^{a,b}$5451 | 33% |
|  |  | $(1711\text{-}1.1 \times 10^4)$ | $(2105\text{-}1.4 \times 10^4)$ |  |
| PcpA | Otitis-prone | $6.6 \times 10^5$ | $6.8 \times 10^5$ | 29% |
|  |  | $(1.39 \times 10^5\text{-}3.16 \times 10^6)$ | $(1.11 \times 10^5\text{-}4.21 \times 10^6)$ |  |
|  | AOMTF | $5.1 \times 10^5$ | $6.9 \times 10^5$ | 36% |
|  |  | $(3.9 \times 10^4\text{-}1.1 \times 10^7)$ | $(8.7 \times 10^4\text{-}2.3 \times 10^7)$ |  |
|  | Non otitis-prone | $4.8 \times 10^5$ | $4.6 \times 10^5$ | 25% |
|  |  | $(1.2 \times 10^5\text{-}1.9 \times 10^6)$ | $(1.2 \times 10^5\text{-}1.7 \times 10^6)$ |  |
| PhtE | Otitis-prone | $^a1.3 \times 10^4$ | $^a1.4 \times 10^4$ | 32% |
|  |  | $(3315\text{-}5.8 \times 10^4)$ | $(3474\text{-}6.3 \times 10^4)$ |  |
|  | AOMTF | $^{b,c}1.8 \times 10^4$ | $^c2.2 \times 10^4$ | 23% |
|  |  | $(3974\text{-}8.6 \times 10^4)$ | $(3374\text{-}1.4 \times 10^5)$ |  |
|  | Non otitis-prone | $^{a,b}1.5 \times 10^5$ | $^a1.1 \times 10^5$ | 19% |
|  |  | $(5.2 \times 10^4\text{-}4.5 \times 10^5)$ | $(3.2 \times 10^4\text{-}4.3 \times 10^5)$ |  |
| PlyD1 | Otitis-prone | $^a1.6 \times 10^4$ | 8578 | 40% |
|  |  | $(5861\text{-}4.4 \times 10^4)$ | $(1852\text{-}3.9 \times 10^4)$ |  |
|  | AOMTF | $1.1 \times 10^4$ | 8534 | 18% |
|  |  | $(2140\text{-}6.0 \times 10^4)$ | $(1675\text{-}4.3 \times 10^4)$ |  |

TABLE 2*-continued

| Proteins | Group (#) of children | Acute IgG titers (95% Upper & lower confidence interval) | Convalescence | >2 fold increase in antibody at convalescence stage % of children |
|---|---|---|---|---|
| | Non otitis-prone | $^a6.45 \times 10^4$ $(3.4 \times 10^4\text{-}1.2 \times 10^5)$ | $5.46 \times 10^4$ $(3.0 \times 10^4\text{-}9.6 \times 10^4)$ | 0% |

*Comparison of geometric mean titer of IgG antibody in the serum samples of 22 otitis prone, 13 AOMTF and 20 non-otitis prone children at their acute vs. convalescence stage.
Significant difference (p value < 0.05) found:
$^a$Otitis prone vs Non-otitis prone;
$^b$AOMTF vs Non-otitis prone;
$^c$Acute vs. convalescence serum

TABLE 3

Characteristics of study subjects

| | Otitis Prone (n = 10) | Non-Otitis Prone (n = 12) | P value |
|---|---|---|---|
| Gender | | | |
| Male | 6 | 7 | 1.00 |
| Female | 4 | 5 | 1.00 |
| Mean Age (mos.) | 13.3 | 12.1 | 0.50 |
| # AOM Episodes | | | |
| ≥3 in 6 months | 5 | 0 | 0.01 |
| ≥4 in 12 months | 5 | 0 | 0.01 |
| Total number of AOM Episodes | | | |
| 1-3 | 3 | 4 | 1.00 |
| 4-5 | 6 | 0 | 0.003 |
| 6 or more | 1 | 0 | 0.45 |
| PET Insertion | 4 | 0 | 0.03 |
| Breast Feeding ≥6 months | 5 | 8 | 0.67 |

REFERENCES

1. Pichichero M E. Recurrent and persistent otitis media. Pediatr. Infect. Dis. J. 2000; 19(9):911-6.
2. Pichichero M E, Casey J R. Otitis media. Expert. Opin. Pharmacother. 2002; 3(8):1073-90.
3. Vergison A, Dagan R, Arguedas A, Bonhoeffer J, Cohen R, Dhooge I et al. Otitis media and its consequences: beyond the earache. Lancet Infect. Dis. 2010; 10(3):195-203.
4. Tecle D W, Klein J O, Rosner B. Epidemiology of otitis media during the first seven years of life in children in greater Boston: a prospective, cohort study. J. Infect. Dis. 1989; 160(1):83-94.
5. Poehling K A, Szilagyi P G, Grijalva C G, Martin S W, LaFleur B, Mitchel E et al. Reduction of frequent otitis media and pressure-equalizing tube insertions in children after introduction of pneumococcal conjugate vaccine. Pediatrics 2007; 119(4):707-15.
6. Del Beccaro M A, Mendelman P M, Inglis A F, Richardson M A, Duncan N O, Clausen C R et al. Bacteriology of acute otitis media: a new perspective. J. Pediatr. 1992; 120(1):81-4.
7. Fietta P, Delsante G. The effector T helper cell triade. Riv. Biol. 2009; 102(1):61-74.
8. Mosmann T R, Sad S. The expanding universe of T-cell subsets: Th1, Th2 and more. Immunol. Today 1996; 17(3):138-46.
9. Mosmann T R, Coffman R L. TH1 and TH2 cells: different patterns of lymphokine secretion lead to different functional properties. Annu. Rev. Immunol. 1989; 7:145-73.
10. Korn T, Bettelli E, Oukka M, Kuchroo V K. IL-17 and Th17 Cells. Annu. Rev. Immunol. 2009; 27:485-517.
11. van Leeuwen E M, Sprent J, Surh C D. Generation and maintenance of memory CD4(+) T Cells. Curr. Opin. Immunol. 2009; 21(2):167-72.
12. McKinstry K K, Strutt T M, Swain S L. The potential of CD4 T-cell memory. Immunology 2010; 130(1):1-9.
13. Combadiere B, Siberil S, Duffy D. Keeping the memory of influenza viruses. Pathol. Biol. (Paris) 2010; 58(2):e79-e86.
14. Lanzavecchia A, Sallusto F. Human B cell memory. Curr. Opin. Immunol. 2009; 21(3):298-304.
15. de Bree G J, Daniels H, Sehilfgaarde M, Jansen H M, Out T A, van Lier R A et al. Characterization of CD4+ memory T cell responses directed against common respiratory pathogens in peripheral blood and lung. J. Infect. Dis. 2007; 195(11):1718-25.
16. Kelly D F, Pollard A J, Moxon E R. Immunological memory: the role of B cells in long-term protection against invasive bacterial pathogens. JAMA 2005; 294 (23):3019-23.
17. Picker L J, Singh M K, Zdraveski Z, Treer J R, Waldrop S L, Bergstresser P R et al. Direct demonstration of cytokine synthesis heterogeneity among human memory/effector T cells by flow cytometry. Blood 1995; 86(4):1408-19.
18. Pitcher C J, Quittner C, Peterson D M, Connors M, Koup R A, Maino V C et al. HIV-1-specific CD4+ T cells are detectable in most individuals with active HIV-1 infection, but decline with prolonged viral suppression. Nat. Med. 1999; 5(5):518-25.
19. Kodama S, Suenaga S, Hirano T, Suzuki M, Mogi G. Induction of specific immunoglobulin A and Th2 immune responses to P6 outer membrane protein of nontypeable Haemophilus influenzae in middle ear mucosa by intranasal immunization. Infect. Immun. 2000; 68(4):2294-300.
20. Malley R, Srivastava A, Lipsitch M, Thompson C M, Watkins C, Tzianabos A et al. Antibody-independent, interleukin-17A-mediated, cross-serotype immunity to pneumococci in mice immunized intranasally with the cell wall polysaccharide. Infect. Immun. 2006; 74(4):2187-95.
21. van den Biggelaar A H, Richmond P C, Pomat W S, Phuanukoonnon S, Nadal-Sims M A, Devitt C J et al. Neonatal pneumococcal conjugate vaccine immunization primes T cells for preferential Th2 cytokine expression: a randomized controlled trial in Papua New Guinea. Vaccine 2009; 27(9):1340-7.
22. Chen S J, Chu M L, Wang C L, Liao C L, Hsieh S L, Sytwu H K et al. Kinetic Th1/Th2 responses of transgenic mice with bacterial meningitis induced by *Haemophilus influenzae*. Clin. Sci. (Lond) 2006; 111(4):253-63.
23. Snapper C M, Shen Y, Khan A Q, Colino J, Zelazowski P, Mond J J et al. Distinct types of T-cell help for the induction of a humoral immune response to *Streptococcus pneumoniae*. Trends Immunol. 2001; 22(6):308-11.
24. Faden H. The microbiologic and immunologic basis for recurrent otitis media in children. Eur. J. Pediatr. 2001; 160(7):407-13.
25. Murphy T F, Yi K. Mechanisms of recurrent otitis media: importance of the immune response to bacterial surface antigens. Ann. N.Y. Acad. Sci. 1997; 830:353-60.
26. Kaur R, Casey J R, Pichichero M E. Serum Antibody Response to Three Non-typeable *Haemophilus influenzae* Outer Membrane Proteins During Acute Otitis Media and Nasopharyngeal Colonization in Otitis Prone and Non-Otitis Prone Children. Vaccine 2011; 29(5):1023-8.
27. Mosmann T R, Schumacher J H, Street N F, Budd R, O'Garra A, Fong T A et al. Diversity of cytokine synthesis and function of mouse CD4+ T cells. Immunol. Rev. 1991; 123:209-29.
28. Rajewsky K. Clonal selection and learning in the antibody system. Nature 1996; 381(6585):751-8.
29. Manz R A, Hauser A E, Hiepe F, Radbruch A. Maintenance of serum antibody levels. Annu. Rev. Immunol. 2005; 23:367-86.
30. Slifka M K, Antia R, Whitmire J K, Ahmed R. Humoral immunity due to long-lived plasma cells. Immunity. 1998; 8(3):363-72.
31. Bernasconi N L, Traggiai E, Lanzavecchia A. Maintenance of serological memory by polyclonal activation of human memory B cells. Science 2002; 298(5601):2199-202.
32. De Las R B, Garcia J L, Lopez R, Garcia P. Purification and polar localization of pneumococcal LytB, a putative endo-beta-N-acetylglucosaminidase: the chain-dispersing murein hydrolase. J. Bactcriol. 2002; 184(18):4988-5000.
33. Kirkham L A, Jefferies J M, Kerr A R, Jing Y, Clarke S C, Smith A et al. Identification of invasive serotype 1 pneumococcal isolates that express nonhemolytic pneumolysin. J. Clin. Microbiol. 2006; 44(1):151-9.
34. Kirkham L A, Kerr A R, Douce G R, Paterson G K, Dilts D A, Liu D F et al. Construction and immunological characterization of a novel nontoxic protective pneumolysin mutant for use in future pneumococcal vaccines. Infect. Immun. 2006; 74(1):586-93.
35. Perfetto S P, Chattopadhyay P K, Lamorcaux L, Nguyen R, Ambrozak D, Koup R A et al. Amine reactive dyes: an effective tool to discriminate live and dead cells in polychromatic flow cytometry. J. Immunol. Methods 2006; 313(1-2):199-208.
36. Waldrop S L, Pitcher C J, Peterson D M, Maino V C, Picker L J. Determination of antigen-specific memory/effector CD4+ T cell frequencies by flow cytometry: evidence for a novel, antigen-specific homeostatic mechanism in HIV-associated immunodeficiency. J. Clin. Invest 1997; 99(7):1739-50.
37. Waldrop S L, Davis K A, Maino V C, Picker U. Normal human CD4+ memory T cells display broad heterogeneity in their activation threshold for cytokine synthesis. J. Immunol. 1998; 161(10):5284-95.
38. Pichichero M E, Dcloria M A, Rennels M B, Anderson E L, Edwards K M, Decker M D et al. A safety and immunogenicity comparison of 12 acellular pertussis vaccines and one whole-cell pertussis vaccine given as a fourth dose in 15- to 20-month-old children. Pediatrics 1997; 100(5):772-88.
39. Adkins B, Bu Y, Guevara P. The generation of Th memory in neonates versus adults: prolonged primary Th2 effector function and impaired development of Th1 memory effector function in murine neonates. J. Immunol. 2001; 166(2):918-25.
40. Holt P G. Functionally mature virus-specific CD8(+) T memory cells in congenitally infected newborns: proof of principle for neonatal vaccination? J. Clin. Invest 2003; 111(11):1645-7.
41. Fleischer B. Superantigens. APMIS 1994; 102(1):3-12.
42. Murcithi M W, Finn A, Ota M O, Zhang Q, Davenport V, Mitchell T J et al. T cell memory response to pneumococcal protein antigens in an area of high pneumococcal carriage and disease. J. Infect. Dis. 2009; 200(5):783-93.
43. Zhang Q, Bagrade L, Bematoniene J, Clarke E, Paton J C, Mitchell T J et al. Low CD4 T cell immunity to pneumolysin is associated with nasopharyngeal carriage of pneumococci in children. J. Infect. Dis. 2007; 195(8):1194-202.
44. Kodama H, Faden H, Harabuchi Y, Kataura A, Bernstein J M, Brodsky L. Cellular immune response of adenoidal and tonsillar lymphocytes to the P6 outer membrane protein of non-typeable *Haemophilus influenzae* and its relation to otitis media. Acta Otolaryngol. 1999; 119(3):377-83.
45. Mattila P S, Nykanen A, Eloranta M, Tarkkanen J. Adenoids provide a microenvironment for the generation of CD4(+), CD45RO(+), L-selectin(−), CXCR4(+), CCR5(+) T lymphocytes, a lymphocyte phenotype found in the middle ear effusion. Int. Immunol. 2000; 12(9):1235-43.
46. Forscni M, Hansson G K, Bagger-Sjoback D, Hultcrantz M. Infiltration of immunocompetent cells in the middle car during acute otitis media: a temporal study. Am. J. Otol. 1999; 20(2):152-7.
47. Skotnicka B, Stasiak-Barmuta A, Hassmann-Poznanska E, Kasprzycka E. Lymphocyte subpopulations in middle ear effusions: flow cytometry analysis. Otol. Neurotol. 2005; 26(4):567-71.
48. Zaghouani H, Hoeman C M, Adkins B. Neonatal immunity: faulty T-helpers and the shortcomings of dendritic cells. Trends Immunol. 2009; 30(12):585-91.
49. Adkins B, Leclerc C, Marshall-Clarke S. Neonatal adaptive immunity comes of age. Nat. Rev. Immunol. 2004; 4(7):553-64.
50. Siegrist C A. Neonatal and early life vaccinology. Vaccine 2001; 19(25-26):3331-46.
51. Tu W, Chen S, Sharp M, Dekker C, Manganello A M, Tongson E C et al. Persistent and selective deficiency of CD4+ T cell immunity to cytomegalovirus in immunocompetent young children. J. Immunol. 2004; 172(5):3260-7.
52. Klein N P, Gans H A, Sung P, Yasukawa L L, Johnson J, Sarafanov A et al. Preterm infants' T cell responses to inactivated poliovirus vaccine. J. Infect. Dis. 2010; 201 (2):214-22.
53. Geiger R, Duhen T, Lanzavccchia A, Sallusto F. Human naive and memory CD4+ T cell repertoires specific for naturally processed antigens analyzed using libraries of amplified T cells. J. Exp. Med. 2009; 206(7):1525-34.
54. Upham J W, Rate A, Rowe J, Kuscl M, Sly P D, Holt P G. Dendritic cell immaturity during infancy restricts the capacity to express vaccine-specific T-cell memory. Infect. Immun. 2006; 74(2):1106-12.

55. Bluestone C D, Stephenson J S, Martin L M. Ten-year review of otitis media pathogens. Pediatr Infect Dis J 1992; 11:S7-11.
56. Luotonen J, Herva E, Karma P, Timonen M, Leinonen M, Makela P H. The bacteriology of acute otitis media in children with special reference to *Streptococcus pneumoniae* as studied by bacteriological and antigen detection methods. Scand. J Infect Dis 1981; 13:177-83.
57. Berkley J A, Lowe B S, Mwangi I et al. Bacteremia among children admitted to a rural hospital in Kenya. N. Engl. J Med. 2005; 352:39-47.
58. Denny F W, Loda F A. Acute respiratory infections are the leading cause of death in children in developing countries. Am. J Trop. Med. Hyg. 1986; 35:1-2.
59. Huang S S, Platt R, Rifas-Shiman S L, Pelton S I, Goldmann D, Finkelstein J A. Post-PCV7 changes in colonizing pneumococcal serotypes in 16 Massachusetts communities, 2001 and 2004. Pediatrics 2005; 116:e408-e413.
60. Kadioglu A, Weiser J N, Paton J C, Andrew P W. The role of *Streptococcus pneumoniae* virulence factors in host respiratory colonization and disease. Nat. Rev. Microbiol. 2008; 6:288-301.
61. Paton J C, Andrew P W, Boulnois G J, Mitchell T J. Molecular analysis of the pathogenicity of *Streptococcus pneumoniae*: the role of pneumococcal proteins. Annu. Rev. Microbiol. 1993; 47:89-115.
62. Ogunniyi A D, Grabowicz M, Mandi L K et al. Pneumococcal histidine triad proteins are regulated by the Zn2+-dependent repressor AdcR and inhibit complement deposition through the recruitment of complement factor H. FASEB J 2009; 23:731-8.
63. Adamou J E, Heinrichs J H, Erwin A L et al. Identification and characterization of a novel family of pneumococcal proteins that are protective against sepsis. Infect Immun. 2001; 69:949-58.
64. Garcia P, Gonzalez M P, Garcia E, Lopez R, Garcia J L. LytB, a novel pneumococcal murcin hydrolase essential for cell separation. Mol. Microbiol. 1999; 31:1275-81.
65. Rosenow C, Ryan P, Weiser J N et al. Contribution of novel choline-binding proteins to adherence, colonization and immunogenicity of *Streptococcus pneumoniae*. Mol. Microbiol. 1997; 25:819-29.
66. Glover D T, Hollingshead S K, Briles D E. *Streptococcus pneumoniae* surface protein PcpA elicits protection against lung infection and fatal sepsis. Infect Immun. 2008; 76:2767-76.
67. Walker J A, Allen R L, Falmagne P, Johnson M K, Boulnois G J. Molecular cloning, characterization, and complete nucleotide sequence of the gene for pneumolysin, the sulfhydryl-activated toxin of *Streptococcus pneumoniae*. Infect Immun. 1987; 55:1184-9.
68. Musher D M, Phan H M, Baughn R E. Protection against bacteremic pneumococcal infection by antibody to pneumolysin. J Infect Dis 2001; 183:827-30.
69. Pichichero M E, Kaur R, Casey J R, Xu Q, Almudevar A, Ochs M. Antibody Response to *Streptococcus pneumoniae* Vaccine Targets PhtD, LytB, PcpA, PhtE and PlyD1 After Nasopharyngeal Colonization and Acute Otitis Media in Children. 10th International Symposium on Recent Advances in Otitis Media. New Orleans La., USA, Abstract J03, page 105, Jun. 5-9, 2011
70. Pelton S I, Leibovitz E. Recent advances in otitis media. Pediatr Infect Dis J 2009; 28:S133-S137.
71. Pichichero M E, Casey J R, Hoberman A, Schwartz R. Pathogens causing recurrent and difficult-to-treat acute otitis media, 2003-2006. Clin. Pediatr (Phila) 2008; 47:901-6.
72. Freijd A, Hammarstrom L, Persson M A, Smith C I. Plasma anti-pneumococcal antibody activity of the IgG class and subclasses in otitis prone children. Clin. Expimmunol. 1984; 56:233-8.
73. Prellner K, Kahn O, Pedersen F K. Pneumococcal antibodies and complement during and after periods of recurrent otitis. Int. J Pediatr Otorhinolaryngol. 1984; 7:39-49.
74. Hotomi M, Yamanaka N, Saito T et al. Antibody responses to the outer membrane protein P6 of nontypeable *Haemophilus influenzae* and pneumococcal capsular polysaccharides in otitis-prone children. Acta Otolaryngol. 1999; 119:703-7.
75. Yamanaka N, Faden H. Antibody response to outer membrane protein of nontypeable *Haemophilus influenzae* in otitis-prone children. J Pediatr 1993; 122:212-8.
76. Yamanaka N, Faden H. Local antibody response to P6 of nontypable *Haemophilus influenzae* in otitis-prone and normal children. Acta Otolaryngol. 1993; 113:524-9.
77. Bernstein J M, Bronson P M, Wilson M E. Immunoglobulin G subclass response to major outer membrane proteins of nontypable *Haemophilus influenzae* in children with acute otitis media. Otolaryngol. Head Neck Surg. 1997; 116:363-71.
78. Giebink G S, Mills E L, Huff J S, Cates K L, Juhn S K, Quie P G. Polymorphonuclear leukocyte dysfunction in children with recurrent otitis media. J Pediatr 1979; 94:13-8.
79. Freijd A, Oxelius V A, Rynnel-Dagoo B. A prospective study demonstrating an association between plasma IgG2 concentrations and susceptibility to otitis media in children. Scand. J Infect Dis 1985; 17:115-20.
80. Veenhoven R, Rijkers G, Schilder A et al. Immunoglobulins in otitis-prone children. Pediatr Res. 2004; 55:159-62.
81. Berman S, Lee B, Nuss R, Roark R, Giclas P C. Immunoglobulin G, total and subclass, in children with or without recurrent otitis media. J Pediatr 1992; 121:249-51.
82. Sharma S, Kaur R, Casey J R, Pichichero M E. Lack of Generation of T Cell Memory to Pneumococcal and *Haemophilus influenzae* Proteins in Early Childhood Explains Immunologic Susceptibility to the Otitis Prone Condition.—(unpublished results).
83. Prellner K, Harsten G, Lofgren B, Christenson B, Heldrup J. Responses to *rubella*, tetanus, and diphtheria vaccines in otitis-prone and non-otitis-prone children. Ann. Otol. Rhinol. Laryngol. 1990; 99:628-32.
84. Wiertsema S P, Sanders E A, Veenhoven R H et al. Antibody levels after regular childhood vaccinations in the immunological screening of children with recurrent otitis media. J Clin. Immunol. 2004; 24:354-60.
85. Breukels M A, Rijkers G T, Voorhorst-Ogink M M, Zegers B J, Sanders L A. Pneumococcal conjugate vaccine primes for polysaccharide-inducible IgG2 antibody response in children with recurrent otitis media acuta. J Infect Dis 1999; 179:1152-6.
86. Barnett E D, Pelton S I, Cabral H J et al. Immune response to pneumococcal conjugate and polysaccharide vaccines in otitis-prone and otitis-free children. Clin. Infect Dis 1999; 29:191-2.
87. Pichichero M E, Kaur R, Casey J R, Sabirov A, Khan M N, Almudevar A. Antibody Response to *Haemophilus influenzae* Outer Membrane Protein D, P6, and OMP26

After Nasopharyngeal Colonization and Acute Otitis Media in Children. Vaccine 2010; 28:7184-92.
88. Rapola S, Kilpi T, Landenkari M, Makela P H, Kayhty H. Antibody response to the pneumococcal proteins pneumococcal surface adhesin A and pneumolysin in children with acute otitis media. Pediatr Infect Dis J 2001; 20:482-7.
89. Soininen A, Landenkari M, Kilpi T, Makela P H, Kayhty H. Antibody response to pneumococcal capsular polysaccharides in children with acute otitis media. Pediatr Infect Dis J 2002; 21:186-92.
90. Soininen A, Pursiaincn H, Kilpi T, Kayhty H. Natural development of antibodies to pneumococcal capsular polysaccharides depends on the serotype: association with pneumococcal carriage and acute otitis media in young children. J Infect Dis 2001; 184:569-76.
91. Zhang Q, Bernatoniene J, Bagrade L et al. Serum and mucosal antibody responses to pneumococcal protein antigens in children: relationships with carriage status. Eur. J Immunol. 2006; 36:46-57.
92. Obaro S K, Adegbola R A, Tharpe J A et al. Pneumococcal surface adhesin A antibody concentration in serum and nasopharyngeal carriage of *Streptococcus pneumoniae* in young African infants. Vaccine 2000; 19:411-2.
93. Holmlund E, Simcll B, Jaakkola T et al. Scrum antibodies to the pneumococcal surface proteins PhtB and PhtE in Finnish infants and adults. Pediatr Infect Dis J 2007; 26:447-9.
94. Holmlund E, Quiambao B, Ollgren J et al. Antibodies to pneumococcal proteins PhtD, CbpA, and LytC in Filipino pregnant women and their infants in relation to pneumococcal carriage. Clin. Vaccine Immunol. 2009; 16:916-23.
95. Casey J R, Adlowitz D G, Pichichero M E. New patterns in the otopathogens causing acute otitis media six to eight years after introduction of pneumococcal conjugate vaccine. Pediatr. Infect. Dis. J. 2010; 29(4):304-9.
96. Sharma S K, Casey J R, Pichichero M E. Reduced memory CD4+ T Cell generation in the circulation of young children may contribute to the Otitis Prone Condition. J. Infect. Dis. 2011.

The invention claimed is:

1. A method of preventing or treating recurrent acute otitis media (AOM) resulting from a *Streptococcus pneumoniae* (*S. Pneumoniae*) infection in a child who is otitis-prone or has had AOM treatment failure, the method comprising administering at least once to said child a therapeutically effective amount of a composition comprising at least one isolated and purified immunogenic polypeptide and optionally at least one adjuvant, the polypeptide being selected from the group consisting of *S. pneumoniae* PhtD (SEQ ID NO:6), PhtE (SEQ ID NO:8), PcpA (SEQ ID NO:3), LytB (SEQ ID NO:11) and detoxified pneumolysin (SEQ ID NO:13).

2. The method of claim 1, wherein the child has acute otitis media.

3. The method of claim 1, wherein administration of the composition elicits or enhances the production or number of, in the child, circulating functional memory CD4⁺T-cells having specificity for *S. pneumoniae*.

4. The method of claim 3, wherein administration of the composition elicits or enhances the production of IFN-γ, IL-4, IL-2 and/or IL-17a by the CD4⁺T-cells following exposure of the cells to the one or more immunogens of the composition.

5. The method of claim 3, wherein the percentage of CD4⁺T-cells producing IFN-γ, IL-4, IL-2 and/or IL-17a in the child following exposure of the cells to one or more immunogens of the composition increases relative to the percentage of such cells existing in the child immediately preceding the administration of the composition.

6. The method of claim 1, wherein administration stimulates the production of IFN-γ, IL-2, IL-4 and/or IL-17a cytokines by CD4⁺T-cells of the child following exposure to the one or more immunogens of the composition.

7. The method of claim 1, wherein the composition comprises an adjuvant.

8. The method of claim 1 wherein the composition comprises at least two, three, four or five of *Streptococcus pneumoniae* PhtD (SEQ ID NO:6), PhtE (SEQ ID NO:8), PcpA (SEQ ID NO:3), LytB (SEQ ID NO:11) and/or detoxified pneumolysin (SEQ ID NO:13).

9. The composition of claim 7 wherein the composition comprises at least two, three, four or five of *Streptococcus pneumoniae* PhtD (SEQ ID NO:6), PhtE (SEQ ID NO:8), PcpA (SEQ ID NO:3), LytB (SEQ ID NO:11) and detoxified pneumolysin (SEQ ID NO:13).

10. The method of claim 1, wherein the child:
has experienced an episode of acute otitis media resulting from a *S. pneumoniae* infection and failed to achieve bacterial eradication and/or resolution of symptoms after at least 48 hours of appropriate antibiotic therapy; and/or
has experienced an episode of acute otitis media (AOM) resulting from a *S. pneumoniae* infection and within 14 days of completing an antibiotic treatment course for the AOM, the symptoms of AOM returned.

11. The method of claim 1 wherein the child has previously received a conjugate vaccine against *S. pneumoniae*.

* * * * *

SEQUENCE LISTING

<160> NUMBER OF SEQ ID NOS: 13

<210> SEQ ID NO 1
<211> LENGTH: 641
<212> TYPE: PRT
<213> ORGANISM: Streptococcus pneumoniae

<400> SEQUENCE: 1

```
Met Lys Lys Thr Thr Ile Leu Ser Leu Thr Thr Ala Ala Val Ile Leu
1               5                   10                  15

Ala Ala Tyr Val Pro Asn Glu Pro Ile Leu Ala Asp Thr Pro Ser Ser
            20                  25                  30

Glu Val Ile Lys Glu Thr Lys Val Gly Ser Ile Ile Gln Gln Asn Asn
        35                  40                  45

Ile Lys Tyr Lys Val Leu Thr Val Glu Gly Asn Ile Arg Thr Val Gln
    50                  55                  60

Val Gly Asn Gly Val Thr Pro Val Glu Phe Glu Ala Gly Gln Asp Gly
65                  70                  75                  80

Lys Pro Phe Thr Ile Pro Thr Lys Ile Thr Val Gly Asp Lys Val Phe
                85                  90                  95

Thr Val Thr Glu Val Ala Ser Gln Ala Phe Ser Tyr Tyr Pro Asp Glu
            100                 105                 110

Thr Gly Arg Ile Val Tyr Tyr Pro Ser Ser Ile Thr Ile Pro Ser Ser
        115                 120                 125

Ile Lys Lys Ile Gln Lys Lys Gly Phe His Gly Ser Lys Ala Lys Thr
    130                 135                 140

Ile Ile Phe Asp Lys Gly Ser Gln Leu Glu Lys Ile Glu Asp Arg Ala
145                 150                 155                 160

Phe Asp Phe Ser Glu Leu Glu Glu Ile Glu Leu Pro Ala Ser Leu Glu
                165                 170                 175

Tyr Ile Gly Thr Ser Ala Phe Ser Phe Ser Gln Lys Leu Lys Lys Leu
            180                 185                 190

Thr Phe Ser Ser Ser Ser Lys Leu Glu Leu Ile Ser His Glu Ala Phe
        195                 200                 205

Ala Asn Leu Ser Asn Leu Glu Lys Leu Thr Leu Pro Lys Ser Val Lys
    210                 215                 220

Thr Leu Gly Ser Asn Leu Phe Arg Leu Thr Thr Ser Leu Lys His Val
```

-continued

```
            225                 230                 235                 240
Asp Val Glu Glu Gly Asn Glu Ser Phe Ala Ser Val Asp Gly Val Leu
                245                 250                 255

Phe Ser Lys Asp Lys Thr Gln Leu Ile Tyr Tyr Pro Ser Gln Lys Asn
                260                 265                 270

Asp Glu Ser Tyr Lys Thr Pro Lys Glu Thr Lys Glu Leu Ala Ser Tyr
                275                 280                 285

Ser Phe Asn Lys Asn Ser Tyr Leu Lys Lys Leu Glu Leu Asn Glu Gly
                290                 295                 300

Leu Glu Lys Ile Gly Thr Phe Ala Phe Ala Asp Ala Ile Lys Leu Glu
305                 310                 315                 320

Glu Ile Ser Leu Pro Asn Ser Leu Glu Thr Ile Glu Arg Leu Ala Phe
                325                 330                 335

Tyr Gly Asn Leu Glu Leu Lys Glu Leu Ile Leu Pro Asn Val Lys
                340                 345                 350

Asn Phe Gly Lys His Val Met Asn Gly Leu Pro Lys Leu Lys Ser Leu
                355                 360                 365

Thr Ile Gly Asn Asn Ile Asn Ser Leu Pro Ser Phe Phe Leu Ser Gly
                370                 375                 380

Val Leu Asp Ser Leu Lys Glu Ile His Ile Lys Asn Lys Ser Thr Glu
385                 390                 395                 400

Phe Ser Val Lys Lys Asp Thr Phe Ala Ile Pro Glu Thr Val Lys Phe
                405                 410                 415

Tyr Val Thr Ser Glu His Ile Lys Asp Val Leu Lys Ser Asn Leu Ser
                420                 425                 430

Thr Ser Asn Asp Ile Ile Val Glu Lys Val Asp Asn Ile Lys Gln Glu
                435                 440                 445

Thr Asp Val Ala Lys Pro Lys Lys Asn Ser Asn Gln Gly Val Val Gly
                450                 455                 460

Trp Val Lys Asp Lys Gly Leu Trp Tyr Tyr Leu Asn Glu Ser Gly Ser
465                 470                 475                 480

Met Ala Thr Gly Trp Val Lys Asp Lys Gly Leu Trp Tyr Tyr Leu Asn
                485                 490                 495

Glu Ser Gly Ser Met Ala Thr Gly Trp Val Lys Asp Lys Gly Leu Trp
                500                 505                 510

Tyr Tyr Leu Asn Glu Ser Gly Ser Met Ala Thr Gly Trp Val Lys Asp
                515                 520                 525

Lys Gly Leu Trp Tyr Tyr Leu Asn Glu Ser Gly Ser Met Ala Thr Gly
                530                 535                 540

Trp Val Lys Asp Lys Gly Leu Trp Tyr Tyr Leu Asn Glu Ser Gly Ser
545                 550                 555                 560

Met Ala Thr Gly Trp Val Lys Asp Lys Gly Leu Trp Tyr Tyr Leu Asn
                565                 570                 575

Glu Ser Gly Ser Met Ala Thr Gly Trp Val Lys Asp Lys Gly Leu Trp
                580                 585                 590

Tyr Tyr Leu Asn Glu Ser Gly Ser Met Ala Thr Gly Trp Phe Thr Val
                595                 600                 605

Ser Gly Lys Trp Tyr Tyr Thr Tyr Asn Ser Gly Asp Leu Leu Val Asn
                610                 615                 620

Thr Thr Thr Pro Asp Gly Tyr Arg Val Asn Ala Asn Gly Glu Trp Val
625                 630                 635                 640

Gly
```

<210> SEQ ID NO 2
<211> LENGTH: 708
<212> TYPE: PRT
<213> ORGANISM: Streptococcus pneumoniae

<400> SEQUENCE: 2

```
Met Lys Lys Thr Thr Ile Leu Ser Leu Thr Ala Ala Val Ile Leu
 1               5                  10                  15

Ala Ala Tyr Val Pro Asn Glu Pro Ile Leu Ala Ala Tyr Val Pro Asn
            20                  25                  30

Glu Pro Ile Leu Ala Asp Thr Pro Ser Ser Glu Val Ile Lys Glu Thr
            35                  40                  45

Lys Val Gly Ser Ile Ile Gln Gln Asn Asn Ile Lys Tyr Lys Val Leu
 50                  55                  60

Thr Val Glu Gly Asn Ile Gly Thr Val Gln Val Gly Asn Gly Val Thr
 65                  70                  75                  80

Pro Val Glu Phe Glu Ala Gly Gln Asp Gly Lys Pro Phe Thr Ile Pro
                85                  90                  95

Thr Lys Ile Thr Val Gly Asp Lys Val Phe Thr Val Thr Glu Val Ala
            100                 105                 110

Ser Gln Ala Phe Ser Tyr Tyr Pro Asp Glu Thr Gly Arg Ile Val Tyr
            115                 120                 125

Tyr Pro Ser Ser Ile Thr Ile Pro Ser Ser Ile Lys Lys Ile Gln Lys
130                 135                 140

Lys Gly Phe His Gly Ser Lys Ala Lys Thr Ile Ile Phe Asp Lys Gly
145                 150                 155                 160

Ser Gln Leu Glu Lys Ile Glu Asp Arg Ala Phe Asp Phe Ser Glu Leu
                165                 170                 175

Glu Glu Ile Glu Leu Pro Ala Ser Leu Glu Tyr Ile Gly Thr Ser Ala
            180                 185                 190

Phe Ser Phe Ser Gln Lys Leu Lys Lys Leu Thr Phe Ser Ser Ser Ser
            195                 200                 205

Lys Leu Glu Leu Ile Ser His Glu Ala Phe Ala Asn Leu Ser Asn Leu
210                 215                 220

Glu Lys Leu Thr Leu Pro Lys Ser Val Lys Thr Leu Gly Ser Asn Leu
225                 230                 235                 240

Phe Arg Leu Thr Thr Ser Leu Asn Met Leu Met Leu Arg Gly Met Ile
                245                 250                 255

Val Ala Ser Val Asp Gly Val Ser Phe Gln Ser Lys Thr Gln Leu Ile
            260                 265                 270

Tyr Tyr Pro Ser Gln Lys Asn Asp Glu Ser Tyr Lys Thr Pro Lys Glu
            275                 280                 285

Thr Lys Glu Leu Ala Ser Tyr Ser Phe Asn Lys Asn Ser Tyr Leu Lys
            290                 295                 300

Lys Leu Glu Leu Asn Glu Gly Leu Gln Lys Ile Gly Thr Phe Ala Phe
305                 310                 315                 320

Ala Asp Ala Thr Lys Leu Glu Glu Ile Ser Leu Pro Asn Ser Leu Glu
                325                 330                 335

Thr Ile Glu Arg Leu Ala Phe Tyr Gly Asn Leu Glu Leu Lys Glu Leu
            340                 345                 350

Ile Leu Pro Asp Asn Val Lys Asn Phe Gly Lys His Val Met Asn Gly
            355                 360                 365

Leu Pro Lys Phe Leu Thr Leu Ser Gly Asn Asn Ile Asn Ser Leu Pro
            370                 375                 380
```

Ser Phe Phe Leu Ser Gly Val Leu Asp Ser Leu Lys Glu Ile His Ile
385                 390                 395                 400

Lys Asn Lys Ser Thr Glu Phe Ser Val Lys Lys Asp Thr Phe Ala Ile
            405                 410                 415

Pro Glu Thr Val Lys Phe Tyr Val Thr Ser Glu His Ile Lys Asp Val
        420                 425                 430

Leu Lys Ser Asn Leu Ser Thr Ser Asn Asp Ile Ile Val Glu Lys Val
            435                 440                 445

Asp Asn Ile Lys Gln Glu Thr Asp Val Ala Lys Pro Lys Lys Asn Ser
        450                 455                 460

Asn Gln Gly Val Val Gly Trp Val Lys Asp Lys Gly Leu Trp Tyr Tyr
465                 470                 475                 480

Leu Asn Glu Ser Gly Ser Met Ala Thr Gly Trp Val Lys Asp Lys Gly
                485                 490                 495

Leu Trp Tyr Tyr Leu Asn Glu Ser Gly Ser Met Ala Thr Gly Trp Val
            500                 505                 510

Lys Asp Lys Gly Leu Trp Tyr Tyr Leu Asn Glu Ser Gly Ser Met Ala
        515                 520                 525

Thr Gly Trp Val Lys Asp Lys Gly Leu Trp Tyr Tyr Leu Asn Glu Ser
    530                 535                 540

Gly Ser Met Ala Thr Gly Trp Val Lys Asp Lys Gly Leu Trp Tyr Tyr
545                 550                 555                 560

Leu Asn Glu Ser Gly Ser Met Ala Thr Gly Trp Val Lys Asp Lys Gly
                565                 570                 575

Leu Trp Tyr Tyr Leu Asn Glu Ser Gly Ser Met Ala Thr Gly Trp Val
            580                 585                 590

Lys Asp Lys Gly Leu Trp Tyr Tyr Leu Asn Glu Ser Gly Ser Met Ala
        595                 600                 605

Thr Gly Trp Val Lys Asp Lys Gly Leu Trp Tyr Tyr Leu Asn Glu Ser
    610                 615                 620

Gly Ser Met Ala Thr Gly Trp Val Lys Asp Lys Gly Leu Trp Tyr Tyr
625                 630                 635                 640

Leu Asn Glu Ser Gly Ser Met Ala Thr Gly Trp Val Lys Asp Lys Gly
                645                 650                 655

Leu Trp Tyr Tyr Leu Asn Glu Ser Gly Ser Met Ala Thr Gly Trp Val
            660                 665                 670

Lys Asp Lys Gly Leu Trp Tyr Tyr Leu Asn Glu Ser Gly Ser Met Ala
        675                 680                 685

Thr Gly Trp Phe Lys Val Ser Gly Lys Trp Tyr Tyr Thr Tyr Asn Ser
    690                 695                 700

Gly Asp Phe Ile
705

<210> SEQ ID NO 3
<211> LENGTH: 445
<212> TYPE: PRT
<213> ORGANISM: Streptococcus pneumoniae

<400> SEQUENCE: 3

Met Ala Asp Thr Pro Ser Ser Glu Val Ile Lys Glu Thr Lys Val Gly
1               5                   10                  15

Ser Ile Ile Gln Gln Asn Asn Ile Lys Tyr Lys Val Leu Thr Val Glu
            20                  25                  30

Gly Asn Ile Gly Thr Val Gln Val Gly Asn Gly Val Thr Pro Val Glu

```
                35                  40                  45
Phe Glu Ala Gly Gln Asp Gly Lys Pro Phe Thr Ile Pro Thr Lys Ile
 50                  55                  60
Thr Val Gly Asp Lys Val Phe Thr Val Thr Glu Val Ala Ser Gln Ala
 65                  70                  75                  80
Phe Ser Tyr Tyr Pro Asp Glu Thr Gly Arg Ile Val Tyr Tyr Pro Ser
                 85                  90                  95
Ser Ile Thr Ile Pro Ser Ser Ile Lys Lys Ile Gln Lys Lys Gly Phe
                100                 105                 110
His Gly Ser Lys Ala Lys Thr Ile Ile Phe Asp Lys Gly Ser Gln Leu
                115                 120                 125
Glu Lys Ile Glu Asp Arg Ala Phe Asp Phe Ser Glu Leu Glu Glu Ile
                130                 135                 140
Glu Leu Pro Ala Ser Leu Glu Tyr Ile Gly Thr Ser Ala Phe Ser Phe
145                 150                 155                 160
Ser Gln Lys Leu Lys Lys Leu Thr Phe Ser Ser Ser Lys Leu Glu
                165                 170                 175
Leu Ile Ser His Glu Ala Phe Ala Asn Leu Ser Asn Leu Glu Lys Leu
                180                 185                 190
Thr Leu Pro Lys Ser Val Lys Thr Leu Gly Ser Asn Leu Phe Arg Leu
                195                 200                 205
Thr Thr Ser Leu Lys His Val Asp Val Glu Glu Gly Asn Glu Ser Phe
                210                 215                 220
Ala Ser Val Asp Gly Val Leu Phe Ser Lys Asp Lys Thr Gln Leu Ile
225                 230                 235                 240
Tyr Tyr Pro Ser Gln Lys Asn Asp Glu Ser Tyr Lys Thr Pro Lys Glu
                245                 250                 255
Thr Lys Glu Leu Ala Ser Tyr Ser Phe Asn Lys Asn Ser Tyr Leu Lys
                260                 265                 270
Lys Leu Glu Leu Asn Glu Gly Leu Glu Lys Ile Gly Thr Phe Ala Phe
                275                 280                 285
Ala Asp Ala Ile Lys Leu Glu Glu Ile Ser Leu Pro Asn Ser Leu Glu
                290                 295                 300
Thr Ile Glu Arg Leu Ala Phe Tyr Gly Asn Leu Glu Leu Lys Glu Leu
305                 310                 315                 320
Ile Leu Pro Asp Asn Val Lys Asn Phe Gly Lys His Val Met Asn Gly
                325                 330                 335
Leu Pro Lys Leu Lys Ser Leu Thr Ile Gly Asn Asn Ile Asn Ser Leu
                340                 345                 350
Pro Ser Phe Phe Leu Ser Gly Val Leu Asp Ser Leu Lys Glu Ile His
                355                 360                 365
Ile Lys Asn Lys Ser Thr Glu Phe Ser Val Lys Lys Asp Thr Phe Ala
                370                 375                 380
Ile Pro Glu Thr Val Lys Phe Tyr Val Thr Ser Glu His Ile Lys Asp
385                 390                 395                 400
Val Leu Lys Ser Asn Leu Ser Thr Ser Asn Asp Ile Ile Val Glu Lys
                405                 410                 415
Val Asp Asn Ile Lys Gln Glu Thr Asp Val Ala Lys Pro Lys Lys Asn
                420                 425                 430
Ser Asn Gln Gly Val Val Gly Trp Val Lys Asp Lys Gly
                435                 440                 445

<210> SEQ ID NO 4
```

<211> LENGTH: 838
<212> TYPE: PRT
<213> ORGANISM: Streptococcus pneumoniae

<400> SEQUENCE: 4

```
Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
        35                  40                  45

Gln Lys Ala Glu Asn Leu Thr Pro Asp Glu Val Ser Lys Arg Glu Gly
    50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Asn Gly Lys Val Pro Tyr
                85                  90                  95

Asp Ala Ile Ile Ser Glu Glu Leu Leu Met Lys Asp Pro Asn Tyr Gln
                100                 105                 110

Leu Lys Asp Ser Asp Ile Val Asn Glu Ile Lys Gly Gly Tyr Val Ile
            115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
            180                 185                 190

Asp Ile Ile Glu Asp Thr Gly Asp Ala Tyr Ile Val Pro His Gly Asp
        195                 200                 205

His Tyr His Tyr Ile Pro Lys Asn Glu Leu Ser Ala Ser Glu Leu Ala
    210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Val Gln Pro Arg Leu Ser Glu Asn
                245                 250                 255

His Asn Leu Thr Val Thr Pro Thr Tyr His Gln Asn Gln Gly Glu Asn
            260                 265                 270

Ile Ser Ser Leu Leu Arg Glu Leu Tyr Ala Lys Pro Leu Ser Glu Arg
        275                 280                 285

His Val Glu Ser Asp Gly Leu Ile Phe Asp Pro Ala Gln Ile Thr Ser
    290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
                325                 330                 335

Ile Pro Leu Arg Tyr Arg Ser Asn His Trp Val Pro Asp Ser Arg Pro
            340                 345                 350

Glu Gln Pro Ser Pro Gln Ser Thr Pro Glu Pro Ser Pro Ser Leu Gln
        355                 360                 365

Pro Ala Pro Asn Pro Gln Pro Ala Pro Ser Asn Pro Ile Asp Glu Lys
    370                 375                 380

Leu Val Lys Glu Ala Val Arg Lys Val Gly Asp Gly Tyr Val Phe Glu
```

-continued

```
            385                 390                 395                 400
        Glu Asn Gly Val Ser Arg Tyr Ile Pro Ala Lys Asp Leu Ser Ala Glu
                            405                 410                 415

Thr Ala Ala Gly Ile Asp Ser Lys Leu Ala Lys Gln Glu Ser Leu Ser
                            420                 425                 430

His Lys Leu Gly Ala Lys Lys Thr Asp Leu Pro Ser Ser Asp Arg Glu
                            435                 440                 445

Phe Tyr Asn Lys Ala Tyr Asp Leu Leu Ala Arg Ile His Gln Asp Leu
                            450                 455                 460

Leu Asp Asn Lys Gly Arg Gln Val Asp Phe Glu Val Leu Asp Asn Leu
        465                 470                 475                 480

Leu Glu Arg Leu Lys Asp Val Ser Ser Asp Lys Val Lys Leu Val Asp
                            485                 490                 495

Asp Ile Leu Ala Phe Leu Ala Pro Ile Arg His Pro Glu Arg Leu Gly
                            500                 505                 510

Lys Pro Asn Ala Gln Ile Thr Tyr Thr Asp Asp Glu Ile Gln Val Ala
                            515                 520                 525

Lys Leu Ala Gly Lys Tyr Thr Thr Glu Asp Gly Tyr Ile Phe Asp Pro
                            530                 535                 540

Arg Asp Ile Thr Ser Asp Glu Gly Asp Ala Tyr Val Thr Pro His Met
        545                 550                 555                 560

Thr His Ser His Trp Ile Lys Lys Asp Ser Leu Ser Glu Ala Glu Arg
                            565                 570                 575

Ala Ala Ala Gln Ala Tyr Ala Lys Glu Lys Gly Leu Thr Pro Pro Ser
                            580                 585                 590

Thr Asp His Gln Asp Ser Gly Asn Thr Glu Ala Lys Gly Ala Glu Ala
                            595                 600                 605

Ile Tyr Asn Arg Val Lys Ala Ala Lys Lys Val Pro Leu Asp Arg Met
                            610                 615                 620

Pro Tyr Asn Leu Gln Tyr Thr Val Glu Val Lys Asn Gly Ser Leu Ile
        625                 630                 635                 640

Ile Pro His Tyr Asp His Tyr His Asn Ile Lys Phe Glu Trp Phe Asp
                            645                 650                 655

Glu Gly Leu Tyr Glu Ala Pro Lys Gly Tyr Ser Leu Glu Asp Leu Leu
                            660                 665                 670

Ala Thr Val Lys Tyr Tyr Val Glu His Pro Asn Glu Arg Pro His Ser
                            675                 680                 685

Asp Asn Gly Phe Gly Asn Ala Ser Asp His Val Arg Lys Asn Lys Ala
        690                 695                 700

Asp Gln Asp Ser Lys Pro Asp Glu Asp Lys Glu His Asp Glu Val Ser
        705                 710                 715                 720

Glu Pro Thr His Pro Glu Ser Asp Glu Lys Glu Asn His Ala Gly Leu
                            725                 730                 735

Asn Pro Ser Ala Asp Asn Leu Tyr Lys Pro Ser Thr Asp Thr Glu Glu
                            740                 745                 750

Thr Glu Glu Glu Ala Glu Asp Thr Thr Asp Glu Ala Glu Ile Pro Gln
                            755                 760                 765

Val Glu Asn Ser Val Ile Asn Ala Lys Ile Ala Asp Ala Glu Ala Leu
                            770                 775                 780

Leu Glu Lys Val Thr Asp Pro Ser Ile Arg Gln Asn Ala Met Glu Thr
        785                 790                 795                 800

Leu Thr Gly Leu Lys Ser Ser Leu Leu Leu Gly Thr Lys Asp Asn Asn
                            805                 810                 815
```

```
Thr Ile Ser Ala Glu Val Asp Ser Leu Leu Ala Leu Leu Lys Glu Ser
            820                 825                 830

Gln Pro Ala Pro Ile Gln
        835
```

<210> SEQ ID NO 5
<211> LENGTH: 839
<212> TYPE: PRT
<213> ORGANISM: Streptococcus pneumoniae

<400> SEQUENCE: 5

```
Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
        35                  40                  45

Gln Lys Ala Glu Asn Leu Thr Pro Asp Glu Val Ser Lys Arg Glu Gly
    50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Asn Gly Lys Val Pro Tyr
                85                  90                  95

Asp Ala Ile Ile Ser Glu Glu Leu Leu Met Lys Asp Pro Asn Tyr Gln
            100                 105                 110

Leu Lys Asp Ser Asp Ile Val Asn Glu Ile Lys Gly Gly Tyr Val Ile
        115                 120                 125

Lys Val Asp Gly Lys Tyr Tyr Val Tyr Leu Lys Asp Ala Ala His Ala
    130                 135                 140

Asp Asn Ile Arg Thr Lys Glu Glu Ile Lys Arg Gln Lys Gln Glu His
145                 150                 155                 160

Ser His Asn His Gly Gly Gly Ser Asn Asp Gln Ala Val Val Ala Ala
                165                 170                 175

Arg Ala Gln Gly Arg Tyr Thr Thr Asp Asp Gly Tyr Ile Phe Asn Ala
            180                 185                 190

Ser Asp Ile Ile Glu Asp Thr Gly Asp Ala Tyr Ile Val Pro His Gly
        195                 200                 205

Asp His Tyr His Tyr Ile Pro Lys Asn Glu Leu Ser Ala Ser Glu Leu
    210                 215                 220

Ala Ala Ala Glu Ala Tyr Trp Asn Gly Lys Gln Gly Ser Arg Pro Ser
225                 230                 235                 240

Ser Ser Ser Ser Tyr Asn Ala Asn Pro Ala Gln Pro Arg Leu Ser Glu
                245                 250                 255

Asn His Asn Leu Thr Val Thr Pro Thr Tyr His Gln Asn Gln Gly Glu
            260                 265                 270

Asn Ile Ser Ser Leu Leu Arg Glu Leu Tyr Ala Lys Pro Leu Ser Glu
        275                 280                 285

Arg His Val Glu Ser Asp Gly Leu Ile Phe Asp Pro Ala Gln Ile Thr
    290                 295                 300

Ser Arg Thr Ala Arg Gly Val Ala Val Pro His Gly Asn His Tyr His
305                 310                 315                 320

Phe Ile Pro Tyr Glu Gln Met Ser Glu Leu Glu Lys Arg Ile Ala Arg
                325                 330                 335

Ile Ile Pro Leu Arg Tyr Arg Ser Asn His Trp Val Pro Asp Ser Arg
```

-continued

```
                340                 345                 350
Pro Glu Gln Pro Ser Pro Gln Ser Thr Pro Glu Pro Ser Pro Ser Pro
                355                 360                 365
Gln Pro Ala Pro Asn Pro Gln Pro Ala Pro Ser Asn Pro Ile Asp Glu
            370                 375                 380
Lys Leu Val Lys Glu Ala Val Arg Lys Val Gly Asp Gly Tyr Val Phe
385                 390                 395                 400
Glu Glu Asn Gly Val Ser Arg Tyr Ile Pro Ala Lys Asp Leu Ser Ala
                405                 410                 415
Glu Thr Ala Ala Gly Ile Asp Ser Lys Leu Ala Lys Gln Glu Ser Leu
            420                 425                 430
Ser His Lys Leu Gly Ala Lys Lys Thr Asp Leu Pro Ser Ser Asp Arg
        435                 440                 445
Glu Phe Tyr Asn Lys Ala Tyr Asp Leu Leu Ala Arg Ile His Gln Asp
        450                 455                 460
Leu Leu Asp Asn Lys Gly Arg Gln Val Asp Phe Glu Ala Leu Asp Asn
465                 470                 475                 480
Leu Leu Glu Arg Leu Lys Asp Val Pro Ser Asp Lys Val Lys Leu Val
                485                 490                 495
Asp Asp Ile Leu Ala Phe Leu Ala Pro Ile Arg His Pro Glu Arg Leu
            500                 505                 510
Gly Lys Pro Asn Ala Gln Ile Thr Tyr Thr Asp Asp Glu Ile Gln Val
        515                 520                 525
Ala Lys Leu Ala Gly Lys Tyr Thr Thr Glu Asp Gly Tyr Ile Phe Asp
        530                 535                 540
Pro Arg Asp Ile Thr Ser Asp Glu Gly Asp Ala Tyr Val Thr Pro His
545                 550                 555                 560
Met Thr His Ser His Trp Ile Lys Lys Asp Ser Leu Ser Glu Ala Glu
                565                 570                 575
Arg Ala Ala Ala Gln Ala Tyr Ala Lys Glu Lys Gly Leu Thr Pro Pro
            580                 585                 590
Ser Thr Asp His Gln Asp Ser Gly Asn Thr Glu Ala Lys Gly Ala Glu
        595                 600                 605
Ala Ile Tyr Asn Arg Val Lys Ala Ala Lys Lys Val Pro Leu Asp Arg
        610                 615                 620
Met Pro Tyr Asn Leu Gln Tyr Thr Val Glu Val Lys Asn Gly Ser Leu
625                 630                 635                 640
Ile Ile Pro His Tyr Asp His Tyr His Asn Ile Lys Phe Glu Trp Phe
                645                 650                 655
Asp Glu Gly Leu Tyr Glu Ala Pro Lys Gly Tyr Thr Leu Glu Asp Leu
            660                 665                 670
Leu Ala Thr Val Lys Tyr Tyr Val Glu His Pro Asn Glu Arg Pro His
        675                 680                 685
Ser Asp Asn Gly Phe Gly Asn Ala Ser Asp His Val Arg Lys Asn Lys
        690                 695                 700
Val Asp Gln Asp Ser Lys Pro Asp Glu Asp Lys Glu His Asp Glu Val
705                 710                 715                 720
Ser Glu Pro Thr His Pro Glu Ser Asp Glu Lys Glu Asn His Ala Gly
                725                 730                 735
Leu Asn Pro Ser Ala Asp Asn Leu Tyr Lys Pro Ser Thr Asp Thr Glu
            740                 745                 750
Glu Thr Glu Glu Glu Ala Glu Asp Thr Thr Asp Glu Ala Glu Ile Pro
        755                 760                 765
```

```
Gln Val Glu Asn Ser Val Ile Asn Ala Lys Ile Ala Asp Ala Glu Ala
    770             775                 780

Leu Leu Glu Lys Val Thr Asp Pro Ser Ile Arg Gln Asn Ala Met Glu
785             790                 795                 800

Thr Leu Thr Gly Leu Lys Ser Ser Leu Leu Gly Thr Lys Asp Asn
                805                 810                 815

Asn Thr Ile Ser Ala Glu Val Asp Ser Leu Leu Ala Leu Leu Lys Glu
            820                 825                 830

Ser Gln Pro Ala Pro Ile Gln
        835

<210> SEQ ID NO 6
<211> LENGTH: 820
<212> TYPE: PRT
<213> ORGANISM: Streptococcus pneumoniae

<400> SEQUENCE: 6

Met Gly Ser Tyr Glu Leu Gly Arg His Gln Ala Gly Gln Val Lys Lys
1               5                   10                  15

Glu Ser Asn Arg Val Ser Tyr Ile Asp Gly Asp Gln Ala Gly Gln Lys
            20                  25                  30

Ala Glu Asn Leu Thr Pro Asp Glu Val Ser Lys Arg Glu Gly Ile Asn
        35                  40                  45

Ala Glu Gln Ile Val Ile Lys Ile Thr Asp Gln Gly Tyr Val Thr Ser
    50                  55                  60

His Gly Asp His Tyr His Tyr Tyr Asn Gly Lys Val Pro Tyr Asp Ala
65              70                  75                  80

Ile Ile Ser Glu Glu Leu Leu Met Lys Asp Pro Asn Tyr Gln Leu Lys
                85                  90                  95

Asp Ser Asp Ile Val Asn Glu Ile Lys Gly Gly Tyr Val Ile Lys Val
            100                 105                 110

Asp Gly Lys Tyr Tyr Val Tyr Leu Lys Asp Ala Ala His Ala Asp Asn
        115                 120                 125

Ile Arg Thr Lys Glu Glu Ile Lys Arg Gln Lys Gln Glu His Ser His
    130                 135                 140

Asn His Asn Ser Arg Ala Asp Asn Ala Val Ala Ala Arg Ala Gln
145             150                 155                 160

Gly Arg Tyr Thr Thr Asp Asp Gly Tyr Ile Phe Asn Ala Ser Asp Ile
                165                 170                 175

Ile Glu Asp Thr Gly Asp Ala Tyr Ile Val Pro His Gly Asp His Tyr
            180                 185                 190

His Tyr Ile Pro Lys Asn Glu Leu Ser Ala Ser Glu Leu Ala Ala Ala
        195                 200                 205

Glu Ala Tyr Trp Asn Gly Lys Gln Gly Ser Arg Pro Ser Ser Ser Ser
    210                 215                 220

Ser Tyr Asn Ala Asn Pro Val Gln Pro Arg Leu Ser Glu Asn His Asn
225             230                 235                 240

Leu Thr Val Thr Pro Thr Tyr His Gln Asn Gln Gly Glu Asn Ile Ser
                245                 250                 255

Ser Leu Leu Arg Glu Leu Tyr Ala Lys Pro Leu Ser Glu Arg His Val
            260                 265                 270

Glu Ser Asp Gly Leu Ile Phe Asp Pro Ala Gln Ile Thr Ser Arg Thr
        275                 280                 285

Ala Arg Gly Val Ala Val Pro His Gly Asn His Tyr His Phe Ile Pro
```

-continued

```
            290                 295                 300
Tyr Glu Gln Met Ser Glu Leu Glu Lys Arg Ile Ala Arg Ile Ile Pro
305                 310                 315                 320

Leu Arg Tyr Arg Ser Asn His Trp Val Pro Asp Ser Arg Pro Glu Gln
                325                 330                 335

Pro Ser Pro Gln Ser Thr Pro Glu Pro Ser Pro Ser Leu Gln Pro Ala
            340                 345                 350

Pro Asn Pro Gln Pro Ala Pro Ser Asn Pro Ile Asp Glu Lys Leu Val
            355                 360                 365

Lys Glu Ala Val Arg Lys Val Gly Asp Gly Tyr Val Phe Glu Glu Asn
    370                 375                 380

Gly Val Ser Arg Tyr Ile Pro Ala Lys Asp Leu Ser Ala Glu Thr Ala
385                 390                 395                 400

Ala Gly Ile Asp Ser Lys Leu Ala Lys Gln Glu Ser Leu Ser His Lys
                405                 410                 415

Leu Gly Ala Lys Lys Thr Asp Leu Pro Ser Ser Asp Arg Glu Phe Tyr
                420                 425                 430

Asn Lys Ala Tyr Asp Leu Leu Ala Arg Ile His Gln Asp Leu Leu Asp
            435                 440                 445

Asn Lys Gly Arg Gln Val Asp Phe Glu Val Leu Asp Asn Leu Leu Glu
            450                 455                 460

Arg Leu Lys Asp Val Ser Ser Asp Lys Val Lys Leu Val Asp Asp Ile
465                 470                 475                 480

Leu Ala Phe Leu Ala Pro Ile Arg His Pro Glu Arg Leu Gly Lys Pro
                485                 490                 495

Asn Ala Gln Ile Thr Tyr Thr Asp Asp Glu Ile Gln Val Ala Lys Leu
            500                 505                 510

Ala Gly Lys Tyr Thr Thr Glu Asp Gly Tyr Ile Phe Asp Pro Arg Asp
            515                 520                 525

Ile Thr Ser Asp Glu Gly Asp Ala Tyr Val Thr Pro His Met Thr His
530                 535                 540

Ser His Trp Ile Lys Lys Asp Ser Leu Ser Glu Ala Glu Arg Ala Ala
545                 550                 555                 560

Ala Gln Ala Tyr Ala Lys Glu Lys Gly Leu Thr Pro Pro Ser Thr Asp
                565                 570                 575

His Gln Asp Ser Gly Asn Thr Glu Ala Lys Gly Ala Glu Ala Ile Tyr
            580                 585                 590

Asn Arg Val Lys Ala Ala Lys Lys Val Pro Leu Asp Arg Met Pro Tyr
            595                 600                 605

Asn Leu Gln Tyr Thr Val Glu Val Lys Asn Gly Ser Leu Ile Ile Pro
610                 615                 620

His Tyr Asp His Tyr His Asn Ile Lys Phe Glu Trp Phe Asp Glu Gly
625                 630                 635                 640

Leu Tyr Glu Ala Pro Lys Gly Tyr Ser Leu Glu Asp Leu Leu Ala Thr
                645                 650                 655

Val Lys Tyr Tyr Val Glu His Pro Asn Glu Arg Pro His Ser Asp Asn
            660                 665                 670

Gly Phe Gly Asn Ala Ser Asp His Val Arg Lys Asn Lys Ala Asp Gln
            675                 680                 685

Asp Ser Lys Pro Asp Glu Asp Lys Glu His Asp Glu Val Ser Glu Pro
            690                 695                 700

Thr His Pro Glu Ser Asp Glu Lys Glu Asn His Ala Gly Leu Asn Pro
705                 710                 715                 720
```

-continued

Ser Ala Asp Asn Leu Tyr Lys Pro Ser Thr Asp Thr Glu Thr Glu
                725                 730                 735

Glu Glu Ala Glu Asp Thr Thr Asp Glu Ala Ile Pro Gln Val Glu
            740                 745                 750

Asn Ser Val Ile Asn Ala Lys Ile Ala Asp Ala Glu Ala Leu Leu Glu
        755                 760                 765

Lys Val Thr Asp Pro Ser Ile Arg Gln Asn Ala Met Glu Thr Leu Thr
770                 775                 780

Gly Leu Lys Ser Ser Leu Leu Gly Thr Lys Asp Asn Asn Thr Ile
785                 790                 795                 800

Ser Ala Glu Val Asp Ser Leu Leu Ala Leu Leu Lys Ser Gln Pro
            805                 810                 815

Ala Pro Ile Gln
            820

<210> SEQ ID NO 7
<211> LENGTH: 1039
<212> TYPE: PRT
<213> ORGANISM: Streptococcus pneumoniae

<400> SEQUENCE: 7

Met Lys Phe Ser Lys Lys Tyr Ile Ala Ala Gly Ser Ala Val Ile Val
1               5                   10                  15

Ser Leu Ser Leu Cys Ala Tyr Ala Leu Asn Gln His Arg Ser Gln Glu
            20                  25                  30

Asn Lys Asp Asn Asn Arg Val Ser Tyr Val Asp Gly Ser Gln Ser Ser
        35                  40                  45

Gln Lys Ser Glu Asn Leu Thr Pro Asp Gln Val Ser Gln Lys Glu Gly
    50                  55                  60

Ile Gln Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Leu Phe Ser Glu Glu Leu Leu Met Lys Asp Pro Asn Tyr Gln
            100                 105                 110

Leu Lys Asp Ala Asp Ile Val Asn Glu Val Lys Gly Gly Tyr Ile Ile
        115                 120                 125

Lys Val Asp Gly Lys Tyr Tyr Val Tyr Leu Lys Asp Ala Ala His Ala
    130                 135                 140

Asp Asn Val Arg Thr Lys Asp Glu Ile Asn Arg Gln Lys Gln Glu His
145                 150                 155                 160

Val Lys Asp Asn Glu Lys Val Asn Ser Asn Val Ala Val Ala Arg Ser
                165                 170                 175

Gln Gly Arg Tyr Thr Thr Asn Asp Gly Tyr Val Phe Asn Pro Ala Asp
            180                 185                 190

Ile Ile Glu Asp Thr Gly Asn Ala Tyr Ile Val Pro His Gly Gly His
        195                 200                 205

Tyr His Tyr Ile Pro Lys Ser Asp Leu Ser Ala Ser Glu Leu Ala Ala
    210                 215                 220

Ala Lys Ala His Leu Ala Gly Lys Asn Met Gln Pro Ser Gln Leu Ser
225                 230                 235                 240

Tyr Ser Ser Thr Ala Ser Asp Asn Asn Thr Gln Ser Val Ala Lys Gly
                245                 250                 255

Ser Thr Ser Lys Pro Ala Asn Lys Ser Glu Asn Leu Gln Ser Leu Leu

-continued

```
                260                 265                 270
Lys Glu Leu Tyr Asp Ser Pro Ser Ala Gln Arg Tyr Ser Glu Ser Asp
            275                 280                 285

Gly Leu Val Phe Asp Pro Ala Lys Ile Ile Ser Arg Thr Pro Asn Gly
            290                 295                 300

Val Ala Ile Pro His Gly Asp His Tyr His Phe Ile Pro Tyr Ser Lys
305                 310                 315                 320

Leu Ser Ala Leu Glu Glu Lys Ile Ala Arg Met Val Pro Ile Ser Gly
            325                 330                 335

Thr Gly Ser Thr Val Ser Thr Asn Ala Lys Pro Asn Glu Val Val Ser
            340                 345                 350

Ser Leu Gly Ser Leu Ser Ser Asn Pro Ser Ser Leu Thr Thr Ser Lys
            355                 360                 365

Glu Leu Ser Ser Ala Ser Asp Gly Tyr Ile Phe Asn Pro Lys Asp Ile
            370                 375                 380

Val Glu Glu Thr Ala Thr Ala Tyr Ile Val Arg His Gly Asp His Phe
385                 390                 395                 400

His Tyr Ile Pro Lys Ser Asn Gln Ile Gly Gln Pro Thr Leu Pro Asn
            405                 410                 415

Asn Ser Leu Ala Thr Pro Ser Pro Ser Leu Pro Ile Asn Pro Gly Thr
            420                 425                 430

Ser His Glu Lys His Glu Glu Asp Gly Tyr Gly Phe Asp Ala Asn Arg
            435                 440                 445

Ile Ile Ala Glu Asp Glu Ser Gly Phe Val Met Ser His Gly Asp His
            450                 455                 460

Asn His Tyr Phe Phe Lys Lys Asp Leu Thr Glu Glu Gln Ile Lys Ala
465                 470                 475                 480

Ala Gln Lys His Leu Glu Glu Val Lys Thr Ser His Asn Gly Leu Asp
            485                 490                 495

Ser Leu Ser Ser His Glu Gln Asp Tyr Pro Ser Asn Ala Lys Glu Met
            500                 505                 510

Lys Asp Leu Asp Lys Lys Ile Glu Glu Lys Ile Ala Gly Ile Met Lys
            515                 520                 525

Gln Tyr Gly Val Lys Arg Glu Ser Ile Val Val Asn Lys Glu Lys Asn
            530                 535                 540

Ala Ile Ile Tyr Pro His Gly Asp His His Ala Asp Pro Ile Asp
545                 550                 555                 560

Glu His Lys Pro Val Gly Ile Gly His Ser His Ser Asn Tyr Glu Leu
            565                 570                 575

Phe Lys Pro Glu Glu Gly Val Ala Lys Lys Glu Gly Asn Lys Val Tyr
            580                 585                 590

Thr Gly Glu Glu Leu Thr Asn Val Val Asn Leu Leu Lys Asn Ser Thr
            595                 600                 605

Phe Asn Asn Gln Asn Phe Thr Leu Ala Asn Gly Gln Lys Arg Val Ser
            610                 615                 620

Phe Ser Phe Pro Pro Glu Leu Glu Lys Lys Leu Gly Ile Asn Met Leu
625                 630                 635                 640

Val Lys Leu Ile Thr Pro Asp Gly Lys Val Leu Glu Lys Val Ser Gly
            645                 650                 655

Lys Val Phe Gly Glu Gly Val Gly Asn Ile Ala Asn Phe Glu Leu Asp
            660                 665                 670

Gln Pro Tyr Leu Pro Gly Gln Thr Phe Lys Tyr Thr Ile Ala Ser Lys
            675                 680                 685
```

Asp Tyr Pro Glu Val Ser Tyr Asp Gly Thr Phe Thr Val Pro Thr Ser
            690                 695                 700

Leu Ala Tyr Lys Met Ala Ser Gln Thr Ile Phe Tyr Pro Phe His Ala
705                 710                 715                 720

Gly Asp Thr Tyr Leu Arg Val Asn Pro Gln Phe Ala Val Pro Lys Gly
                725                 730                 735

Thr Asp Ala Leu Val Arg Val Phe Asp Glu Phe His Gly Asn Ala Tyr
            740                 745                 750

Leu Glu Asn Asn Tyr Lys Val Gly Glu Ile Lys Leu Pro Ile Pro Lys
        755                 760                 765

Leu Asn Gln Gly Thr Thr Arg Thr Ala Gly Asn Lys Ile Pro Val Thr
770                 775                 780

Phe Met Ala Asn Ala Tyr Leu Asp Asn Gln Ser Thr Tyr Ile Val Glu
785                 790                 795                 800

Val Pro Ile Leu Glu Lys Glu Asn Gln Thr Asp Lys Pro Ser Ile Leu
                805                 810                 815

Pro Gln Phe Lys Arg Asn Lys Ala Gln Glu Asn Leu Lys Leu Asp Glu
                820                 825                 830

Lys Val Glu Glu Pro Lys Thr Ser Glu Lys Val Glu Lys Glu Lys Leu
            835                 840                 845

Ser Glu Thr Gly Asn Ser Thr Ser Asn Ser Thr Leu Glu Glu Val Pro
850                 855                 860

Thr Val Asp Pro Val Gln Glu Lys Val Ala Lys Phe Ala Glu Ser Tyr
865                 870                 875                 880

Gly Met Lys Leu Glu Asn Val Leu Phe Asn Met Asp Gly Thr Ile Glu
                885                 890                 895

Leu Tyr Leu Pro Ser Gly Glu Val Ile Lys Lys Asn Met Ala Asp Phe
            900                 905                 910

Thr Gly Glu Ala Pro Gln Gly Asn Gly Glu Asn Lys Pro Ser Glu Asn
        915                 920                 925

Gly Lys Val Ser Thr Gly Thr Val Glu Asn Gln Pro Thr Glu Asn Lys
930                 935                 940

Pro Ala Asp Ser Leu Pro Glu Ala Pro Asn Glu Lys Pro Val Lys Pro
945                 950                 955                 960

Glu Asn Ser Thr Asp Asn Gly Met Leu Asn Pro Glu Gly Asn Val Gly
                965                 970                 975

Ser Asp Pro Met Leu Asp Pro Ala Leu Glu Glu Ala Pro Ala Val Asp
            980                 985                 990

Pro Val Gln Glu Lys Leu Glu Lys Phe Thr Ala Ser Tyr Gly Leu Gly
        995                 1000                1005

Leu Asp Ser Val Ile Phe Asn Met Asp Gly Thr Ile Glu Leu Arg
        1010                1015                1020

Leu Pro Ser Gly Glu Val Ile Lys Lys Asn Leu Ser Asp Leu Ile
        1025                1030                1035

Ala

<210> SEQ ID NO 8
<211> LENGTH: 810
<212> TYPE: PRT
<213> ORGANISM: Streptococcus pneumoniae

<400> SEQUENCE: 8

Met Gly Lys Asn Met Gln Pro Ser Gln Leu Ser Tyr Ser Ser Thr Ala
1               5                   10                  15

```
Ser Asp Asn Asn Thr Gln Ser Val Ala Lys Gly Ser Thr Ser Lys Pro
            20                  25                  30

Ala Asn Lys Ser Glu Asn Leu Gln Ser Leu Leu Lys Glu Leu Tyr Asp
        35                  40                  45

Ser Pro Ser Ala Gln Arg Tyr Ser Glu Ser Asp Gly Leu Val Phe Asp
50                  55                  60

Pro Ala Lys Ile Ile Ser Arg Thr Pro Asn Gly Val Ala Ile Pro His
65                  70                  75                  80

Gly Asp His Tyr His Phe Ile Pro Tyr Ser Lys Leu Ser Ala Leu Glu
                85                  90                  95

Glu Lys Ile Ala Arg Met Val Pro Ile Ser Gly Thr Gly Ser Thr Val
            100                 105                 110

Ser Thr Asn Ala Lys Pro Asn Glu Val Val Ser Ser Leu Gly Ser Leu
        115                 120                 125

Ser Ser Asn Pro Ser Ser Leu Thr Thr Ser Lys Glu Leu Ser Ser Ala
130                 135                 140

Ser Asp Gly Tyr Ile Phe Asn Pro Lys Asp Ile Val Glu Glu Thr Ala
145                 150                 155                 160

Thr Ala Tyr Ile Val Arg His Gly Asp His Phe His Tyr Ile Pro Lys
                165                 170                 175

Ser Asn Gln Ile Gly Gln Pro Thr Leu Pro Asn Asn Ser Leu Ala Thr
            180                 185                 190

Pro Ser Pro Ser Leu Pro Ile Asn Pro Gly Thr Ser His Glu Lys His
        195                 200                 205

Glu Glu Asp Gly Tyr Gly Phe Asp Ala Asn Arg Ile Ile Ala Glu Asp
210                 215                 220

Glu Ser Gly Phe Val Met Ser His Gly Asp His Asn His Tyr Phe Phe
225                 230                 235                 240

Lys Lys Asp Leu Thr Glu Glu Gln Ile Lys Ala Ala Gln Lys His Leu
                245                 250                 255

Glu Glu Val Lys Thr Ser His Asn Gly Leu Asp Ser Leu Ser Ser His
            260                 265                 270

Glu Gln Asp Tyr Pro Gly Asn Ala Lys Glu Met Lys Asp Leu Asp Lys
        275                 280                 285

Lys Ile Glu Glu Lys Ile Ala Gly Ile Met Lys Gln Tyr Gly Val Lys
290                 295                 300

Arg Glu Ser Ile Val Val Asn Lys Glu Lys Asn Ala Ile Ile Tyr Pro
305                 310                 315                 320

His Gly Asp His His His Ala Asp Pro Ile Asp Glu His Lys Pro Val
                325                 330                 335

Gly Ile Gly His Ser His Ser Asn Tyr Glu Leu Phe Lys Pro Glu Glu
            340                 345                 350

Gly Val Ala Lys Lys Glu Gly Asn Lys Val Tyr Thr Gly Glu Glu Leu
        355                 360                 365

Thr Asn Val Val Asn Leu Leu Lys Asn Ser Thr Phe Asn Asn Gln Asn
370                 375                 380

Phe Thr Leu Ala Asn Gly Gln Lys Arg Val Ser Phe Ser Phe Pro Pro
385                 390                 395                 400

Glu Leu Glu Lys Lys Leu Gly Ile Asn Met Leu Val Lys Leu Ile Thr
                405                 410                 415

Pro Asp Gly Lys Val Leu Glu Lys Val Ser Gly Lys Val Phe Gly Glu
            420                 425                 430
```

Gly Val Gly Asn Ile Ala Asn Phe Glu Leu Asp Gln Pro Tyr Leu Pro
            435                 440                 445

Gly Gln Thr Phe Lys Tyr Thr Ile Ala Ser Lys Asp Tyr Pro Glu Val
    450                 455                 460

Ser Tyr Asp Gly Thr Phe Thr Val Pro Thr Ser Leu Ala Tyr Lys Met
465                 470                 475                 480

Ala Ser Gln Thr Ile Phe Tyr Pro Phe His Ala Gly Asp Thr Tyr Leu
                485                 490                 495

Arg Val Asn Pro Gln Phe Ala Val Pro Lys Gly Thr Asp Ala Leu Val
            500                 505                 510

Arg Val Phe Asp Glu Phe His Gly Asn Ala Tyr Leu Glu Asn Asn Tyr
        515                 520                 525

Lys Val Gly Glu Ile Lys Leu Pro Ile Pro Lys Leu Asn Gln Gly Thr
    530                 535                 540

Thr Arg Thr Ala Gly Asn Lys Ile Pro Val Thr Phe Met Ala Asn Ala
545                 550                 555                 560

Tyr Leu Asp Asn Gln Ser Thr Tyr Ile Val Glu Val Pro Ile Leu Glu
                565                 570                 575

Lys Glu Asn Gln Thr Asp Lys Pro Ser Ile Leu Pro Gln Phe Lys Arg
            580                 585                 590

Asn Lys Ala Gln Glu Asn Ser Lys Leu Asp Glu Lys Val Glu Glu Pro
        595                 600                 605

Lys Thr Ser Glu Lys Val Glu Lys Lys Leu Ser Glu Thr Gly Asn
    610                 615                 620

Ser Thr Ser Asn Ser Thr Leu Glu Glu Val Pro Thr Val Asp Pro Val
625                 630                 635                 640

Gln Glu Lys Val Ala Lys Phe Ala Glu Ser Tyr Gly Met Lys Leu Glu
                645                 650                 655

Asn Val Leu Phe Asn Met Asp Gly Thr Ile Glu Leu Tyr Leu Pro Ser
            660                 665                 670

Gly Glu Val Ile Lys Lys Asn Met Ala Asp Phe Thr Gly Glu Ala Pro
        675                 680                 685

Gln Gly Asn Gly Glu Asn Lys Pro Ser Glu Asn Gly Lys Val Ser Thr
    690                 695                 700

Gly Thr Val Glu Asn Gln Pro Thr Glu Asn Lys Pro Ala Asp Ser Leu
705                 710                 715                 720

Pro Glu Ala Pro Asn Glu Lys Pro Val Lys Pro Glu Asn Ser Thr Asp
                725                 730                 735

Asn Gly Met Leu Asn Pro Glu Gly Asn Val Gly Ser Pro Met Leu
            740                 745                 750

Asp Pro Ala Leu Glu Glu Ala Pro Ala Val Asp Pro Val Gln Glu Lys
        755                 760                 765

Leu Glu Lys Phe Thr Ala Ser Tyr Gly Leu Gly Leu Asp Ser Val Ile
    770                 775                 780

Phe Asn Met Asp Gly Thr Ile Glu Leu Arg Leu Pro Ser Gly Glu Val
785                 790                 795                 800

Ile Lys Lys Asn Leu Ser Asp Phe Ile Ala
                805                 810

<210> SEQ ID NO 9
<211> LENGTH: 702
<212> TYPE: PRT
<213> ORGANISM: Streptococcus pneumoniae

<400> SEQUENCE: 9

-continued

```
Met Lys Lys Val Arg Phe Ile Phe Leu Ala Leu Leu Phe Leu Ala
1               5                   10                  15

Ser Pro Glu Gly Ala Met Ala Ser Asp Gly Thr Trp Gln Gly Lys Gln
            20                  25                  30

Tyr Leu Lys Glu Asp Gly Ser Gln Ala Ala Asn Glu Trp Val Phe Asp
            35                  40                  45

Thr His Tyr Gln Ser Trp Phe Tyr Ile Lys Ala Asp Ala Asn Tyr Ala
        50                  55                  60

Glu Asn Glu Trp Leu Lys Gln Gly Asp Asp Tyr Phe Tyr Leu Lys Ser
65                  70                  75                  80

Gly Gly Tyr Met Ala Lys Ser Glu Trp Val Glu Asp Lys Gly Ala Phe
                85                  90                  95

Tyr Tyr Leu Asp Gln Asp Gly Lys Met Lys Arg Asn Ala Trp Val Gly
                100                 105                 110

Thr Ser Tyr Val Gly Ala Thr Gly Ala Lys Val Ile Glu Asp Trp Val
            115                 120                 125

Tyr Asp Ser Gln Tyr Asp Ala Trp Phe Tyr Ile Lys Ala Asp Gly Gln
130                 135                 140

His Ala Glu Lys Glu Trp Leu Gln Ile Lys Gly Lys Asp Tyr Tyr Phe
145                 150                 155                 160

Lys Ser Gly Gly Tyr Leu Leu Thr Ser Gln Trp Ile Asn Gln Ala Tyr
                165                 170                 175

Val Asn Ala Ser Gly Ala Lys Val Gln Gln Gly Trp Leu Phe Asp Lys
                180                 185                 190

Gln Tyr Gln Ser Trp Phe Tyr Ile Lys Glu Asn Gly Asn Tyr Ala Asp
            195                 200                 205

Lys Glu Trp Ile Phe Glu Asn Gly His Tyr Tyr Leu Lys Ser Gly
210                 215                 220

Gly Tyr Met Ala Ala Asn Glu Trp Ile Trp Asp Lys Glu Ser Trp Phe
225                 230                 235                 240

Tyr Leu Lys Phe Asp Gly Lys Ile Ala Glu Lys Glu Trp Val Tyr Asp
                245                 250                 255

Ser His Ser Gln Ala Trp Tyr Tyr Phe Lys Ser Gly Tyr Met Ala
            260                 265                 270

Ala Asn Glu Trp Ile Trp Asp Lys Glu Ser Trp Phe Tyr Leu Lys Phe
275                 280                 285

Asp Gly Lys Met Ala Glu Lys Glu Trp Val Tyr Asp Ser His Ser Gln
        290                 295                 300

Ala Trp Tyr Tyr Phe Lys Ser Gly Gly Tyr Met Thr Ala Asn Glu Trp
305                 310                 315                 320

Ile Trp Asp Lys Glu Ser Trp Phe Tyr Leu Lys Ser Asp Gly Lys Ile
                325                 330                 335

Ala Glu Lys Glu Trp Val Tyr Asp Ser His Ser Gln Ala Trp Tyr Tyr
            340                 345                 350

Phe Lys Ser Gly Gly Tyr Met Thr Ala Asn Glu Trp Ile Trp Asp Lys
            355                 360                 365

Glu Ser Trp Phe Tyr Leu Lys Ser Asp Gly Lys Met Ala Glu Lys Glu
        370                 375                 380

Trp Val Tyr Asp Ser His Ser Gln Ala Trp Tyr Tyr Phe Lys Ser Gly
385                 390                 395                 400

Gly Tyr Met Ala Lys Asn Glu Thr Val Asp Gly Tyr Gln Leu Gly Ser
                405                 410                 415
```

```
Asp Gly Lys Trp Leu Gly Lys Ala Thr Asn Lys Asn Ala Ala Tyr
            420                 425                 430
Tyr Gln Val Val Pro Val Thr Ala Asn Val Tyr Asp Ser Asp Gly Glu
        435                 440                 445
Lys Leu Ser Tyr Ile Ser Gln Gly Ser Val Val Trp Leu Asp Lys Asp
    450                 455                 460
Arg Lys Ser Asp Asp Lys Arg Leu Ala Ile Thr Ile Ser Gly Leu Ser
465                 470                 475                 480
Gly Tyr Met Lys Thr Glu Asp Leu Gln Ala Leu Asp Ala Ser Lys Asp
                485                 490                 495
Phe Ile Pro Tyr Tyr Glu Ser Asp Gly His Arg Phe Tyr His Tyr Val
            500                 505                 510
Ala Gln Asn Ala Ser Ile Pro Val Ala Ser His Leu Ser Asp Met Glu
        515                 520                 525
Val Gly Lys Lys Tyr Tyr Ser Ala Asp Gly Leu His Phe Asp Gly Phe
    530                 535                 540
Lys Leu Glu Asn Pro Phe Leu Phe Lys Asp Leu Thr Glu Ala Thr Asn
545                 550                 555                 560
Tyr Ser Ala Glu Glu Leu Asp Lys Val Phe Ser Leu Leu Asn Ile Asn
                565                 570                 575
Asn Ser Leu Leu Glu Asn Lys Gly Ala Thr Phe Lys Glu Ala Glu Glu
            580                 585                 590
His Tyr His Ile Asn Ala Leu Tyr Leu Leu Ala His Ser Ala Leu Glu
        595                 600                 605
Ser Asn Trp Gly Arg Ser Lys Ile Ala Lys Asp Lys Asn Asn Phe Phe
    610                 615                 620
Gly Ile Thr Ala Tyr Asp Thr Thr Pro Tyr Leu Ser Ala Lys Thr Phe
625                 630                 635                 640
Asp Asp Val Asp Lys Gly Ile Leu Gly Ala Thr Lys Trp Ile Lys Glu
                645                 650                 655
Asn Tyr Ile Asp Arg Gly Arg Thr Phe Leu Gly Asn Lys Ala Ser Gly
            660                 665                 670
Met Asn Val Glu Tyr Ala Ser Asp Pro Tyr Trp Gly Glu Lys Ile Ala
        675                 680                 685
Ser Val Met Met Lys Ile Asn Glu Lys Leu Gly Gly Lys Asp
    690                 695                 700

<210> SEQ ID NO 10
<211> LENGTH: 677
<212> TYPE: PRT
<213> ORGANISM: Streptococcus pneumoniae

<400> SEQUENCE: 10

Met Asn Leu Gly Glu Phe Trp Tyr Asn Lys Ile Asn Lys Asn Arg Gly
1               5                   10                  15
Arg Arg Leu Met Lys Lys Val Arg Phe Ile Phe Leu Ala Leu Leu Phe
            20                  25                  30
Phe Leu Ala Ser Pro Glu Gly Ala Met Ala Ser Asp Gly Thr Trp Gln
        35                  40                  45
Gly Lys Gln Tyr Leu Lys Glu Asp Gly Ser Gln Ala Ala Asn Glu Trp
    50                  55                  60
Val Phe Asp Thr His Tyr Gln Ser Trp Phe Tyr Ile Lys Ala Asp Ala
65                  70                  75                  80
Asn Tyr Ala Glu Asn Glu Trp Leu Lys Gln Gly Asp Asp Tyr Phe Tyr
                85                  90                  95
```

-continued

```
Leu Lys Ser Gly Gly Tyr Met Ala Lys Ser Glu Trp Val Glu Asp Lys
                100                 105                 110

Gly Ala Phe Tyr Tyr Leu Asp Gln Asp Gly Lys Met Lys Arg Asn Ala
            115                 120                 125

Trp Val Gly Thr Ser Tyr Val Gly Ala Thr Gly Ala Lys Val Ile Glu
130                 135                 140

Asp Trp Val Tyr Asp Ser Gln Tyr Asp Ala Trp Phe Tyr Ile Lys Ala
145                 150                 155                 160

Asp Gly Gln His Ala Glu Lys Glu Trp Leu Gln Ile Lys Gly Lys Asp
                165                 170                 175

Tyr Tyr Phe Lys Ser Gly Gly Tyr Leu Leu Thr Ser Gln Trp Ile Asn
            180                 185                 190

Gln Ala Tyr Val Asn Ala Ser Gly Ala Lys Val Gln Gln Gly Trp Leu
        195                 200                 205

Phe Asp Lys Gln Tyr Gln Ser Trp Phe Tyr Ile Lys Glu Asn Gly Asn
    210                 215                 220

Tyr Ala Asp Lys Glu Trp Ile Phe Glu Asn Gly His Tyr Tyr Tyr Leu
225                 230                 235                 240

Lys Ser Gly Gly Tyr Met Ala Ala Asn Glu Trp Ile Trp Asp Lys Glu
                245                 250                 255

Ser Trp Phe Tyr Leu Lys Phe Asp Gly Lys Met Ala Glu Lys Glu Trp
            260                 265                 270

Val Tyr Asp Ser His Ser Gln Ala Trp Tyr Tyr Phe Lys Ser Gly Gly
        275                 280                 285

Tyr Met Thr Ala Asn Glu Trp Ile Trp Asp Lys Glu Ser Trp Phe Tyr
    290                 295                 300

Leu Lys Ser Asp Gly Lys Ile Ala Glu Lys Glu Trp Val Tyr Asp Ser
305                 310                 315                 320

His Ser Gln Ala Trp Tyr Tyr Phe Lys Ser Gly Gly Tyr Met Thr Ala
                325                 330                 335

Asn Glu Trp Ile Trp Asp Lys Glu Ser Trp Phe Tyr Leu Lys Ser Asp
            340                 345                 350

Gly Lys Ile Ala Glu Lys Glu Trp Val Tyr Asp Ser His Ser Gln Ala
        355                 360                 365

Trp Tyr Tyr Phe Lys Ser Gly Gly Tyr Met Ala Lys Asn Glu Thr Val
    370                 375                 380

Asp Gly Tyr Gln Leu Gly Ser Asp Gly Lys Trp Leu Gly Gly Lys Thr
385                 390                 395                 400

Thr Asn Glu Asn Ala Ala Tyr Tyr Gln Val Pro Val Thr Ala Asn
                405                 410                 415

Val Tyr Asp Ser Asp Gly Glu Lys Leu Ser Tyr Ile Ser Gln Gly Ser
            420                 425                 430

Val Val Trp Leu Asp Lys Asp Arg Lys Ser Asp Asp Lys Arg Leu Ala
        435                 440                 445

Ile Thr Ile Ser Gly Leu Ser Gly Tyr Met Lys Thr Glu Asp Leu Gln
    450                 455                 460

Ala Leu Asp Ala Ser Lys Asp Phe Ile Pro Tyr Tyr Glu Ser Asp Gly
465                 470                 475                 480

His Arg Phe Tyr His Tyr Val Ala Gln Asn Ala Ser Ile Pro Val Ala
                485                 490                 495

Ser His Leu Ser Asp Met Glu Val Gly Lys Lys Tyr Tyr Ser Ala Asp
            500                 505                 510
```

```
Gly Leu His Phe Asp Gly Phe Lys Leu Glu Asn Pro Phe Leu Phe Lys
            515                 520                 525

Asp Leu Thr Glu Ala Thr Asn Tyr Ser Ala Glu Glu Leu Asp Lys Val
530                 535                 540

Phe Ser Leu Leu Asn Ile Asn Asn Ser Leu Leu Glu Asn Lys Gly Ala
545                 550                 555                 560

Thr Phe Lys Glu Ala Glu Glu His Tyr His Ile Asn Ala Leu Tyr Leu
                565                 570                 575

Leu Ala His Ser Ala Leu Glu Ser Asn Trp Gly Arg Ser Lys Ile Ala
            580                 585                 590

Lys Asp Lys Asn Asn Phe Phe Gly Ile Thr Ala Tyr Asp Thr Thr Pro
        595                 600                 605

Tyr Leu Ser Ala Lys Thr Phe Asp Asp Val Asp Lys Gly Ile Leu Gly
    610                 615                 620

Ala Thr Lys Trp Ile Lys Glu Asn Tyr Ile Asp Arg Gly Arg Thr Phe
625                 630                 635                 640

Leu Gly Asn Lys Ala Ser Gly Met Asn Val Glu Tyr Ala Ser Asp Pro
                645                 650                 655

Tyr Trp Gly Glu Lys Ile Ala Ser Val Met Met Lys Ile Asn Glu Lys
            660                 665                 670

Leu Gly Gly Lys Asp
            675

<210> SEQ ID NO 11
<211> LENGTH: 281
<212> TYPE: PRT
<213> ORGANISM: Streptococcus pneumoniae

<400> SEQUENCE: 11

Met Gly Lys Ala Thr Asn Glu Asn Ala Ala Tyr Tyr Gln Val Val Pro
1               5                   10                  15

Val Thr Ala Asn Val Tyr Asp Ser Asp Gly Glu Lys Leu Ser Tyr Ile
            20                  25                  30

Ser Gln Gly Ser Val Val Trp Leu Asp Lys Asp Arg Lys Ser Asp Asp
        35                  40                  45

Lys Arg Leu Ala Ile Thr Ile Ser Gly Leu Ser Gly Tyr Met Lys Thr
50                  55                  60

Glu Asp Leu Gln Ala Leu Asp Ala Ser Lys Asp Phe Ile Pro Tyr Tyr
65                  70                  75                  80

Glu Ser Asp Gly His Arg Phe Tyr His Tyr Val Ala Gln Asn Ala Ser
                85                  90                  95

Ile Pro Val Ala Ser His Leu Ser Asp Met Ala Val Gly Lys Lys Tyr
            100                 105                 110

Tyr Ser Ala Asp Gly Leu His Phe Asp Gly Phe Lys Leu Glu Asn Pro
        115                 120                 125

Phe Leu Phe Lys Asp Leu Thr Glu Ala Thr Asn Tyr Ser Ala Glu Glu
    130                 135                 140

Leu Asp Lys Val Phe Ser Leu Leu Asn Ile Asn Asn Ser Leu Leu Glu
145                 150                 155                 160

Asn Lys Gly Ala Thr Phe Lys Glu Ala Glu Glu His Tyr His Ile Asn
                165                 170                 175

Ala Leu Tyr Leu Leu Ala His Ser Ala Leu Glu Ser Asn Trp Gly Arg
            180                 185                 190

Ser Lys Ile Ala Lys Asp Lys Asn Asn Phe Phe Gly Ile Thr Ala Tyr
        195                 200                 205
```

```
Asp Thr Thr Pro Tyr Leu Ser Ala Lys Thr Phe Asp Val Asp Lys
        210                 215                 220

Gly Ile Leu Gly Ala Thr Lys Trp Ile Lys Glu Asn Tyr Ile Asp Arg
225                 230                 235                 240

Gly Arg Thr Phe Leu Gly Asn Lys Ala Ser Gly Met Asn Val Glu Tyr
                245                 250                 255

Ala Ser Asp Pro Tyr Trp Gly Glu Lys Ile Ala Ser Val Met Met Lys
        260                 265                 270

Ile Asn Glu Lys Leu Gly Gly Lys Asp
        275                 280

<210> SEQ ID NO 12
<211> LENGTH: 471
<212> TYPE: PRT
<213> ORGANISM: Streptococcus pneumoniae

<400> SEQUENCE: 12

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
```

```
                    290                 295                 300
Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Thr Leu Tyr Pro Gln Val
                450                 455                 460

Glu Asp Lys Val Glu Asn Asp
465                 470
```

<210> SEQ ID NO 13
<211> LENGTH: 471
<212> TYPE: PRT
<213> ORGANISM: Streptococcus pneumoniae

<400> SEQUENCE: 13

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
                35                  40                  45

Lys Lys Arg Ser Leu Ser Thr Asn Thr Ser Asp Ile Ser Val Thr Ala
                50                  55                  60

Cys Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
                130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190
```

-continued

```
Val Asn Phe Lys Gln Ile Tyr Tyr Thr Val Ser Val Asp Ala Val Lys
    195                 200                 205
Asn Pro Gly Asp Val Phe Gln Asp Thr Val Thr Val Glu Asp Leu Lys
    210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
                260                 265                 270
Ala Pro Gln Thr Glu Trp Lys Gln Ile Leu Asp Asn Thr Glu Val Lys
                275                 280                 285
Ala Val Ile Leu Cys Gly Asp Pro Ser Ser Gly Ala Arg Val Val Thr
            290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Asp Tyr Val Glu
                340                 345                 350
Thr Lys Val Thr Ala Tyr Arg Asn Gly Asp Leu Leu Leu Asp His Ser
            355                 360                 365
Gly Ala Tyr Val Ala Gln Tyr Tyr Ile Thr Trp Asp Glu Leu Ser Tyr
        370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Ala Thr Gly Leu Ala
                420                 425                 430
Trp Glu Trp Trp Arg Thr Val Tyr Glu Lys Thr Asp Leu Pro Leu Val
            435                 440                 445
Arg Lys Arg Thr Ile Ser Ile Trp Gly Thr Thr Leu Tyr Pro Gln Val
    450                 455                 460
Glu Asp Lys Val Glu Asn Asp
465                 470
```